US009597314B2

(12) United States Patent
Koppel et al.

(10) Patent No.: US 9,597,314 B2
(45) Date of Patent: Mar. 21, 2017

(54) BETA-LACTAMYLALKANOIC ACIDS FOR TREATING PREMENSTRUAL DISORDERS

(75) Inventors: Gary A. Koppel, Indianapolis, IN (US); Marvin J. Miller, South Bend, IN (US)

(73) Assignee: AZEVAN PHARMACEUTICALS, INC., Bethlehem, PA (US)

( * ) Notice: Subject to any disclaimer, the term of this patent is extended or adjusted under 35 U.S.C. 154(b) by 1339 days.

(21) Appl. No.: 11/909,344

(22) PCT Filed: Mar. 21, 2006

(86) PCT No.: PCT/US2006/010143
§ 371 (c)(1),
(2), (4) Date: Sep. 8, 2008

(87) PCT Pub. No.: WO2006/102283
PCT Pub. Date: Sep. 28, 2006

(65) Prior Publication Data
US 2009/0170825 A1 Jul. 2, 2009

Related U.S. Application Data

(60) Provisional application No. 60/664,239, filed on Mar. 22, 2005, provisional application No. 60/700,673, filed on Jul. 19, 2005.

(51) Int. Cl.
*A01N 43/00* (2006.01)
*A61K 31/397* (2006.01)

(52) U.S. Cl.
CPC .................. *A61K 31/397* (2013.01)

(58) Field of Classification Search
CPC .............. A61K 31/397; A61P 15/00
USPC .................. 514/210.02
See application file for complete search history.

(56) References Cited

U.S. PATENT DOCUMENTS

| | | | |
|---|---|---|---|
| 3,912,743 A | 10/1975 | Christensen et al. | |
| 4,007,196 A | 2/1977 | Christensen et al. | |
| 4,085,225 A | 4/1978 | Welle et al. | |
| 4,136,193 A | 1/1979 | Bogese et al. | |
| 4,314,081 A | 2/1982 | Molloy et al. | |
| 4,341,698 A | 7/1982 | Carr | |
| 4,352,752 A | 10/1982 | Ojima | |
| 4,478,836 A | 10/1984 | Mouzin et al. | |
| 4,536,518 A | 8/1985 | Welch | |
| 4,576,753 A | 3/1986 | Kamiya | |
| 4,734,498 A | 3/1988 | Cooper et al. | |
| 4,751,299 A | 6/1988 | Sugawara et al. | |
| 4,761,501 A | 8/1988 | Husbands et al. | |
| 4,772,694 A | 9/1988 | Cooper et al. | |
| 4,956,388 A | 9/1990 | Robertson et al. | |
| 5,011,472 A | 4/1991 | Aebischer et al. | |
| 5,023,252 A | 6/1991 | Hseih | |
| 5,246,943 A * | 9/1993 | Blankley ............... | C07C 43/225 514/307 |
| 5,338,744 A * | 8/1994 | Dudley ............... | A61K 31/44 514/303 |
| 5,759,865 A | 6/1998 | Bruns et al. | |
| 6,054,457 A | 4/2000 | Setoi | |
| 6,204,260 B1 | 3/2001 | Bruns, Jr. et al. | |
| 6,403,632 B1 | 6/2002 | Duan et al. | |
| 6,610,680 B1 | 8/2003 | Bruns et al. | |
| 6,627,625 B1 | 9/2003 | Koppel | |
| 7,119,083 B2 | 10/2006 | Bruns, Jr. et al. | |
| 7,179,907 B2 | 2/2007 | Eaton et al. | |
| 7,268,125 B2 | 9/2007 | Bruns, Jr. et al. | |
| 8,048,874 B2 | 11/2011 | Koppel | |
| 2004/0132714 A1 | 7/2004 | Zhou et al. | |
| 2004/0266750 A1 | 12/2004 | Bruns | |
| 2005/0059650 A1 | 3/2005 | Jones et al. | |
| 2006/0281728 A1 | 12/2006 | Guillon et al. | |
| 2008/0033165 A1 | 2/2008 | Koppel | |
| 2008/0076754 A1 | 3/2008 | Xiang | |
| 2008/0280870 A1 | 11/2008 | Koppel | |
| 2009/0170825 A1 | 7/2009 | Koppel | |
| 2010/0016274 A1 | 1/2010 | Koppel | |
| 2010/0137402 A1 | 6/2010 | Ducoux | |
| 2010/0317652 A1 | 12/2010 | Bryans | |
| 2011/0059935 A1 | 3/2011 | Bruns | |
| 2011/0071160 A1 | 3/2011 | Couturier | |

FOREIGN PATENT DOCUMENTS

| | | |
|---|---|---|
| CN | 1106802 | 8/1995 |
| CN | 2000504731 | 4/2000 |
| CN | 1606554 A | 4/2005 |
| CN | 1272111 | 8/2006 |
| EP | 0144840 | 6/1985 |
| EP | 0591040 | 9/1993 |
| JP | 56 125361 | 10/1981 |
| WO | WO 93/16609 | 6/1993 |
| WO | WO94/01402 | 1/1994 |

(Continued)

OTHER PUBLICATIONS

Stromberg et al. (Acta Obstetricia et Gynecologica Scandinavica, 63, 6, 533-38), 1984.*
Thibonnier et al. (Ann. Review of Pharmacol. Toxicol, 2001, 41, 175-202).*
Bhatia et al. (American Family Physician, 66, 7, 2002, p. 1239-1248).*
Sampalis et al. (Alternative Medicine Review, 8, 2, 2003).*
Dickerson et al. (American Family Physician, Apr. 15, 2003 67(8), 1743-52).*

(Continued)

*Primary Examiner* — Uma Ramachandran
(74) *Attorney, Agent, or Firm* — Brannon Sowers & Cracraft PC

(57) ABSTRACT

0-lactamyl alkanoic acids are described. Methods for treating various premenstrual disorders using or more β-lactamyl alkanoic acids are also described.

8 Claims, 1 Drawing Sheet

(56) References Cited

FOREIGN PATENT DOCUMENTS

| WO | 9404494 | A1 | 3/1994 |
|---|---|---|---|
| WO | WO94/04494 | | 3/1994 |
| WO | WO 94/26735 | | 11/1994 |
| WO | WO 97/30707 | | 8/1997 |
| WO | WO 02/12187 | | 2/2002 |
| WO | WO 03/031407 | | 4/2003 |
| WO | 2006061407 | A2 | 6/2006 |
| WO | 2006102283 | A2 | 9/2006 |
| WO | 2007109615 | | 9/2007 |

OTHER PUBLICATIONS

Jarrahpour, Molbank 2005, M439 (Oct. 1, 2005).
Jarrahpour, Molecules 2004, 9, 939-948.
Ojima et al., "Asymmetric Alkylations of a Phenylalanylglycinate Equivalent. New routes to Dipeptides Bearing α-Alkyl-α-amino Acid Residues", J. Amer. Chem. Soc., vol. 112, pp. 770-774, (1990).
Ojima et al., J. Amer. Chem. Soc., vol. 109, pp. 6537-6538 (1987).
Ojima et al., "Novel and Effective Routes to Optically Pure Amino Acids, Dipeptides, and Their Derivatives via β-Lactams Obtained Through Asymmetric Cycloaddition," J. Chem. Soc., Chem. Commun., (8), 625-626 (1987).
Hirai et al, "An Example of the β-Lactam Ring Formation and Novel Pyrrolinoazetidinone Ring Construction", Sankyo Kenyusho Nempo, vol. 37, pp. 133-139, (1985).
STNweb20100331X225934, 2010.
Hakimelahi, "The Synthesis of Highly Strained Monocyclic and Bicyclic Beta-Lactams (delta-Carbapenem)," Helvetica Chimica Acta, 1982, 65 Fasc., pp. 1378-1384.
PCT International Search Report for PCT/US06/10192 completed by the U. S. Searching Authority (Jul. 1, 2008).
Serradeil-LeGal, et al., Biochemical and Pharmacological Properties of SR 49059, Journal of Clinical Investigation, 1993, vol. 92, 224-231.
R. Brouard et al., "Effect of SR49059, an orally active $V_{1a}$ vasopressin receptor antagonist, in the prevention of dysmenorrhoea", British Journal of Obstetrics and Gynecology, May 2000, vol. 107, pp. 614-619.
Ragner Liedman et al., "Intrauterine pressure, ischemia markers, and experienced pain during administration of a vasopressin $V_{1a}$ receptor antagonist in spontaneous and vasopressin-induced dysmenorrheal", Acta Obstetricia et Gynecologica. 85: 207-211, (2005).
European Search Report for EP 06739075.7, dated Sep. 22, 2011.
Brouard, R., "Effect of SR49059, an orally active V1a vasopressin receptor antagonist, in the prevention of dysmenorrhoea," British Journal of Obstetrics and Gynecology, May 2000, vol. 107, pp. 614-619.
Ojima, Iwao, Takeo Komata, and Xiaogang Qiu. "Asymmetric alkylations of a phenylalanylglycinate equivalent. Novel route to dipeptides bearing. alpha.-alkyl-. alpha.-amino.acid residues." Journal of the American Chemical Society 112.2 (1990): 770-774.
Ojima, Iwao, and Xiaogang Qiu. "Asymmetric alkylation of chiral. beta.-lactam ester enolates. A new approach to the synthesis of. alpha.-alkylated. alpha.-amino acids." Journal of the American Chemical Society 109.21 (1987): 6537-6538.
Ojima, Iwao, and Hauh-Jyun C. Chen. "Novel and effective routes to optically pure amino acids, dipeptides, and their derivatives via $^2$-lactams obtained through asymmetric cycloaddition." Journal of the Chemical Society, Chemical Communications 8 (1987): 625-626.
International Search Report and Written Opinion for PCT/US2007/078451 completed Apr. 23, 2008.
International Search Report and Written Opinion for PCT/US2006/010192 completed Jul. 1, 2008.
Ghosh, M. et al, Journal of the Indian Chemical Society, 1985, 62(6), pp. 457-459.
Petit, Samuel, and Gérard Coquerel. "The amorphous state." Polymorphism: In the Pharmaceutical Industry 10 (2006): 1.
Chemical Abstracts AN:1992:6288, 1990.
Office Action for U.S. Appl. No. 11/442,788 dated Nov. 2, 2006, 16 pages.
Office Action for U.S. Apppl. No. 11/835,017 dated Apr. 16, 2008, 5 pages.
PCT International Search Report for PCT/US2007/006555 completed by the US Searching Authority on Jun. 16, 2008.
PCT International Search Report for PCT/US2007/064309 completed by the US Searching Authority on Oct. 1, 2007.
Office Action for U.S. Appl. No. 10/492,323 dated Mar. 7, 2005, 16 pages.
PCT International Search Report for PCT/US2006/027703, dated Mar. 30, 2007.
Surget et al.: 'Involvement of Vasopressin in Affective Disorders' European Journal Pharmacology vol. 583, 2008, pp. 340-349, XP022532879.
PCT International Search Report for PCT/US04/32401 competed by the U.S. Searching Authority on Mar. 2, 2005.
Office Action for U.S. Appl. No. 10/492,323 dated Nov. 9, 2005, 13 pages.
Ferris C F et al: "Orally active vasopressin V1a receptor antagonist, SRX251, selectively blocks aggressive behavior", Pharmacology Biochemistry and Behavior, Elsevier, US, vol. 83, No. 2, Feb. 1, 2006 (Feb. 1, 2006), pp. 169-174, XP027929666, ISSN: 0091-3057 [retrieved on Feb. 1, 2006].
Guillon et al: "Azetidinones as vasopressin V1a antagonists", Bioorganic & Medicinal Chemistry, Pergamon, GB, vol. 15, No. 5, Jan. 31, 2007 (Jan. 31, 2007), pp. 2054-2080, XP005867173, ISSN: 0968-0896, DOI: 10.1016/J.BMC.2006.12.031.
De Kloet et al: "Elevated plasma arginine vasopressin levels in veterans with posttraumatic stress disorder", Journal of Psychiatric Research, Elsevier Ltd, GB, vol. 42, No. 3, Dec. 20, 2007 (Dec. 20, 2007), pp. 192-198, XP022395299, ISSN: 0022-3956.
International Search Report and Written Opinion for PCT/US2015/023060 completed Jun. 24, 2015.

* cited by examiner

BETA-LACTAMYLALKANOIC ACIDS FOR TREATING PREMENSTRUAL DISORDERS

CROSS REFERENCE TO RELATED APPLICATIONS

This application is a U.S. national counterpart application of International Application No. PCT/US2006/010143 filed Mar. 21, 2006, which claims the benefit of U.S. Provisional Patent Application No. 60/664,239, filed Mar. 22, 2005, and to U.S. Provisional Patent Application No. 60/700,673, filed Jul. 19, 2005. The entireties of all of the disclosures of which are incorporated herein by reference.

GOVERNMENT RIGHTS

This invention was made with government support under R41 MH063663 and R44 MH063663 awarded by the National Institutes of Health, the United States government has certain rights in the invention.

TECHNICAL FIELD

This invention pertains to substituted 2-(azetidin-2-on-1-yl)alkanoic acids and derivatives thereof. This invention also pertains to methods for treating premenstrual disorders. In particular, this invention pertains to the use of β-lactamyl vasopressin antagonists for treating premenstrual disorders.

BACKGROUND

Arginine vasopressin (AVP) is a neurohypophyseal neuropeptide produced in the hypothalamus, and is involved in many biological processes in the circulatory system, the peripheral nervous system (PNS), and the central nervous system (CNS). In particular, AVP acts as a neurotransmitter in the brain. Several pharmacologically significant vasopressin receptor subtypes, including vasopressin $V_{1a}$, $V_{1b}$, and $V_2$, have been identified. Such vasopressin receptors are involved in several psychiatric, psychological, and behavioral disease states including depression, anxiety, affective disorders, and stress, as well as non-opioid mediation of tolerance for pain. Vasopressin receptors are also involved in a number of metabolic processes including water metabolism homeostasis, renal function, mediation of cardiovascular function, and regulation of temperature in mammals.

Structural modification of vasopressin has provided a number of vasopressin agonists (see, Sawyer, *Pharmacol. Reviews*, 13:255 (1961)). In addition, several potent and selective vasopressin peptide antagonists have been disclosed (see, Lazslo et al., *Pharmacological Reviews*, 43:73-108 (1991); Mah and Hofbauer, *Drugs of the Future*, 12:1055-1070 (1987); Manning and Sawyer, *Trends in Neuroscience*, 7:8-9 (1984)). Further, novel structural classes of non-peptidyl vasopressin antagonists have been disclosed (see, Yamamura et al., *Science*, 275:572-574 (1991); Serradiel-Le Gal et al., *Journal of Clinical Investigation*, 92:224-231 (1993); Serradiel-Le Gal et al., *Biochemical Pharmacology*, 47(4):633-641 (1994)). Finally, the general structural class of substituted 2-(azetidin-2-on-1-yl)acetic acid esters and amides are known as synthetic intermediates for the preparation of β-lactam antibiotics (see, U.S. Pat. No. 4,751,299).

SUMMARY OF THE INVENTION

Methods for treating premenstrual disorders are described herein. In one illustrative embodiment, the premenstrual disorder is primary dysmenorrhoea (PD). In another illustrative embodiment, the premenstrual disorder is premenstrual dysmenorrhoea dysphoria (PMDD). The methods described herein include the step of administering one or more β-lactamyl vasopressin antagonists, including the β-lactamylalkanoic acids described herein, to a female patient in need of relief from a premenstrual disorder, such as PD, PMDD, and/or associated accompanying symptoms of such premenstrual dysfunction.

In one illustrative embodiment of the methods described herein, one or more compounds of the formula:

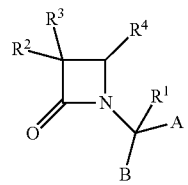

and pharmaceutically acceptable salts thereof, are administered to the patient; wherein A is a carboxylic acid, an ester, or an amide;

B is a carboxylic acid, or an ester or amide derivative thereof; or B is an alcohol or thiol, or a derivative thereof;

$R^1$ is hydrogen or $C_1$-$C_6$ alkyl;

$R^2$ is hydrogen, alkyl, alkenyl, alkynyl, alkoxy, alkylthio, halo, haloalkyl, cyano, formyl, alkylcarbonyl, or a substituent selected from the group consisting of —$CO_2R^8$, —$CONR^8R^{8'}$, and —$NR^8(COR^9)$; where $R^8$ and $R^{8'}$ are each independently selected from hydrogen, alkyl, cycloalkyl, optionally substituted aryl, or optionally substituted arylalkyl; or $R^8$ and $R^{8'}$ are taken together with the attached nitrogen atom to form a heterocyclyl group; and where $R^9$ is selected from hydrogen, alkyl, cycloalkyl, alkoxyalkyl, optionally substituted aryl, optionally substituted arylalkyl, optionally substituted heteroaryl, optionally substituted heteroarylalkyl, and $R^8R^{8'}N$—($C_1$-$C_4$ alkyl);

$R^3$ is an amino, amido, acylamido, or ureido group, which is optionally substituted; or $R^3$ is a nitrogen-containing heterocyclyl group attached at a nitrogen atom; and $R^4$ is alkyl, alkenyl, alkynyl, cycloalkyl, cycloalkenyl, alkylcarbonyl, optionally substituted aryl, optionally substituted arylalkyl, optionally substituted arylhaloalkyl, optionally substituted arylalkoxyalkyl, optionally substituted arylalkenyl, optionally substituted arylhaloalkenyl, or optionally substituted arylalkynyl.

In another illustrative embodiment of the methods described herein, one or more compounds of formula (I):

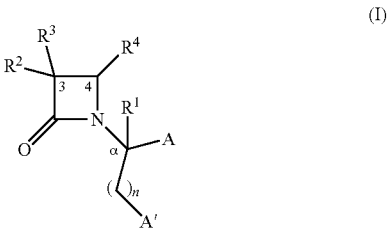

(I)

and pharmaceutically acceptable salts thereof, are administered to the patient; wherein A and A' are each independently selected from —$CO_2H$, or an ester or amide derivative thereof;

n is an integer selected from 0 to about 3;

R$^1$ is hydrogen or C$_1$-C$_6$ alkyl;

R$^2$ is hydrogen, alkyl, alkenyl, alkynyl, alkoxy, alkylthio, halo, haloalkyl, cyano, formyl, alkylcarbonyl, or a substituent selected from the group consisting of —CO$_2$R$^8$, —CONR$^8$R$^{8'}$, and —NR$^8$(COR$^9$); where R$^8$ and R$^{8'}$ are each independently selected from hydrogen, alkyl, cycloalkyl, optionally substituted aryl, or optionally substituted arylalkyl; or R$^8$ and R$^{8'}$ are taken together with the attached nitrogen atom to form an heterocycle; and where R$^9$ is selected from hydrogen, alkyl, cycloalkyl, alkoxyalkyl, optionally substituted aryl, optionally substituted arylalkyl, optionally substituted heteroaryl, optionally substituted heteroarylalkyl, and R$^8$R$^{8'}$—(C$_1$-C$_4$ alkyl);

R$^3$ is an amino, amido, acylamido, or ureido group, which is optionally substituted; or R$^3$ is a nitrogen-containing heterocyclyl group attached at a nitrogen atom; and R$^4$ is alkyl, alkenyl, alkynyl, cycloalkyl, cycloalkenyl, alkylcarbonyl, optionally substituted aryl, optionally substituted arylalkyl, optionally substituted arylhaloalkyl, optionally substituted arylalkoxyalkyl, optionally substituted arylalkenyl, optionally substituted arylhaloalkenyl, or optionally substituted arylalkynyl.

In another illustrative embodiment of the methods described herein, one or more compounds of formula (II):

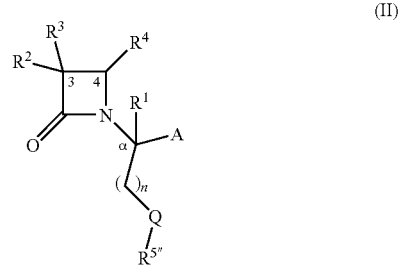

(II)

and pharmaceutically acceptable salts thereof, are administered to the patient; wherein A is —CO$_2$H, or an ester or amide derivative thereof;

Q is oxygen; or Q is sulfur or disulfide, or an oxidized derivative thereof;

n is an integer from 1 to 3;

R$^1$, R$^2$, R$^3$, and R$^4$ are as defined in formula I; and

R$^{5''}$ is selected from hydrogen, alkyl, cycloalkyl, alkoxyalkyl, optionally substituted arylalkyl, optionally substituted heterocyclyl or optionally substituted heterocyclylalkyl, and optionally substituted aminoalkyl.

DETAILED DESCRIPTION

Figure 1:
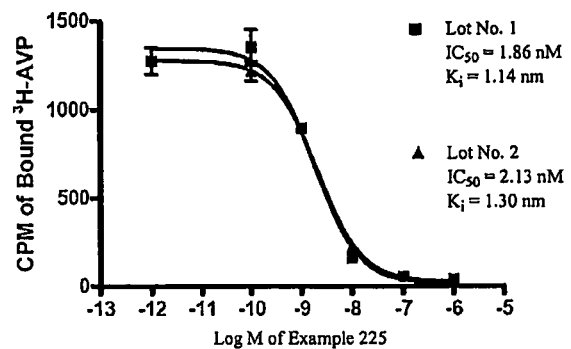
FIG. 1 shows the binding affinity of two preparation lots of Example 225 on human vasopressin V$_{1a}$ receptors.
Figure 2:
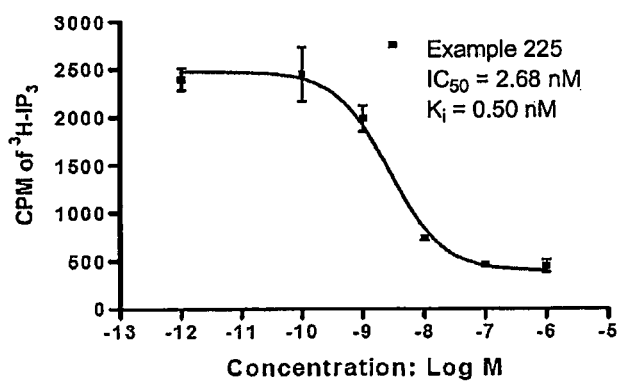
FIG. 2 shows the antagonism of arginine vasopressin-induced inositol-3-phosphate production by Example 225.
Figure 3:
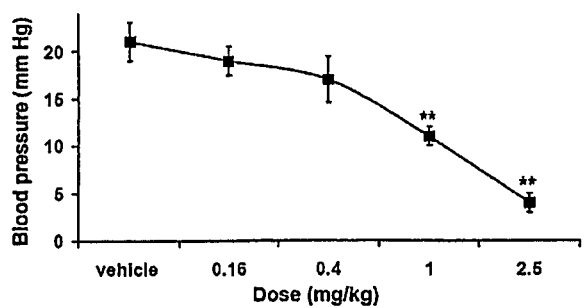
FIG. 3 shows the blocking of arginine vasopressin-induced increases in blood pressure in rats by Example 225.

In one embodiment of the compounds of formulae (I) or (II), A is —CO$_2$R$^5$; where R$^5$ is selected from hydrogen, alkyl, cycloalkyl, alkoxyalkyl, optionally substituted arylalkyl, heterocyclyl, heterocyclyl(C$_1$-C$_4$ alkyl), and R$^6$R$^7$N—(C$_2$-C$_4$ alkyl). In another embodiment of the compounds of formulae (I) or (II), A is monosubstituted amido, disubstituted amido, or an optionally substituted nitrogen-containing heterocyclylamido.

It is to be understood that in each occurrence of the various embodiments described herein, heterocyclyl is independently selected in each instance. In one illustrative aspect, heterocyclyl is independently selected from tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with C$_1$-C$_4$ alkyl or optionally substituted aryl(C$_1$-C$_4$ alkyl).

It is also to be understood that in each occurrence of the various embodiments described herein, R$^6$ and R$^7$ are each independently selected in each instance. In another illustrative aspect, R$^6$ is independently selected from hydrogen or alkyl; and R$^7$ is independently selected in each instance from alkyl, cycloalkyl, optionally substituted aryl, or optionally substituted arylalkyl. In another illustrative aspect, R$^6$ and R$^7$ are taken together with the attached nitrogen atom to form an optionally substituted heterocycle, such as pyrrolidinyl, piperidinyl, morpholinyl, piperazinyl, and homopiperazinyl; where said piperazinyl or homopiperazinyl is also optionally N-substituted with R$^{13}$; where R$^{13}$ is independently selected in each instance from hydrogen, alkyl, cycloalkyl, alkoxycarbonyl, optionally substituted aryloxycarbonyl, optionally substituted arylalkyl, and optionally substituted aryloyl.

In another embodiment, compounds of formula (I) are described that are diesters, acid-esters, or diacids, including pharmaceutically acceptable salts thereof, where each of A and A' is independently selected. In another embodiment, compounds of formula (I) are described that are ester-amides, where one of A and A' is an ester, and the other is an amide. In another embodiment, compounds of formula (I) are described that are diamides, where each of A and A' are independently selected from monosubstituted amido, disubstituted amido, and optionally substituted nitrogen-containing heterocyclylamido.

In one variation of the compounds of formula (I), A and/or A' is an independently selected monosubstituted amido of the formula C(O)NHX—, where X is selected from alkyl, cycloalkyl, alkoxyalkyl, optionally substituted aryl, optionally substituted arylalkyl, heterocyclyl, heterocyclyl-(C$_1$-C$_4$ alkyl), R$^6$R$^7$N—, and R$^6$R$^7$N—(C$_1$-C$_4$ alkyl), where each heterocyclyl is independently selected.

In another variation, A and/or A' is an independently selected disubstituted amido of the formula C(O)NR$^{14}$X—, where R$^{14}$ is selected from hydroxy, alkyl, alkoxycarbonyl, and benzyl; and X is selected from alkyl, cycloalkyl, alkoxyalkyl, optionally substituted aryl, optionally substituted arylalkyl, heterocyclyl, heterocyclyl-(C$_1$-C$_4$ alkyl), R$^6$R$^7$N—, and R$^6$R$^7$N—(C$_2$-C$_4$ alkyl), where each heterocyclyl is independently selected.

In another variation, A and/or A' is an amide of an independently selected optionally substituted nitrogen-containing heterocycle attached at a nitrogen. Illustrative nitrogen-containing heterocycles include but are not limited to pyrrolidinyl, piperidinyl, piperazinyl, homopiperazinyl, triazolidinyl, triazinyl, oxazolidinyl, isoxazolidinyl, thiazolidinyl, isothiazolidinyl, 1,2-oxazinyl, 1,3-oxazinyl, morpholinyl, oxadiazolidinyl, and thiadiazolidinyl; each of which is optionally substituted. Such optional substitutions include the groups R$^{10}$, R$^{12}$, R$^6$R$^7$N—, and R$^6$R$^7$N—(C$_1$-C$_4$ alkyl), as defined herein. In one embodiment, A and/or A' is independently selected from pyrrolidinonyl, piperidinonyl, 2-(pyrrolidin-1-ylmethyl)pyrrolidin-1-yl, or 1,2,3,4-tetrahydroisoquinolin-2-yl, each of which is optionally substituted, and attached at a nitrogen.

In another variation, A and/or A' is an independently selected amide of an optionally substituted piperidinyl attached at the nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))—($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A and/or A' is an independently selected piperidinyl substituted at the 4-position and attached at the nitrogen.

In another variation, A and/or A' is an independently selected amide of an optionally substituted piperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))—($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A and/or A' is an independently selected piperazinyl substituted at the 4-position and attached at a nitrogen.

In another variation, A and/or A' is an independently selected amide of an optionally substituted homopiperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))—($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A and/or A' is an independently selected homopiperazinyl substituted at the 4-position and attached at a nitrogen. In another embodiment, A and/or A' is an independently selected homopiperazinyl substituted at the 4-position with alkyl, aryl, aryl($C_1$-$C_4$ alkyl), and attached at a nitrogen.

In another embodiment of the compounds of formula (I), A' is monosubstituted amido, disubstituted amido, or an optionally substituted nitrogen-containing heterocyclylamido. In another embodiment of the compounds of formula (I), A' is —$CO_2R^{5'}$; where $R^{5'}$ is selected from hydrogen, alkyl, cycloalkyl, alkoxyalkyl, optionally substituted arylalkyl, heterocyclyl, heterocyclyl($C_1$-$C_4$ alkyl), and $R^6R^7N$—($C_2$-$C_4$ alkyl); where heterocyclyl is in each occurrence independently selected from tetrahydrofuryl, morpholinyl, pyrrolidinyl, piperidinyl, piperazinyl, homopiperazinyl, or quinuclidinyl; where said morpholinyl, pyrrolidinyl, piperidinyl, piperazinyl, homopiperazinyl, or quinuclidinyl is optionally N-substituted with $C_1$-$C_4$ alkyl or optionally substituted aryl($C_1$-$C_4$ alkyl). In one variation, $R^{5'}$ is optionally substituted heterocyclylalkyl or optionally substituted aminoalkyl, including $R^6R^7N$—($C_2$-$C_4$ alkyl).

In another embodiment, compounds of formula (II) are described wherein A is selected from monosubstituted amido, disubstituted amido, and optionally substituted nitrogen-containing heterocyclylamido.

In one variation, A is a monosubstituted amido of the formula C(O)NHX—, where X is selected from alkyl, cycloalkyl, alkoxyalkyl, optionally substituted aryl, optionally substituted arylalkyl, heterocyclyl, heterocyclyl-($C_1$-$C_4$ alkyl), $R^6R^7N$—, and $R^6R^7N$—($C_2$-$C_4$ alkyl), where each heterocyclyl is independently selected.

In another variation, A is a disubstituted amido of the formula C(O)NR$^{14}$X—, where R$^{14}$ is selected from hydroxy, alkyl, alkoxycarbonyl, and benzyl; and X is selected from alkyl, cycloalkyl, alkoxyalkyl, optionally substituted aryl, optionally substituted arylalkyl, heterocyclyl, heterocyclyl-($C_1$-$C_4$ alkyl), $R^6R^7N$—, and $R^6R^7N$—($C_2$-$C_4$ alkyl), where each heterocyclyl is independently selected.

In another variation, A is an amide of an optionally substituted nitrogen-containing heterocycle attached at a nitrogen. Illustrative nitrogen-containing heterocycles include but are not limited to pyrrolidinyl, piperidinyl, piperazinyl, homopiperazinyl, triazolidinyl, triazinyl, oxazolidinyl, isoxazolidinyl, thiazolidinyl, isothiazolidinyl, 1,2-oxazinyl, 1,3-oxazinyl, morpholinyl, oxadiazolidinyl, and thiadiazolidinyl; each of which is optionally substituted. Such optional substitutions include the groups $R^{10}$, $R^{12}$, $R^6R^7N$—, and $R^6R^7N$—($C_1$-$C_4$ alkyl), as defined herein. In one embodiment, A is pyrrolidinonyl, piperidinonyl, 2-(pyrrolidin-1-ylmethyl)pyrrolidin-1-yl, or 1,2,3,4-tetrahydroisoquinolin-2-yl, each of which is optionally substituted, and attached at a nitrogen.

In another variation, A is an amide of an optionally substituted piperidinyl attached at the nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))—($C_2$-$C_4$ alkyl), $R^6R^7N$—, $R_6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A is piperidinyl substituted at the 4-position and attached at the nitrogen.

In another variation, A is an amide of an optionally substituted piperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))—($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A is piperazinyl substituted at the 4-position and attached at a nitrogen.

In another variation, A is an amide of an optionally substituted homopiperazinyl attached at a nitrogen. Illustrative optional substitutions include hydroxy, alkyl, cycloalkyl, alkoxy, alkoxycarbonyl, hydroxyalkyloxyalkyl, including (hydroxy($C_2$-$C_4$ alkyloxy))-($C_2$-$C_4$ alkyl), $R^6R^7N$—, $R^6R^7N$-alkyl, including $R^6R^7N$—($C_1$-$C_4$ alkyl), diphenylmethyl, optionally substituted aryl, optionally substituted aryl($C_1$-$C_4$ alkyl), and piperidin-1-yl($C_1$-$C_4$ alkyl). In one embodiment, A is homopiperazinyl substituted at the 4-position and attached at a nitrogen. In another embodiment, A is homopiperazinyl substituted at the 4-position with alkyl, aryl, aryl($C_1$-$C_4$ alkyl), and attached at a nitrogen.

In another variation, A is an amide of a heterocycle attached at a nitrogen, where the heterocycle is substituted with heterocyclyl, heterocyclylalkyl, cycloalkyl, cycloalkylalkyl, aryl, arylalkyl.

In another embodiment, A in formula (I) or (II) is an amide of an optionally substituted benzyl, optionally substituted 1-naphthylmethyl, or optionally substituted 2-naphthylmethyl amine. Optional substitutions include, but are not limited to, 2,3-dichloro, 2,5-dichloro, 2,5-dimethoxy, 2-trifluoromethyl, 2-fluoro-3-trifluoromethyl, 2-fluoro-5-trifluoromethyl, 2-methyl, 2-methoxy, 3,4-dichloro, 3,5-ditrifluoromethyl, 3,5-dichloro, 3,5-dimethyl, 3,5-difluoro, 3,5-dimethoxy, 3-bromo, 3-trifluoromethyl, 3-chloro-4-fluoro, 3-chloro, 3-fluoro-5-trifluoromethyl, 3-fluoro, 3-methyl, 3-nitro, 3-trifluoromethoxy, 3-methoxy, 3-phenyl, 4-trifluoromethyl, 4-chloro-3-trifluoromethyl, 4-fluoro-3-trifluoromethyl, 4-methyl, and the like.

In another embodiment, A in formula (I) or (II) is an amide of an optionally substituted benzyl-N-methylamine. In another embodiment, A in formula (I) or (II) is an amide of an optionally substituted benzyl-N-butylamine, including n-butyl, and t-butyl. In another embodiment, A in formula (I) or (II) is an amide of an optionally substituted benzyl-N-benzylamine. Optional substitutions include, but are not limited to, 2,3-dichloro, 3,5-dichloro, 3-bromo, 3-trifluoromethyl, 3-chloro, 3-methyl, and the like.

In another embodiment, A in formula (I) or (II) is an amide of an optionally substituted 1-phenylethyl, 2-phenylethyl, 2-phenylpropyl, or 1-phenylbenzylamine. In another embodiment, A in formula (I) or (I) is an amide of an optionally substituted 1-phenylethyl, 2-phenylethyl, 2-phenylpropyl, 1-phenylbenzylamine-N-methylamine. In another embodiment, A in formula (I) or (II) is an amide of an optionally substituted 2-phenyl-β-alanine, or derivative thereof, 1-phenylpropanolamine, and the like. Optional substitutions include, but are not limited to, 3-trifluoromethoxy, 3-methoxy, 3,5-dimethoxy, 2-methyl, and the like.

In another embodiment, A in formula (I) or (II) is an amide of an optionally substituted 1-phenylcyclopropyl, 1-phenylcyclopentyl, or 1-phenylcyclohexylamine. Optional substitutions include, but are not limited to, 3-fluoro, 4-methoxy, 4-methyl, 4 chloro, 2-fluoro, and the like.

In another embodiment, A in formula (I) or (II) is an amide of an optionally substituted heteroarylmethylamine, including but not limited to 2-furyl, 2-thienyl, 2-pyridyl, 3-pyridyl, 4-pyridyl, and the like. Optional substitutions include, but are not limited to, 5-methyl, 3-chloro, 2-methyl, and the like.

In another embodiment, A in formula (I) or (II) is an amide of a partially saturated bicyclic aryl, including but not limited to 1-, 2-, 4-, and 5-indanylamine, 1- and 2-tetrahydronaphthylamine, indolinyl, tetrahydroquinolinyl, tetrahydroisoquinolinyl, and the like, each of which is optionally substituted.

In another embodiment, A in formula (I) or (II) is an amide of a substituted piperidine or piperazine. Substituents on the piperidine or piperazine include heterocyclyl, heterocyclylalkyl, optionally substituted aryl, and optionally substituted arylalkyl. Illustrative piperidines and piperazines include the formulae:

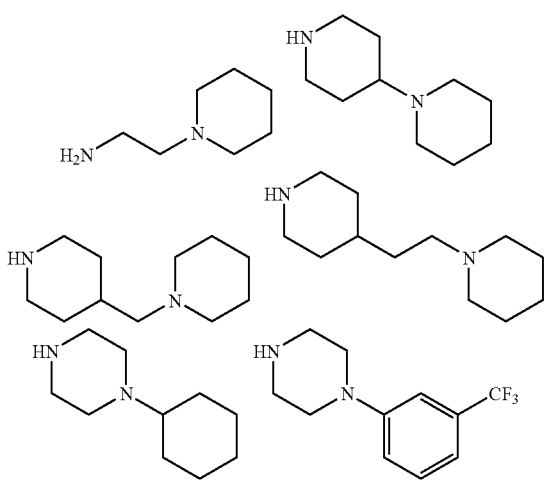

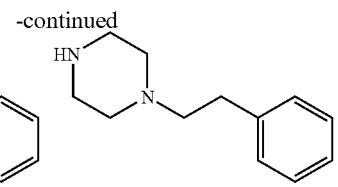

In another embodiment, A' in formula (I) is an amide of a substituted heterocycle attached at nitrogen. Substituents include alkyl, cycloalkyl, cycloalkylalkyl, heterocyclyl, heterocyclylalkyl, aryl, and arylalkyl. In one variation embodiment, A' in formula (I) is an amide of a heterocycle attached at nitrogen substituented with alkyl, cycloalkyl, cycloalkylalkyl, heterocyclyl, or heterocyclylalkyl.

In another embodiment, A' in formula (I) is an amide of an optionally substituted arylheterocyclylamine, arylalkylheterocyclylamine, heterocyclylalkylamine, or heteroarylalkylamine.

It is appreciated that in the foregoing illustrative examples of A and/or A' that include a chiral center, either of the optically pure enantiomers may be included in the compounds described herein; alternatively, the racemic form may be used. For example, either or both of the following enantiomers may be included in the compounds described herein (R)-1-(3-methoxyphenyl)ethylamine, (R)-1-(3-trifluoromethylphenyl)ethylamine, (R)-1,2,3,4-tetrahydro-1-naphtylamine, (R)-1-indanylamine, (R)-α,N-dimethylbenzylamine, (R)-amethylbenzylamine, (S)-1-(3-methoxyphenyl)ethylamine, (S)-1-(3-trifluoromethylphenyl)ethylamine, (S)-1,2,3,4-tetrahydro-1-naphtylamine, (S)-1-indanylamine, and (S)-ozmethylbenzylamine, and the like.

In another embodiment of the compounds of formula (II), Q is oxygen or sulfur. In another embodiment of the compounds of formula (II), R" is optionally substituted arylalkyl. In another embodiment of the compounds of formula (II), A is an amide of a substituted piperidine or piperazine.

In another embodiment of the compounds of formula (I), n is 1 or 2. In another embodiment of the compounds of formula (II), n is 1 or 2. In one variation of the compounds of formula (II), n is 1.

In another embodiment of the compounds of formulae (I) or (II), $R^2$ is hydrogen, alkyl, alkoxy, alkylthio, cyano, formyl, alkylcarbonyl, or a substituent selected from the group consisting of —$CO_2R^8$ and —$CONR^8R^{8'}$, where $R^8$ and $R^{8'}$ are each independently selected from hydrogen and alkyl.

In another embodiment of the compounds of formulae (I) or (II), $R^1$ is hydrogen. In another embodiment of the compounds of formulae (I) or (II), $R^1$ is methyl. In another embodiment of the compounds of formulae (I) or (II), $R^2$ is hydrogen. In another embodiment of the compounds of formulae (I) or (II), $R^2$ is methyl. In another embodiment of the compounds of formulae (I) or (II), both $R^1$ and $R^2$ are hydrogen.

In another embodiment of the compounds of formulae (I) or (II), $R^3$ is of the formulae:

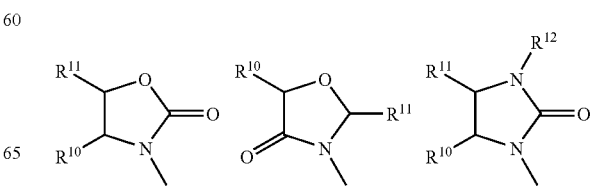

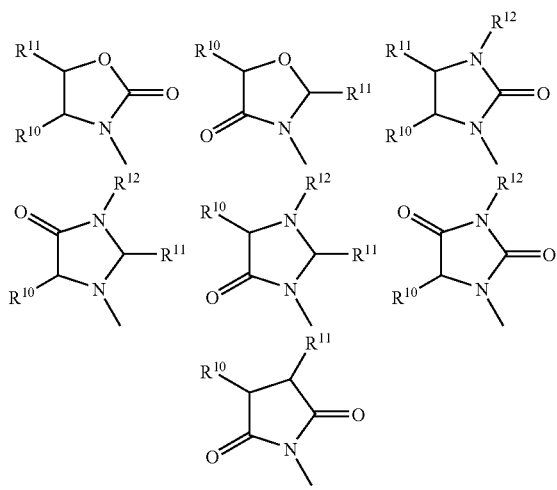

wherein $R^{10}$ and $R^{11}$ are each independently selected from hydrogen, optionally substituted alkyl, optionally substituted cycloalkyl, alkoxycarbonyl, alkylcarbonyloxy, optionally substituted aryl, optionally substituted arylalkyl, optionally substituted arylalkyloxy, optionally substituted arylalkylcarbonyloxy, diphenylmethoxy, triphenylmethoxy, and the like; and $R^{12}$ is selected from hydrogen, alkyl, cycloalkyl, alkoxycarbonyl, optionally substituted aryloxycarbonyl, optionally substituted arylalkyl, optionally substituted aryloyl, and the like.

In another embodiment of the compounds of formulae (I) or (II), $R^3$ is of the formulae:

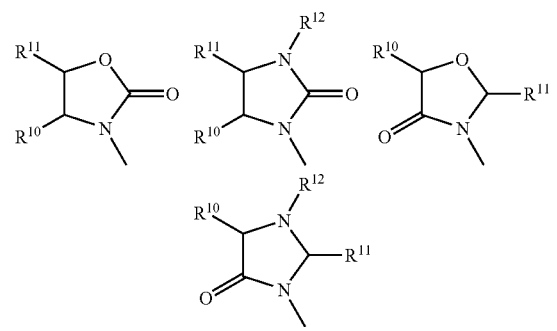

wherein $R^{10}$, $R^{11}$, and $R^{12}$ are as defined herein.

In another embodiment of the compounds of formulae (I) or (II), $R^3$ is of the formulae:

wherein $R^{10}$, $R^{11}$, and $R^{12}$ are as defined herein.

In another embodiment of the compounds of formulae (I) or (II), $R^3$ is of the formula:

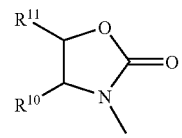

wherein $R^{10}$ and $R^{11}$ are as defined herein.

In another embodiment of the compounds of formulae (I) or (II), $R^4$ is of the formulae:

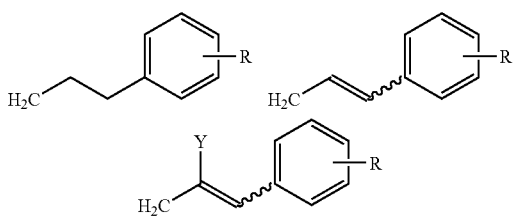

wherein Y an electron withdrawing group, such as halo, and R is hydrogen or an optional substitution, such as halo, alkyl, and alkoxy, including 2-methoxy. In one variation, Y is chloro.

It is appreciated that the compounds of formulae (I) and (II) are chiral at the α-carbon, except when A=A', and n=0. In one embodiment of the compounds of formula (I), when n is 1, the stereochemistry of the α-carbon is (S) or (R), or is an epimeric mixture. In another embodiment of the compounds of formula (I), when n is 1, the stereochemistry of the α-carbon is (R). In another embodiment of the compounds of formula (I), when n is 2, the stereochemistry of the α-carbon is (S). In one embodiment of the compounds of formula (II), when n is 1, the stereochemistry of the α-carbon is (R).

In another embodiment, compounds of formula (II) are described wherein $R^{5''}$ is optionally substituted aryl($C_2$-$C_4$ allyl).

The general chemical terms used in the formulae described herein have their usual ordinary meanings. For example, the term "allyl" refers to a straight-chain or optionally branched, saturated hydrocarbon, including but not limited to methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like. Further, it is to be understood that variations of the term alkyl are used in other terms, including but not limited to cycloalkyl, alkoxy, haloalkyl, alkanoyl, alkylene, and the like, and that such other terms also include straight-chain and optionally branched variations.

The term "aryl" refers to an aromatic ring or heteroaromatic ring and includes such groups as furyl, pyrrolyl, thienyl, pyridinyl, thiazolyl, oxazolyl, isoxazolyl, isothiazolyl, imidazolyl, pyrazolyl, phenyl, pyridazinyl, pyrimidinyl, pyrazinyl, thiadiazolyl, oxadiazolyl, naphthyl, indanyl, fluorenyl, quinolinyl, isoquinolinyl, benzodioxanyl, benzofuranyl, benzothienyl, and the like.

The term "optionally substituted" refers to the replacement of one or more, preferably from one to three, hydrogen atoms with one or more substitutents. Substituents include but are not limited to such groups as $C_1$-$C_4$ alkyl, $C_1$-$C_4$ alkoxy, $C_1$-$C_4$ alkylthio, hydroxy, nitro, halo, carboxy, cyano, $C_1$-$C_4$ haloalkyl, $C_1$-$C_4$ haloalkoxy, amino, carbamoyl, carboxamido, amino, alkylamino, dialkylamino, alkylalkylamino, $C_1$-$C_4$ alkylsulfonylamino, and the like. Such optional substitution may be made on alkyl, alkenyl, heterocyclyl, aryl, heteroaryl, and the like.

The term "heterocycle" refers to a non-aromatic cyclic structure possessing one or more heteroatoms, such as nitrogen, oxygen, sulfur, and the like, and includes such groups as tetrahydrofuryl, morpholinyl, pyrrolidinyl, piperidinyl, piperazinyl, homopiperazinyl, quinuclidinyl, and the like.

The term "acyl," refers to alkyl, alkenyl, aryl, and the like attached through a carbonyl group, and include such groups as formyl, acetyl, propanoyl, pivaloyl, pentanoyl, cyclohexanoyl, optionally substituted benzoyl, and the like.

The term "protected amino" refers to amine protected by a protecting group that may be used to protect the nitrogen, such as the nitrogen in the β-lactam ring, during preparation or subsequent reactions. Examples of such groups are benzyl, 4-methoxybenzyl, 4-methoxyphenyl, trialkylsilyl, for example trimethylsilyl, and the like.

The term "protected carboxy" refers to the carboxy group protected or blocked by a conventional protecting group commonly used for the temporary blocking of the acidic carboxy. Examples of such groups include lower alkyl, for example tert-butyl, halo-substituted lower alkyl, for example 2-iodoethyl and 2,2,2-trichloroethyl, benzyl and substituted benzyl, for example 4-methoxybenzyl and 4-nitrobenzyl, diphenylmethyl, alkenyl, for example allyl, trialkylsilyl, for example trimethylsilyl and tert-butyldiethylsilyl and like carboxy-protecting groups.

The term "antagonist," as used herein, refers to a full or partial antagonist. While a partial antagonist of any intrinsic activity may be useful, the partial antagonists illustratively show at least about 50% antagonist effect, or at least about 80% antagonist effect. The term also includes compounds that are full antagonists of one or more vasopressin receptors. It is appreciated that illustrative methods described herein require therapeutically effective amounts of vasopressin receptor antagonists; therefore, compounds exhibiting partial antagonism at one or more vasopressin receptors may be administered in higher doses to exhibit sufficient antagonist activity to inhibit the effects of vasopressin or a vasopressin agonist.

It is to be understood that in the embodiments described herein, an illustrative variation of alkyl is $C_1$-$C_6$ alkyl, such as methyl, ethyl, propyl, prop-2-yl, and the like; an illustrative variation of alkenyl is $C_2$-$C_6$ alkenyl, such as vinyl, allyl, and the like; an illustrative variation of alkynyl is $C_2$-$C_6$ allynyl, such as ethynyl, propynyl, and the like; an illustrative variation of alkoxy is $C_1$-$C_4$ alkoxy, such as methoxy, pent-3-oxy, and the like; an illustrative variation of alkylthio is $C_1$-$C_4$ alkylthio, such as ethylthio, 3-methylbuty-2-ylthio, and the like; an illustrative variation of alkylcarbonyl is $C_1$-$C_3$ alkylcarbonyl, such as acetyl, propanoyl, and the like; an illustrative variation of cycloalkyl is $C_3$-$C_8$ cycloalkyl; an illustrative variation of cycloalkenyl is $C_3$-$C_9$ cycloalkenyl, such as limonenyl, pinenyl, and the like; an illustrative variation of optionally substituted arylalkyl is optionally substituted aryl($C_1$-$C_4$ alkyl); an illustrative variation of optionally substituted arylalkenyl is optionally substituted aryl($C_2$-$C_4$ alkenyl); an illustrative variation of optionally substituted arylalkynyl is optionally substituted aryl($C_2$-$C_4$ alkynyl); an illustrative variation of alkoxyalkyl is ($C_1$-$C_4$ alkoxy)-($C_1$-$C_4$ alkyl); an illustrative variation of optionally substituted heteroarylalkyl is optionally substituted heteroaryl($C_1$-$C_4$ alkyl); and an illustrative variation of alkoxycarbonyl is $C_1$-$C_4$ alkoxycarbonyl.

It is also to be understood that each of the foregoing embodiments, variations, and aspects of the compounds described herein may be combined in each and every way. For example, compounds where $R^3$ is optionally substituted oxazolidinonyl, and $R^4$ is optionally substituted arylalkenyl are contemplated herein. Further, compounds where $R^3$ is optionally substituted oxazolidinonyl, $R^4$ is optionally substituted arylalkenyl, and both $R^1$ and $R^2$ are hydrogen are contemplated herein. Further, compounds where $R^3$ is optionally substituted oxazolidinonyl, $R^4$ is optionally substituted arylalkenyl, both $R^1$ and $R^2$ are hydrogen, and both A and A' are independently selected amides are contemplated herein.

In another embodiment, compounds of the following formula are described:

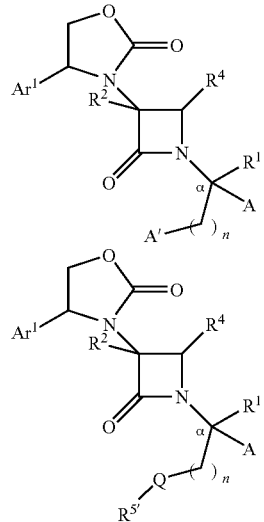

where $R^1$, $R^2$, $R^4$, A, A', Q, and R5" are as defined herein, and $Ar^1$ is an optionally substituted aryl group.

In another embodiment, compounds of the following formula are described:

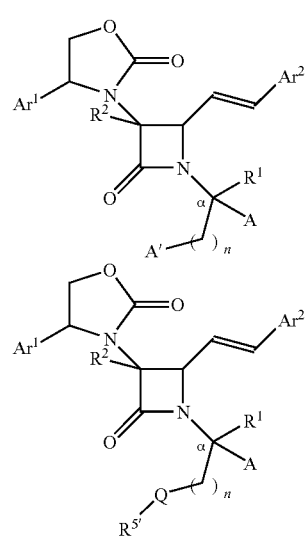

where $R^1$, $R^2$, A, A', Q, and R5" are as defined above, and $Ar^1$ and $Ar^2$ are each an optionally substituted aryl group, each independently selected.

In another illustrative embodiment, compounds of the following formula are described:

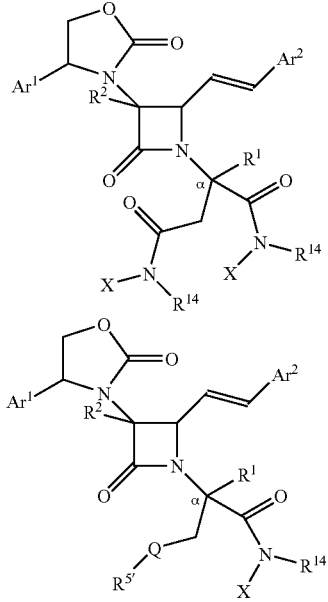

wherein $R^1$, $R^2$, Q, and R5" are defined herein, $Ar^1$ and $Ar^2$ are optionally substituted aryl or heteroaryl groups, X is independently selected in each instance, and is as defined herein, and $R^{14}$ is independently selected in each instance, and is as defined herein, or is hydrogen. In one illustrative aspect, $Ar^1$ and $Ar^2$ are each an independently selected optionally substituted phenyl. In another illustrative aspect, $R^1$ and $R^2$ are each hydrogen.

In another embodiment, compounds of the following formula are described:

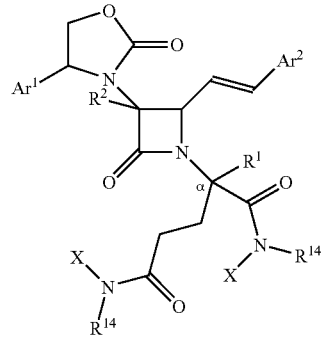

wherein $Ar^1$ and $Ar^2$ are optionally substituted aryl or heteroaryl groups, $R^1$ and $R^2$ are defined herein, X is independently selected in each instance, and is as defined herein, and $R^{14}$ is independently selected in each instance, and is as defined herein, or is hydrogen. In one illustrative aspect, $Ar^1$ and $Ar^2$ are each an independently selected optionally substituted phenyl. In another illustrative aspect, $R^1$ and $R^2$ are each hydrogen.

The compounds described herein possess an azetidinone core structure that includes asymmetric carbon atoms at C(3) and C(4), creating four stereoisomeric configurations, as illustrated by the following formulae:

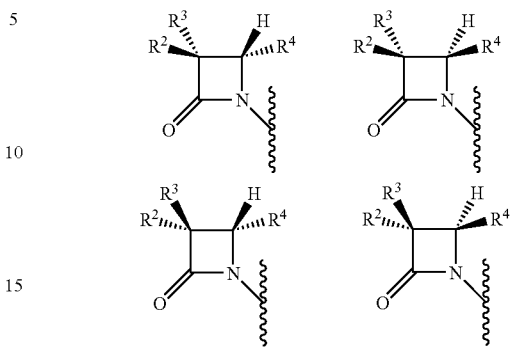

The compounds described herein may, therefore, exist as single diastereomers, as racemic mixtures, or as mixtures of various diastereomers. It is appreciated that in some applications, certain stereoisomers or mixtures of stereoisomers may be included in the various embodiments of the invention, while in other applications, other stereoisomers or mixtures of stereoisomers may be included. One illustrative mixture is a racemic mixture of two isomers that is substantially or completely free of any other diastereomers. In other applications, a single stereoisomer may be included in the various embodiments of the invention. In one aspect, certain chiral centers are stereochemically pure in the compounds described herein, such as for example a single enantiomer of the azetidinone core structure corresponding to the (3S,4R)-diastereomeric configuration is described. In one variation, other chiral centers included in the compounds of this embodiment are epimeric, such that equal amounts of each stereo configuration are present. In another variation, some or all other chiral centers in the compound are optically pure.

It is also understood that the α-carbon bearing $R^1$ is also chiral. Further, the radicals selected for groups such as $R^1$, $R^2$, $R^3$, $R^4$, A, A', may also include chiral centers. For example, when $R^3$ is 4-substituted oxazolidin-2-on-3-yl, the 4-position of the oxazolidinone ring is asymmetric. In addition, when $R^3$ is 2,5-disubstituted oxazolidin-4-on-3-yl or 1,2,5-trisubstituted imidazolidin-4-on-3-yl, the 2- and 5-carbons of the imidazolidinone rings are each asymmetric. Finally, when $R^3$ is succinimido and one of $R^{10}$ and $R^{11}$ is hydrogen, the carbon bearing the non-hydrogen substituent is also asymmetric. Therefore, it is to be understood that the various formulae described herein may represent each single diastereomer, various racemic mixtures, and various other mixtures of enantiomers and/or diastereomers collectively. While compounds possessing all combinations of stereochemical purity are contemplated by the present description, it is nonetheless appreciated that in many cases the desired vasopressin antagonist activity may reside in a subset of all possible diastereomers, or even in a single diasteromer. In one illustrative embodiment, the compounds described herein are a diastereomeric mixture of the (αR,3S,4R) and (αS,3S,4R) absolute configurations. In another illustrative embodiment, the compounds described herein have substantially or only the (αR,3S,4R) absolute configuration. In another illustrative embodiment, the compounds described herein have substantially or only the (αS,3S,4R) absolute configuration.

It is understood that the above general formulae represent a minimum of 8 different stereoisomeric configurations. It is appreciated that certain stereoisomers may be more biologically active than others. Therefore, the above formula contemplates herein all possible stereoisomers, as well as various mixtures of each stereoisomer. Illustratively, the following pair of diastereomers at C(α) is described:

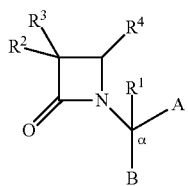

where the stereochemistry at the "α" carbon is either (R) or (S). In one aspect, the stereochemistry at the "α" carbon is only (R), while in another aspect, the stereochemistry at the "α" carbon is only (S).

The compounds described herein may also prepared as or converted to pharmaceutically acceptable salt derivatives. Illustrative pharmaceutically acceptable salts of compounds described herein that have a basic amino group include, but are not limited to, salts of inorganic and organic acids. Illustrative inorganic acids include hydrochloric acid, hydrobromic acid, hydroiodic acid, sulfuric acid, phosphoric acid, and the like. Illustrative organic acids include p-toluenesulfonic acid, methanesulfonic acid, oxalic acid, p-bromophenylsulfonic acid, carbonic acid, succinic acid, citric acid, benzoic acid, acetic acid, and the like. Illustrative examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. In one embodiment, pharmaceutically acceptable salts are those formed with hydrochloric acid, trifluoroacetic acid, maleic acid or fumaric acid.

In another embodiment, methods for treating one or more premenstrual disorders are described herein. The methods include the step of administering one or more of the β-lactamyl alkanoic acid vasopressin $V_{1a}$ receptor antagonists described herein, including pharmaceutically acceptable salts thereof, to a patient in need of relief from such premenstrual disorders. The one or more β-lactamyl alkanoic acid vasopressin $V_{1a}$ receptor antagonists and/or pharmaceutically acceptable salts thereof may be included in a pharmaceutical composition, such as those described herein. Antagonism of the vasopressin $V_{1a}$ receptor has been shown to alleviate or prevent the symptoms of premenstrual dysmenorrhoea dysphoria (PMDD) and primary dysmenorrhoea (PD). See generally, Brouard et al, in British Journal of Obstetrics and Gynecology 107:614-19 (2000). The one or more compounds, or pharmaceutical compositions thereof, are illustratively given shortly before the onset of menstruation as a preventative treatment of a Premenstrual Syndrome (PMS), disorder, duysfunction, and/or dysmenorrhoea. It has been reported that the orally active $V_{1a}$ antagonist SR49059 showed a significant reduction in pain across three menstrual cycles in subjects 18-35 years.

In one embodiment, methods are described for treating premenstrual disorders including primary dysmenorrhoea (PD), also referred to as premenstrual (PMD). Primary dysmenorrhoea (PD) includes symptoms associated with the onset of menses, such as lower back pain, pelvic cramping, uterine pain, fluid retention, such as bloating, and the like. The method includes the step of administering an effective amount of a compound described herein, either alone, or as a pharmaceutical composition. It is appreciated that compounds described herein that are selectively, or preferentially active at peripheral vasopressin receptors are advantageously included in such methods.

In another embodiment, methods are described for treating premenstrual disorders including premenstrual dysmenorrhoea dysphoria (PMDD). Premenstrual dysmenorrhoea dysphoria (PMDD) includes many of the symptoms observed in PD, and also may include secondary stress. PMDD may be treated as a depressive disorder. The method includes the step of administering an effective amount of a compound described herein, either alone, or as a pharmaceutical composition. It is appreciated that compounds described herein that are capable of crossing the blood-brain-barrier are advantageously included in such methods.

In another embodiment, pharmaceutical compositions containing one or more β-lactamyl alkanoic acid vasopressin receptor antagonists are described herein. The pharmaceutical compositions include one or more carriers, diluents, and or excipients.

The compounds described herein may be administered directly or as part of a pharmaceutical composition that includes one or more carriers, diluents, and/or excipients. Such formulations may include one or more than one of the compounds described herein. Such pharmaceutical compositions may be administered by a wide variety of conventional routes in a wide variety of dosage formats, including but not limited to oral, rectal, transdermal, buccal, parenteral, subcutaneous, intravenous, intramuscular, intranasal, and the like. See generally, Remington's Pharmaceutical Sciences, (16th ed. 1980).

In making the compositions of the compounds described herein, the active ingredient may be mixed with an excipient, diluted by an excipient, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art. It is appreciated that the carriers, diluents, and excipients used to prepare the compositions described herein are advantageously GRAS (Generally Regarded as Safe) compounds.

Compounds described herein that are powders may be milled to desirable particle sizes and particle size ranges for emulsion and/or solid dosage forms. Illustrative particle size ranges include particle sizes of less than 200 mesh, particle sizes of less than 40 mesh, and the like.

It is to be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms. Therefore the dosage ranges described herein are intended to be illustrative and should not be interpreted to limit the invention in any way. In cases where the dose is at the upper boundaries of the ranges described herein, the dose may be formatted as divided doses for administration at predetermined time points throughout the day. In cases where the dose is at the lower boundaries of the ranges described herein, the dose may be formatted as a single dose for administration at predetermined time points once a day. The term "unit dosage form" refers to physically discrete units suitable as unitary dosages for human subjects and other mammals, each unit containing a predetermined quantity of active material calculated to produce the desired therapeutic effect over a predetermined time frame, in combination with a pharmaceutically acceptable carrier, and optionally in association with a suitable pharmaceutical diluent and/or excipient.

In one illustrative embodiment, single or total divided dosages per day fall within the range from about 11 g/kg to about 100 mg/kg of body weight of the patient being treated. In another illustrative embodiment single or total divided dosages per day fall within the range from about 25 µg/kg to about 25 mg/kg of body weight of the patient being treated. It is appreciated that compounds of formula (I) may be advantageously administered at slightly higher overall daily totals, such as in the range from about 5 µg/kg to about 100 mg/kg of body weight, in the range from about 25 µg/kg to about 25 mg/kg of body weight, or in the range from about 25 µg/kg to about 5 mg/kg of body weight. It is further appreciated that compounds of formula (II) may be advantageously administered at slightly lower overall daily totals, such as in the range from about 1 µg/kg to about 50 mg/kg of body weight, in the range from about 5 µg/kg to about 25 mg/kg of body weight, or in the range from about 5 µg/kg to about 5 mg/kg of body weight. It is appreciated that the vitro binding and functional antagonism of activity at $V_{1a}$ vasopressin receptors of the compounds described herein is relative to the efficacious unit dose to be administered.

The following preparations and examples further illustrate the synthesis of the compounds of this invention and are not intended to limit the scope of the invention in any way. Unless otherwise indicated, all reactions were performed at ambient temperature, and all evaporations were performed its vacuo. All of the compounds described below were characterized by standard analytical techniques, including nuclear magnetic resonance spectroscopy ($^1$H NMR) and mass spectral analysis (MS). Other examples may be prepared by the synthetic routes and processes described herein and exemplified below. Additional details for the synthetic procedures are described in WO 03/031407, the disclosure of which is incorporated herein by reference.

EXAMPLES

Compound Examples

Example 1

(4(S)-phenyloxazolidin-2-on-3-yl)acetyl chloride. A solution of 1.0 equivalent of (4(S)-phenyloxazolidin-2-on-3-yl) acetic acid (Evans, U.S. Pat. No. 4,665,171) and 1.3 equivalent of oxalyl chloride in 200 mL dichloromethane was treated with a catalytic amount of anhydrous dimethylformamide (85 µL/milliequivalent of acetic acid derivative) resulting in vigorous gas evolution. After 45 minutes all gas evolution had ceased and the reaction mixture was concentrated under reduced pressure to provide the title compound as an off-white solid after drying for 2 h under vacuum.

Example 1A (4(R)-phenyloxazolidin-2-on-3-yl)acetyl chloride. Example 1A was prepared following the procedure of Example 1, except that (4(R)-phenyloxazolidin-2-on-3-yl) acetic acid was used instead of (4(S)-phenyloxazolidin-2-on-3-yl)acetic acid (see, Evans & Sjogren, Tetrahedron Lett. 26:3783 (1985)).

Example 1B

Methyl (4(S)-phenyloxazolidin-2-on-3-yl)acetate. A solution of (4(S)-phenyloxazolidin-2-on-3-yl)acetic acid (1 g, 4.52 mmol) (prepared according to Evans in U.S. Pat. No. 4,665,171) in 20 mL of anhydrous methanol was treated hourly with 5 equivalents of acetyl chloride, for a total of 20 equivalents. The resulting solution was stirred overnight. The residue obtained after evaporation of the MeOH was redissolved in 30 mL of $CH_2Cl_2$ and treated with 50 mL of saturated aqueous $Na_2CO_3$. The organic layer was evaporated and dried ($MgSO_4$) to yield the title compound as a colorless oil (1.001 g, 94%/0); $^1$H NMR ($CDCl_3$) δ 3.37 (d, J=18.0 Hz, 1H), 3.69 (s, 3H), 4.13 (t, J=8.3 Hz, 1H), 4.28 (d, J=18.0 Hz, 1H), 4.69 (t, J=8.8 Hz, 1H), 5.04 (t, J=8.4 Hz, 1H), 7.26-7.29 (m, 2H), 7.36-7.42 (m, 3H).

Example 1C

Methyl 2-(4(S)-phenyloxazolidin-2-on-3-yl)propanoate. A solution of methyl (4(S)-phenyloxazolidin-2-on-3-yl)acetate (1 g, 4.25 mmol) in 10 mL of anhydrous THF at −78° C. was treated with 4.68 mL (4.68 mmol) of a 1 M solution of lithium bis(trimethylsilyl)amide in THF. The reaction mixture was stirred for 1 h. at about −70° C. before adding MeI (1.59 mL, 25.51 mmol). Upon complete conversion of the azetidinone, the reaction was quenched with saturated aqueous $NH_4Cl$ and partitioned between EtOAc and water. The organic layer was washed sequentially with saturated aqueous sodium bisulfite, and saturated aqueous NaCl. The resulting organic layer was dried ($MgSO_4$) and evaporated to afford the title compound (a mixture of diasteromers) as a white solid (1.06 g, 93%); $^1$H NMR ($CDCl_3$) δ 1.07/1.53 (d/d, J=7.5 Hz, 3H), 3.59/3.74 (s/s, 3H), 3.85/4.48 (q/q, J=7.5 Hz, 1H), 4.10-4.14 (m, 1H), 4.60-4.64/4.65-4.69 (m/m, 1H), 4.88-4.92/4.98-5.02 (m/m, 1H), 7.24-7.40 (m, 5H).

Example 1D 2-(4(S)-Phenyloxazolidin-2-on-3-yl)propanoic acid. To a solution of methyl 2-(4(S)-phenyloxazolidin-2-on-3-yl)propanoate (1 g, 4.01 mmol) in 35 mL of MeOH was added, at 0° C., 14.3 mL (12.04 mmol) of a 0.84 M solution of LiOH in water. The reaction mixture was then stirred for 3 h. at ambient temperature. Upon complete hydrolysis of the azetidinone, the MeOH was removed by evaporation, the crude residue dissolved in $CH_2Cl_2$ and treated with saturated aqueous NaCl. The resulting organic layer was dried ($MgSO_4$) and evaporated to afford the title compound (racemic mixture) as a white solid (0.906 g, 96%); $^1$H NMR ($CDCl_3$) δ 1.13/1.57 (d/d, J=7.5 Hz, 3H), 3.75/4.50 (q/q, J=7.5 Hz, 1H), 4.10-4.16 (m, 1H), 4.62-4.72 (m, 1H), 4.92-5.03 (m, 1H), 7.32-7.43 (m, 5H).

Example 1E 2-(4(S)-Phenyloxazolidin-2-on-3-yl)propanoyl chloride. A solution of 1 equivalent of Example 1D and 1.3 equivalent of oxalyl chloride in 200 mL $CH_2Cl_2$ (150 mL/g of propanoic acid derivative) was treated with a catalytic amount of anhydrous DMF (85 μL/mmole of propanoic acid derivative) resulting in vigorous gas evolution. After 45 min., all gas evolution had ceased and the reaction mixture was concentrated under reduced pressure to provide the title compound as an off-white solid after drying for 2 h. under vacuum.

Example 2

General procedure for amide formation from an activated ester derivative. N-Benzyloxycarbonyl-L-aspartic acid β-t-butyl ester α-(3-trifluoromethyl)benzylamide. A solution of N-benzyloxycarbonyl-L-aspartic acid β-t-butyl ester α-N-hydroxysuccinimide ester (1.95 g, 4.64 mmol, Advanced ChemTech) in 20 mL of dry tetrahydrofuran was treated with 0.68 mL (4.74 mmol) of 3-(trifluoromethyl)benzyl amine. Upon completion (TLC, 60:40 hexanes/ethyl acetate), the mixture was evaporated, and the resulting oil was partitioned between dichloromethane and a saturated aqueous solution of sodium bicarbonate. The organic layer was evaporated to give 2.23 g (quantitative yield) of the title compound as a white solid; $^1$H NMR ($CDCl_3$) δ 1.39 (s, 9H), 2.61 (dd, J=6.5 Hz, J=17.2 Hz, 1H), 2.98 (dd, J=3.7 Hz, J=17.0 Hz, 1H), 4.41 (dd, J=5.9 Hz, J=15.3 Hz, 1H), 4.50-4.57 (m, 2H), 5.15 (s, 2H), 5.96-5.99 (m, 1H), 6.95 (s, 1H), 7.29-7.34 (m, 5H), 7.39-7.43 (m, 2H), 7.48-7.52 (m, 2H).

Examples 2A-2C and 3-5 were prepared according to the procedure of Example 2, except that N-benzyloxycarbonyl-L-aspartic acid β-t-butyl ester α-N-hydroxysuccinimide ester was replaced by the appropriate amino acid derivative, and 3-(trifluoromethyl)benzyl amine was replaced with the appropriate amine.

Example 2A

N-Benzyloxycarbonyl-L-aspartic acid β-t-butyl ester α-[4-(2-phenylethyl)]piperazinamide. N-benzyloxycarbonyl-L-aspartic acid β-t-butyl ester α-N-hydroxysuccinimide ester (5.0 g, 12 mmol, Advanced ChemTech) and 4-(phenylethyl)piperazine 2.27 mL (11.9 mmol) gave 5.89 g (quantitative yield) of the title compound as an off-white oil; $^1$H NMR ($CDCl_3$) δ 1.40 (s, 9H), 2.45-2.80 (m, 10H), 3.50-3.80 (m, 4H), 4.87-4.91 (m, 1H), 5.08 (s, 2H), 5.62-5.66 (m, 1H), 7.17-7.33 (m, 10H).

Example 2B

N-Benzyloxycarbonyl-L-glutamic acid γ-t-butyl ester α-(3-trifluoromethyl)benzylamide. N-benzyloxycarbonyl-L-glutamic acid β-t-butyl ester α-N-hydroxysuccinimide ester (4.83 g, 11.1 mmol, Advanced ChemTech) and 3-(trifluoromethyl)benzylamine) 1.63 mL (11.4 mmol) gave 5.41 g (98%) of the title compound as an off-white solid; $^1$H NMR ($CDCl_3$) δ 1.40 (s, 9H), 1.88-1.99 (m, 1H), 2.03-2.13 (m, 1H), 2.23-2.33 (m, 1H), 2.38-2.47 (m, 1H), 4.19-4.25 (s, 1H), 4.46-4.48 (m, 2H), 5.05-5.08 (m, 2H), 5.67-5.72 (m, 1H), 7.27-7.34 (m, 5H), 7.39-7.43 (m, 2H), 7.48-7.52 (m, 2H).

Example 2C

N-Benzyloxycarbonyl-L-glutamic acid γ-t-butyl ester α-[4-(2-phenylethyl)]piperazinamide. N-benzyloxycarbonyl-L-glutamic acid γ-t-butyl ester α-N-hydroxysuccinimide ester (5.0 g, 12 mmol, Advanced ChemTech) and 4-(phenylethyl)piperazine 2.19 mL (11.5 mmol) gave 5.87 g (quantitative yield) of the title compound as an off-white oil; $^1$H NMR ($CDCl_3$) δ 1.43 (s, 9H); 1.64-1.73 (m, 1H); 1.93-2.01 (m, 1); 2.23-2.40 (m, 2H); 2.42-2.68 (m, 6H); 2.75-2.85 (m, 2H); 3.61-3.74 (m, 4H); 4.66-4.73 (m, 1H); 5.03-5.12 (m, 2H); 5.69-5.72 (m, 1H); 7.16-7.34 (m, 10H).

Example 3

N-Benzyloxycarbonyl-L-aspartic acid β-t-butyl ester α-[4-(2-phenylethyl)]piperazinamide. N-benzyloxycarbonyl-L-aspartic acid 3-t-butyl ester α-N-hydroxysuccinimide ester (5.0 g, 12 mmol, Advanced ChemTech) and 4-(phenylethyl)piperazine 2.27 mL (11.9 mmol) gave 5.89 g (quantitative yield) of the title compound as an off-white oil; $^1$H NMR ($CDCl_3$) δ 1.40 (s, 9H), 2.45-2.80 (m, 10H), 3.50-3.80 (m, 4H), 4.87-4.91 (m, 1H), 5.08 (s, 2H), 5.62-5.66 (m, 1H), 7.17-7.33 (m, 10H).

Example 4

N-Benzyloxycarbonyl-L-glutamic acid γ-t-butyl ester α-(3-trifluoromethyl)benzylamide. N-benzyloxycarbonyl-L-glutamic acid β-t-butyl ester α-N-hydroxysuccinimide ester (4.83 g, 11.1 mmol, Advanced ChemTech) and 3-(trifluoromethyl)benzylamine) 1.63 mL (11.4 mmol) gave 5.41 g (98%) of the title compound as an off-white solid; $^1$H NMR ($CDCl_3$) δ 1.40 (s, 9H), 1.88-1.99 (m, 1H), 2.03-2.13 (m, 1H), 2.23-2.33 (m, 1H), 2.38-2.47 (m, 1H), 4.19-4.25 (s, 1H), 4.46-4.48 (m, 2H), 5.05-5.08 (m, 2H), 5.67-5.72 (m, 1H), 7.27-7.34 (m, 5H), 7.39-7.43 (m, 2H), 7.48-7.52 (m, 2H).

Example 5

N-Benzyloxycarbonyl-L-glutamic acid γ-t-butyl ester α-[4-(2-phenylethyl)]piperazinamide. N-benzyloxycarbonyl-L-glutamic acid γ-t-butyl ester α-N-hydroxysuccinimide ester (5.0 g, 12 mmol, Advanced ChemTech) and 4-(phenylethyl)piperazine 2.19 mL (11.5 mmol) gave 5.87 g (quantitative yield) of the title compound as an off-white oil; $^1$H NMR ($CDCl_3$) δ 1.43 (s, 9H); 1.64-1.73 (m, 1H); 1.93-2.01 (m, 11H); 2.23-2.40 (m, 2H); 2.42-2.68 (m, 6H); 2.75-2.85

(m, 2H); 3.61-3.74 (m, 4H); 4.66-4.73 (m, 1H); 5.03-5.12 (m, 2H); 5.69-5.72 (m, 1H); 7.16-7.34 (m, 10H).

Example 5A

N-[(9H-Fluoren-9-yl)methoxycarbonyl]-O-(benzyl)-D-serine t-Butyl ester. N-[(9H-Fluoren-9-yl)methoxycarbonyl]-O-(benzyl)-D-serine (0.710 g, 1.70 mmole) in dichloromethane (8 mL) was treated with t-butyl acetate (3 mL) and concentrated sulfuric acid (40 µL) in a sealed flask at 0° C. Upon completion (TLC), the reaction was quenched with of dichloromethane (10 mL) and saturated aqueous potassium bicarbonate (15 mL). The organic layer was washed with distilled water, and evaporated. The resulting residue was purified by flash column chromatography (98:2 dichloromethane/methanol) to yield the title compound as a colorless oil (0.292 g, 77%); $^1$H NMR (CDCl$_3$) δ 1.44 (s, 9H); 3.68 (dd, J=2.9 Hz, J=9.3 Hz, 1H); 3.87 (dd, J=2.9 Hz, J=9.3 Hz, 1H); 4.22 (t, J=7.1 Hz, 1H); 4.30-4.60 (m, 5H); 5.64-5.67 (m, 1H); 7.25-7.39 (m, 9H); 7.58-7.61 (m, 2H); 7.73-7.76 (m, 2H).

Example 5B

O-(Benzyl)-D-serine t-Butyl ester. Example 5A (0.620 g, 1.31 mmol) in dichloromethane (5 mL) was treated with tris(2-aminoethyl)amine (2.75 mL) for 5 h. The resulting mixture was washed twice with a phosphate buffer (pH=5.5), once with saturated aqueous potassium bicarbonate, and evaporated to give 0.329 g (quantitative yield) of the title compound as an off-white solid; $^1$H NMR (CD$_3$OD) δ 1.44 (s, 9H); 3.48 (dd, J=J'=4.2 Hz, 1H); 3.61 (dd, J=4.0 Hz, J=9.2 Hz, 1H); 3.72 (dd, J=4.6 Hz, J=9.2 Hz, 1H); 4.47 (d, J=12.0 Hz, 1H); 4.55 (d, J=12.0 Hz, 1H); 7.26-7.33 (m, 5H).

Example 6

General procedure for amide formation from a carboxylic acid. N-Benzyloxycarbonyl-D-aspartic acid β-t-butyl ester α-(3-trifluoromethyl)benzylamide. A solution of 1 g (2.93 mmol) of N-benzyloxycarbonyl-D-aspartic acid β-t-butyl ester monohydrate (Novabiochem) in 3-4 mL of dichloromethane was treated by sequential addition of 0.46 mL (3.21 mmol) of 3-(trifluoromethyl)benzylamine, 0.44 g (3.23 mmol) of 1-hydroxy-7-benzotriazole, and 0.62 g (3.23 mmol) of 1-[3-(dimethylamino)propyl]-3-ethylcarbodiimide hydrochloride. After at least 12 hours at ambient temperature or until complete as determined by thin layer chromatography (95:5 dichloromethane/methanol eluent), the reaction mixture was washed sequentially with a saturated aqueous sodium bicarbonate solution and with distilled water. The organic layer was evaporated to give 1.41 g (quantitative yield) of the title compound as an off-white solid; $^1$H NMR (CDCl$_3$) δ 1.39 (s, 9H); 2.61 (dd, J=6.5 Hz, J=17.2 Hz, 1H); 2.98 (dd, J=4.2 Hz, J=17.2 Hz, 1H); 4.41 (dd, J=5.9 Hz, J=15.3 Hz, 1H); 4.50-4.57 (m, 2H); 5.10 (s, 2H); 5.96-6.01 (m, 1H); 6.91-7.00 (m, 1H); 7.30-7.36 (m, 5H); 7.39-7.43 (m, 2H); 7.48-7.52 (m, 2H).

Examples 7-7H were prepared according to the procedure of Example 6, except that N-benzyloxycarbonyl-D-aspartic acid β-t-butyl ester monohydrate was replaced by the appropriate amino acid derivative, and 3-(trifluoromethyl)benzyl amine was replaced with the appropriate amine.

Example 7

N-Benzyloxycarbonyl-D-glutamic acid γ-t-butyl ester α-(3-trifluoromethyl)benzylamide. N-benzyloxycarbonyl-D-glutamic acid γ-t-butyl ester (1.14 g, 3.37 mmol) and 0.53 mL (3.70 mmol, Novabiochem) of 3-(trifluoromethyl)benzylamine gave 1.67 g (quantitative yield) of Example 7 as an off-white solid. Example 7 exhibited an $^1$H NMR spectrum consistent with the assigned structure.

Example 7A

N-Benzyloxycarbonyl-L-glutamic acid α-t-butyl ester γ-(4-cyclohexyl)piperazinamide. N-benzyloxycarbonyl-L-glutamic acid α-t-butyl ester (1.36 g, 4.03 mmol) and 0.746 g (4.43 mmol) of 1-cyclohexylpiperazine gave 1.93 g (98%) of Example 7A as an off-white solid; $^1$H NMR (CDCl$_3$) δ 1.02-1.12 (m, 5H); 1.43 (s, 9H), 1.60-1.64 (m, 1H); 1.80-1.93 (m, 5H); 2.18-2.52 (m, 8H); 3.38-3.60 (m, 4H); 4.20-4.24 (m, 1H); 5.03-5.13 (m, 2H); 5.53-5.57 (m, 1H); 7.28-7.34 (m, 5H).

Example 7B

N-Benzyloxycarbonyl-D-aspartic acid β-t-butyl ester α-(2-fluoro-3-trifluoromethyl)benzylamide. N-benzyloxycarbonyl-D-aspartic acid β-t-butyl ester monohydrate (Novabiochem) (0.25 g, 0.73 mmol) and 0.12 mL of (2-fluoro-3-trifluoromethyl)benzylamine gave 0.365 g (quantitative yield) of Example 7B as an off-white solid; $^1$H NMR (CDCl$_3$) δ 1.38 (s, 9H); 2.59 (dd, J=6.5 Hz, J=17.0 Hz, 1H); 2.95 (dd, J=4.3 Hz, J=17.0 Hz, 1H); 4.46-4.56 (m, 3H); 5.11 (s, 2H); 5.94-5.96 (m, 1H); 7.15 (t, J=8.0 Hz, 1H); 7.30-7.36 (m, 5H); 7.47-7.52 (m, 2H).

Example 7C

N-Benzyloxycarbonyl-D-aspartic acid β-t-butyl ester α-[(S)-α-methylbenzyl]amide. N-benzyloxycarbonyl-D-aspartic acid β-t-butyl ester monohydrate (Novabiochem) (0.25 g, 0.73 mmol) and 0.094 mL of (S)-α-methylbenzylamine gave 0.281 g (90%) of Example 7C as an off-white solid; $^1$H NMR (CDCl$_3$) δ 1.41 (s, 9H); 1.44 (d, J=7.0 Hz, 3H); 2.61 (dd, J=7.0 Hz, J=17.0 Hz, 1H); 2.93 (dd, J=4.0 Hz, J=17.5 Hz, 1H); 4.50-4.54 (m, 1H); 5.04-5.14 (m, 3H); 5.94-5.96 (m, 1H); 6.76-6.80 (m, 1H); 7.21-7.37 (m, 10H).

Example 7D

N-Benzyloxycarbonyl-D-aspartic acid β-t-butyl ester α-[(R)-α-methylbenzyl]amide. N-benzyloxycarbonyl-D-aspartic acid β-t-butyl ester monohydrate (Novabiochem) (0.25 g, 0.73 mmol) and 0.094 mL of (R)-α-methylbenzylamine gave 0.281 g (90%) of Example 7D as an off-white solid; $^1$H NMR (CDCl$_3$) δ 1.38 (s, 9H); 1.43 (d, J=6.9 Hz, 3H); 2.54 (dd, J=7.3 Hz, J=17.2 Hz, 1H); 2.87 (dd, J=4.1 Hz, J=17.3 Hz, 1H); 4.46-4.50 (m, 1H); 4.99-5.15 (m, 3H); 5.92-5.96 (m, 1H); 6.78-6.82 (m, 1H); 7.21-7.33 (m, 10H).

Example 7E

N-Benzyloxycarbonyl-D-aspartic acid γ-t-butyl ester α-[N-methyl-N-(3-trifluoromethylbenzyl)]amide. N-benzyloxycarbonyl-D-aspartic acid γ-t-butyl ester (0.303 g, 0.89 mmol, Novabiochem) and 0.168 g (0.89 mmol,) of N-methyl-N-(3-trifluoromethylbenzyl)amine gave 0.287 g (65%) of Example 7E as an off-white solid; $^1$H NMR (CDCl$_3$) δ 1.40 (s, 9H); 2.55 (dd, J=5.8 Hz, J=15.8 Hz, 1H); 2.81 (dd, J=7.8 Hz, J=15.8 Hz, 1H); 3.10 (s, 3H); 4.25 (d, J=15.0 Hz, 1H); 4.80 (d, J=15.5 Hz, 1H); 5.01-5.13 (m, 3H); 5.52-5.55 (m, 1H); 7.25-7.52 (m, 10).

Example 7F

N-Benzyloxycarbonyl-D-aspartic acid β-t-butyl ester α-[(S)-1-(3-trifluoromethylphenyl)ethyl]amide. N-benzyloxycarbonyl-D-aspartic acid β-t-butyl ester monohydrate (Novabiochem) (84 mg, 0.25 mmol) and 47 mg of (S)-1-(3-trifluoromethylphenyl)ethylamine gave 122 mg (quantitative yield) of Example 7F as an off-white solid. Example 7F exhibited an $^1$H NMR spectrum consistent with the assigned structure.

Example 7G

N-Benzyloxycarbonyl-D-aspartic acid β-t-butyl ester α-[(R)-1-(3-trifluoromethylphenyl)ethyl]amide. N-benzyloxycarbonyl-D-aspartic acid β-t-butyl ester monohydrate (Novabiochem) (150 mg, 0.44 mmol) and 83 mg of (R)-1-(3-trifluoromethylphenyl)ethylamine gave 217 mg (quantitative yield) of Example 7G as an off-white solid. Example 7G exhibited an $^1$H NMR spectrum consistent with the assigned structure.

Example 7H

N-Benzyloxycarbonyl-D-glutamic acid α-methyl ester γ-(3-trifluoromethyl)benzylamide. N-benzyloxycarbonyl-D-glutamic acid α-methyl ester (508 mg, 1.72 mmol) and 317 mg (1.81 mmol) of 3-(trifluoromethyl)benzylamine gave 662 mg (85%) of Example 7H as an off-white solid. Example 7H exhibited an $^1$H NMR spectrum consistent with the assigned structure.

Example 8

General procedure for hydrogenation of a benzyloxycarbonyl amine. L-aspartic acid β-t-butyl ester α-(3-trifluoromethyl)benzylamide. A suspension of 2.23 g (4.64 mmol) of N-benzyloxycarbonyl-L-aspartic acid β-t-butyl ester α-(3-trifluoromethyl)benzylamide and palladium (5% wt. on activated carbon, 0.642 g) in 30 mL of methanol was held under an atmosphere of hydrogen until complete conversion as determined by thin layer chromatography (95:5 dichloromethane/methanol eluent). The reaction was filtered to remove the palladium over carbon and the filtrate was evaporated to give 1.52 g (96%) of the title compound as an oil; $^1$H NMR (CDCl$_3$) δ 1.42 (s, 9H); 2.26 (brs, 2H); 2.63-2.71 (m, 1H); 2.82-2.87 (m, 1H); 3.75-3.77 (m, 1H); 4.47-4.50 (m, 2H); 7.41-7.52 (m, 4H); 7.90 (brs, 1H).

Examples 9-13P were prepared according to the procedure of Example 8, except that N-benzyloxycarbonyl-L-aspartic acid β-t-butyl ester α-(3-trifluoromethyl)benzylamide was replaced by the appropriate amino acid derivative.

Example 9

L-aspartic acid β-t-butyl ester α-[4-(2-phenylethyl)]piperazinamide. N-benzyloxycarbonyl-L-aspartic acid β-t-butyl ester α-[4-(2-phenylethyl)]piperazinamide (5.89 g, 11.9 mmol) gave 4.24 g (98%) of Example 9 as an off-white oil; $^1$H NMR (CDCl$_3$): δ 1.42 (s, 9H); 2.61-2.95 (m, 10H); 3.60-3.90 (m, 4H); 4.35-4.45 (m, 1H); 7.17-7.29 (m, 5H).

Example 10

D-aspartic acid β-t-butyl ester α-(3-trifluoromethyl)benzylamide. N-benzyloxycarbonyl-D-aspartic acid β-t-butyl ester α-(3-trifluoromethyl)benzylamide (1.41 g, 2.93 mmol) gave 0.973 g (96%) of Example 10 as an off-white oil; $^1$H NMR (CDCl$_3$): δ 1.42 (s, 9H); 2.21 (brs, 2H); 2.67 (dd, J=7.1 Hz, J=16.8 Hz, 1H); 2.84 (dd, J=3.6 Hz, J=16.7 Hz, 1H); 3.73-3.77 (m, 1H); 4.47-4.50 (m, 2H); 7.41-7.52 (m, 4H); 7.83-7.87 (m, 1H).

Example 11

L-glutamic acid γ-t-butyl ester α-(3-trifluoromethyl)benzylamide. N-benzyloxycarbonyl-L-glutamic acid γ-t-butyl ester α-(3-trifluoromethyl)benzylamide (5.41 g, 10.9 mmol) gave 3.94 g (quantitative yield) of Example 11 as an off-white oil; $^1$H NMR (CDCl$_3$): δ 1.41 (s, 9H); 1.73-1.89 (m, 3H); 2.05-2.16 (m, 1H); 2.32-2.38 (m, 2H); 3.47 (dd, J=5.0 Hz, J=7.5 Hz, 1H); 4.47-4.49 (m, 2H); 7.36-7.54 (m, 4H); 7.69-7.77 (m, 1H).

Example 12

L-glutamic acid γ-t-butyl ester α-[4-(2-phenylethyl)]piperazinamide. N-benzyloxycarbonyl-L-glutamic acid γ-t-butyl ester α-[4-(2-phenylethyl)]piperazinamide (5.86 g, 11.50 mmol) gave 4.28 g (99%) of Example 12 as an off-white oil; $^1$H NMR (CDCl$_3$) δ 1.39 (s, 9H); 2.00-2.08 (m, 1H); 2.38-2.46 (m, 1H); 2.55-2.90 (m, 9H); 3.61-3.82 (m, 4H); 4.48-4.56 (m, 1H); 7.17-7.26 (m, 5H).

Example 13

D-glutamic acid γ-t-butyl ester α-(3-trifluoromethyl)benzylamide. N-benzyloxycarbonyl-D-glutamic acid γ-t-butyl ester α-(3-trifluoromethyl)benzylamide (1.667 g, 3.37 mmol) gave 1.15 g (94%) of Example 13 as an off-white oil; $^1$H NMR (CDCl$_3$) δ 1.41 (s, 9H); 1.80-2.20 (m, 4H); 2.31-2.40 (m, 2H); 3.51-3.59 (m, 1H); 4.47-4.49 (m, 2H); 7.39-7.52 (m, 4H); 7.71-7.79 (m, 1H).

Example 13A

L-glutamic acid α-t-butyl ester γ-(4-cyclohexyl)piperazinamide. N-Benzyloxycarbonyl-L-glutamic acid α-t-butyl ester γ-(4-cyclohexyl)piperazinamide (1.93 g, 3.96 mmol) gave 1.30 g (93%) of Example 13A as an off-white oil; $^1$H NMR (CDCl$_3$) δ 1.02-1.25 (m, 5H); 1.41 (s, 9H); 1.45-1.50 (m, 1H); 1.56-1.60 (m, 1H); 1.69-1.80 (m, 6H); 3.30 (dd, J=4.8 Hz, J=8.5 Hz, 1H); 3.44 (t, J=9.9 Hz, 2H); 3.56 (t, J=9.9 Hz, 2H).

Example 13B

D-aspartic acid β-t-butyl ester α-(2-fluoro-3-trifluoromethyl)benzylamide. N-benzyloxycarbonyl-D-aspartic acid β-t-butyl ester α-(2-fluoro-3-trifluoromethyl)benzylamide (0.36 g, 0.72 mmol) gave 0.256 g (92%) of Example 13B as an off-white oil; $^1$H NMR (CDCl$_3$) δ 1.39 (s, 9H); 2.50 (brs, 2H); 2.74 (dd, J=7.0 Hz, J=16.5 Hz, 1H); 2.86 (dd, J=4.8 Hz, J=16.8 Hz, 1H); 3.89 (brs, 2H); 4.47-4.57 (m, 2H); 7.16 (t, J=7.8 Hz, 1H); 7.48 (t, J=7.3 Hz, 1H); 7.56 (t, J=7.3 Hz, 1H); 7.97-8.02 (m, 1H).

Example 13C

D-aspartic acid β-t-butyl ester α-[(S)-α-methyl]benzylamide. N-benzyloxycarbonyl-D-aspartic acid β-t-butyl ester α-[(S)-α-methylbenzyl]amide (0.275 g, 0.65 mmol) gave 0.17 g (90%) of Example 13C as an off-white oil; $^1$H NMR (CDCl₃) δ 1.40 (s, 9H); 1.47 (d, J=6.9 Hz, 3H); 1.98 (brs, 2H); 2.49 (dd, J=7.9 Hz, J=17.7 Hz, 1H); 2.83 (dd, J=3.6 Hz, J=16.7 Hz, 1H); 3.69 (brs, 1H); 4.99-5.10 (m, 1H); 7.19-7.33 (m, 5H); 7.65-7.68 (m, 11H).

Example 13D

D-aspartic acid β-t-butyl ester α-[(R)-α-methylbenzyl]amide. N-benzyloxycarbonyl-D-aspartic acid β-t-butyl ester α-[(R)-α-methylbenzyl]amide (0.273 g, 0.64 mmol) gave 0.187 g (quantitative yield) of Example 13D as an off-white oil; ¹H NMR (CDCl₃) δ 1.38 (s, 9H); 1.46 (d, J=6.9 Hz, 3H); 1.79 (brs, 2H); 2.51 (dd, J=7.8 Hz, J=17.5 Hz, 1H); 2.87 (dd, J=3.6 Hz, J=16.9 Hz, 1H); 4.19 (brs, 1H); 4.99-5.11 (m, 1H); 7.18-7.34 (m, 5H); 7.86-7.90 (m, 1H).

Example 13E

D-aspartic acid β-t-butyl ester α-[N-methyl-N-(3-trifluoromethylbenzyl)]amide. N-benzyloxycarbonyl-D-aspartic acid β-t-butyl ester α-[N-methyl-N-(3-trifluoromethylbenzyl)]amide (0.282 g, 0.57 mmol) gave 0.195 g (95%) of Example 13E as an off-white oil. Example 13E exhibited an ¹H NMR spectrum consistent with the assigned structure.

Example 13F

L-aspartic acid β-t-butyl ester α-[4-(2-phenylylethyl)]piperazinamide. N-benzyloxycarbonyl-L-aspartic acid β-t-butyl ester α-[4-(2-phenylethyl)]piperazinamide (5.89 g, 11.9 mmol) gave 4.24 g (98%) of Example 13F as an off-white oil; ¹H NMR (CDCl₃): δ 1.42 (s, 9H); 2.61-2.95 (m, 10H); 3.60-3.90 (m, 4H); 4.35-4.45 (m, 1H); 7.17-7.29 (m, 5I).

Example 13G

D-aspartic acid β-t-butyl ester α-(3-trifluoromethyl)benzylamide. N-benzyloxycarbonyl-D-aspartic acid β-t-butyl ester α-(3-trifluoromethyl)benzylamide (1.41 g, 2.93 mmol) gave 0.973 g (96%) of Example 13G as an off-white oil; ¹H NMR (CDCl₃): δ 1.42 (s, 9H); 2.21 (brs, 2H); 2.67 (dd, J=7.1 Hz, J=16.8 Hz, 1H); 2.84 (dd, J=3.6 Hz, J=16.7 Hz, 1H); 3.73-3.77 (m, 1H); 4.47-4.50 (m, 2H); 7.41-7.52 (m, 4H); 7.83-7.87 (m, 1H).

Example 13H

L-glutamic acid γ-t-butyl ester α-(3-trifluoromethyl)benzylamide. N-benzyloxycarbonyl-L-glutamic acid γ-t-butyl ester α-(3-trifluoromethyl)benzylamide (5.41 g, 10.9 mmol) gave 3.94 g (quantitative yield) of Example 13H as an off-white oil; ¹H NMR (CDCl₃): δ 1.41 (s, 9H); 1.73-1.89 (m, 3H); 2.05-2.16 (m, 1H); 2.32-2.38 (m, 2H); 3.47 (dd, J=5.0 Hz, J=7.5 Hz, 1H); 4.47-4.49 (m, 2H); 7.36-7.54 (m, 4H); 7.69-7.77 (m, 1H).

Example 13I

L-glutamic acid γ-t-butyl ester α-[4-(2-phenylethyl)]piperazinamide. N-benzyloxycarbonyl-L-glutamic acid γ-t-butyl ester α-[4-(2-phenylethyl)]piperazinamide (5.86 g, 11.50 mmol) gave 4.28 g (99%) of Example 13I as an off-white oil; ¹H NMR (CDCl₃) δ 1.39 (s, 9H); 2.00-2.08 (m, 1H); 2.38-2.46 (m, 1H); 2.55-2.90 (m, 9H); 3.61-3.82 (m, 4H); 4.48-4.56 (m, 1H); 7.17-7.26 (m, 5H).

Example 13J

D-glutamic acid γ-t-butyl ester α-(3-trifluoromethyl)benzylamide. N-benzyloxycarbonyl-D-glutamic acid γ-t-butyl ester α-(3-trifluoromethyl)benzylamide (1.667 g, 3.37 mmol) gave 1.15 g (94%) of Example 13J as an off-white oil; ¹H NMR (CDCl₃) δ 1.41 (s, 9H); 1.80-2.20 (m, 4H); 2.31-2.40 (m, 2H); 3.51-3.59 (m, 1H); 4.47-4.49 (m, 2H); 7.39-7.52 (m, 4H); 7.71-7.79 (m, 1H).

Example 13K

L-glutamic acid α-t-butyl ester γ-(4-cyclohexyl)piperazinamide. N-Benzyloxycarbonyl-L-glutamic acid α-t-butyl ester γ-(4-cyclohexyl)piperazinamide (1.93 g, 3.96 mmol) gave 1.30 g (93%) of Example 13K as an off-white oil; ¹H NMR (CDCl₃) δ 1.02-1.25 (m, 5H); 1.41 (s, 9H); 1.45-1.50 (m, 1H); 1.56-1.60 (m, 1H); 1.69-1.80 (m, 6H); 3.30 (dd, J=4.8 Hz, J=8.5 Hz, 1H); 3.44 (t, J=9.9 Hz, 2H); 3.56 (t, J=9.9 Hz, 2H).

Example 13L

D-aspartic acid β-t-butyl ester α-(2-fluoro-3-trifluoromethyl)benzylamide. N-benzyloxycarbonyl-D-aspartic acid β-t-butyl ester α-(2-fluoro-3-trifluoromethyl)benzylamide (0.36 g, 0.72 mmol) gave 0.256 g (92%) of Example 13L as an off-white oil; ¹H NMR (CDCl₃) δ 1.39 (s, 9H); 2.50 (brs, 2H); 2.74 (dd, J=7.0 Hz, J=16.5 Hz, 1H); 2.86 (dd, J=4.8 Hz, J=16.8 Hz, 1H); 3.89 (brs, 2H); 4.47-4.57 (m, 2H); 7.16 (t, J=7.8 Hz, 1H); 7.48 (t, J=7.3 Hz, 1H); 7.56 (t, J=7.3 Hz, 1H); 7.97-8.02 (m, 1H).

Example 13M

D-aspartic acid β-t-butyl ester α-[(S)-1-(3-trifluoromethylphenyl)ethyl]amide. N-benzyloxycarbonyl-D-aspartic acid β-t-butyl ester α-[(S)-1-(3-trifluoromethylphenyl)ethyl]amide (120 mg, 0.24 mmol) gave 91 mg (91%) of Example 13M as an off-white oil, and exhibited an ¹H NMR spectrum consistent with the assigned structure.

Example 13N

D-aspartic acid β-t-butyl ester α-[(R)-1-(3-trifluoromethylphenyl)ethyl]amide. N-benzyloxycarbonyl-D-aspartic acid β-t-butyl ester α-[(R)-1-(3-trifluoromethylphenyl)ethyl]amide (217 mg, 0.44 mmol) gave 158 mg (quantitative yield) of Example 13N as an off-white oil, and exhibited an ¹H NMR spectrum consistent with the assigned structure.

Example 13O

D-aspartic acid β-t-butyl ester α-[N-methyl-N-(3-trifluoromethylbenzyl)]amide. N-benzyloxycarbonyl-D-aspartic acid β-t-butyl ester α-[N-methyl-N-(3-trifluoromethylbenzyl)]amide (0.282 g, 0.57 mmol) gave 0.195 g (95%) of Example 13O as an off-white oil, and exhibited an ¹H NMR spectrum consistent with the assigned structure.

Example 13P

D-glutamic acid α-methyl ester γ-(3-trifluoromethyl)benzylamide. N-Benzyloxycarbonyl-D-glutamic acid α-methyl ester γ-(3-trifluoromethyl)benzylamide (764 mg, 1.69 mmol) gave g (516 mg, 96%) of Example 13P as an off-white oil, and exhibited an ¹H NMR spectrum consistent with the assigned structure.

Example 14

General procedure for formation of a 2-azetidinone from an imine and an acetyl chloride.

Step 1: General procedure for formation of an imine from an amino acid derivative. A solution of 1 equivalent of an α-amino acid ester or amide in dichloromethane is treated sequentially with 1 equivalent of an appropriate aldehyde, and a dessicating agent, such as magnesium sulfate or silica gel, in the amount of about 2 grams of dessicating agent per gram of starting α-amino acid ester or amide. The reaction is stirred at ambient temperature until all of the reactants are consumed as measured by thin layer chromatography. The reactions are typically complete within an hour. The reaction mixture is then filtered, the filter cake is washed with dichloromethane, and the filtrate concentrated under reduced pressure to provide the desired imine that is used as is in the subsequent step. Step 2: General procedure for the 2+2 cycloaddition of an imine and an acetyl chloride. A dichloromethane solution of the imine (10 mL dichloromethane/1 gram imine) is cooled to 0° C. To this cooled solution is added 1.5 equivalents of an appropriate amine, typically triethylamine, followed by the dropwise addition of a dichloromethane solution of 1.1 equivalents of an appropriate acetyl chloride, such as that described in Example 1 (10 mL dichloromethane/1 gm appropriate acetyl chloride). The reaction mixture is allowed to warm to ambient temperature over 1 h and is then quenched by the addition of a saturated aqueous solution of ammonium chloride. The resulting mixture is partitioned between water and dichloromethane. The layers are separated and the organic layer is washed successively with 1N hydrochloric acid, saturated aqueous sodium bicarbonate, and saturated aqueous sodium chloride. The organic layer is dried over magnesium sulfate and concentrated under reduced pressure. The residue may be used directly for further reactions, or purified by chromatography or by crystallization from an appropriate solvent system if desired. In each case, following the 2+2 reaction, the stereochemistry of the β-lactam may be confirmed by circular dichroism/optical rotary dispersion (CD/ORD). Illustratively, examples of the (αR,3S,4R) and (αS,3S,4R) β-lactam platform stereochemical configurations from prior syntheses may be used as CD/ORD standards.

Example 15 tert-Butyl[3(S)-(4(S)-phenyloxazolidin-2-on-3-yl)-4(R)-(2-styryl)azetidin-2-on-1-yl]acetate. Using the procedure of Example 14, the imine prepared from 4.53 g (34.5 mmol) glycine tert-butyl ester and cinnamaldehyde was combined with 2-(4(S)-phenyloxazolidin-2-on-3-yl)acetyl chloride (Example 1) to give 5.5 g (30%) of Example 15 as colorless crystals (recrystallized, n-chlorobutane); mp 194-195° C.

Example 16

General procedure for acylation of an azetidin-2-on-1-ylacetate. A solution of (azetidin-2-on-1-yl)acetate in tetrahydrofuran (0.22 M in azetidinone) is cooled to −78° C. and is with lithium bis(trimethylsilyl)amide (2.2 equivalents). The resulting anion is treated with an appropriate acyl halide (1.1 equivalents). Upon complete conversion of the azetidinone, the reaction is quenched with saturated aqueous ammonium chloride and partitioned between ethyl acetate and water. The organic phase is washed sequentially with 1N hydrochloric acid, saturated aqueous sodium bicarbonate, and saturated aqueous sodium chloride. The resulting organic layer is dried (magnesium sulfate) and evaporated. The residue is purified by silica gel chromatography with an appropriate eluent, such as 3:2 hexane/ethyl acetate.

Example 17

2,2,2-Trichloroethyl 2(RS)-(tert-butoxycarbonyl)-2-[3(S)-(4(S)-phenyloxazolidin-2-on-3-yl)-4(R)-(2-styryl)azetidin-2-on-1-yl]acetate Using the procedure of Example 16, 9.0 g (20 mmol) of Example 15 was acylated with 4.2 g (20 mmol) of trichloroethylchloroformate to give 7.0 g (56%) of Example 17; mp 176-178° C.

Example 18

2(RS)-(tert-Butoxycarbonyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. A solution of 0.20 g (0.32 mmol) of Example 17 and 52 μL (0.36 mmol) of (3-trifluoromethylbenzyl)amine in THF was heated at reflux. Upon complete conversion (TLC), the solvent was evaporated and the residue was recrystallized (chloroform/hexane) to give 0.17 g (82%) of Example 18 as a white solid; mp 182-184° C.

Example 18A

2(RS)-(tert-Butoxycarbonyl)-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)amide. Example 18A was prepared according to the procedure of Example 18, using 2-fluoro-3-(trifluoromethyl)benzylamine instead of (3-trifluoromethylbenzyl)amine. Example 18A was obtained as a white solid (140 mg, 41%), and exhibited an ¹H NMR spectrum consistent with the assigned structure.

Examples 19-25AF were prepared according to the procedure of Example 14, where the appropriate amino acid derivative and aldehyde were used in Step 1, and the appropriate acetyl chloride was used in Step 2.

Example 19

2(S)-(tert-Butoxycarbonylmethyl)-2-[3(S)-(4(S)-phenyloxazolidin-2-on-3-yl)-4(R)-(2-styryl)azetidin-2-on-1-yl] acetic acid N-(3-trifluoromethylbenzyl)amide. The imine prepared from 1.52 g (4.39 mmol) of L-aspartic acid β-t-butyl ester α-(3-trifluoromethyl)benzylamide and cinnamaldehyde was combined with 2-(4(S)-phenyloxazolidin-2-on-3-yl)acetyl chloride (Example 1) to give 2.94 g of an orange-brown oil that gave, after flash column chromatography purification (70:30 hexanes/ethyl acetate), 2.06 g (70%) of Example 19 as a white solid; ¹H NMR (CDCl₃) δ 1.39 (s, 9H); 2.46 (dd, J=11.1 Hz, J=16.3 Hz, 1H); 3.18 (dd, J=3.8 Hz, J=16.4 Hz, 1H); 4.12-4.17 (m, 1H); 4.26 (d, J=5.0 Hz, 1H); 4.45 (dd, J=6.0 Hz, J=14.9 Hz, 1H); 4.54 (dd, J=5.3 Hz, J=9.8 Hz, 1H); 4.58-4.66 (m, 3H); 4.69-4.75 (m, 1H); 4.81 (dd, J=3.8 Hz, J=11.1 Hz, 1H); 6.25 (dd, J=9.6 Hz, J=15.8 Hz, 1H); 6.70 (d, J=15.8 Hz, 1H); 7.14-7.17 (m, 2H); 7.28-7.46 (m, 11H); 7.62 (s, 1H); 8.27-8.32 (m, 1H).

Example 19A

2(S)-(tert-Butoxycarbonylmethyl)-2-[3(R)-(4(R)-phenyloxazolidin-2-on-3-yl)-4(S)-(2-styryl)azetidin-2-on-1-yl]

acetic acid N-(3-trifluoromethylbenzyl)amide. Example 19A was prepared according to the method of Example 19 except that 2-(4(R)-phenyloxazolidin-2-on-3-yl)acetyl chloride (Example 1A) was used instead of 2-(4(S)-phenyloxazolidin-2-on-3-yl)acetyl chloride. Example 19A was obtained as a white solid (41 mg, 13%); $^1$H NMR (CDCl$_3$) δ 1.37 (s, 9H); 3.11 (dd, J=3.7 Hz, J=17.8 Hz, 1H); 3.20 (dd, J=10.6 Hz, J=17.8 Hz, 1H); 4.02 (dd, J=3.7 Hz, J=10.6 Hz, 1H); 4.10-4.17 (m, 1H); 4.24 (d, J=4.9 Hz, 1H); 4.4652-4.574 (dd, J=5.9 Hz, J=15.1 Hz, 1H); 4.58-4.76 (m, 4H); 6.27 (dd, J=9.6 Hz, J=15.8 Hz, 1H); 6.79 (d, J=15.8 Hz, 1H); 7.23-7.53 (m, 13H); 7.63 (s, 1H); 8.51-8.55 (m, 1H).

Example 20

2(S)-(tert-Butoxycarbonylethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. The imine prepared from 3.94 g (10.93 mmol) of L-glutamic acid γ-t-butyl ester α-(3-trifluoromethyl)benzylamide and cinnamaldehyde was combined with 2-(4(S)-phenyloxazolidin-2-on-3-yl)acetyl chloride (Example 1) to give 5.53 g (75%) of Example 20 after flash column chromatography purification (70:30 hexanes/ethyl acetate); $^1$H NMR (CDCl$_3$) δ 1.36 (s, 9H); 1.85-1.96 (m, 1H); 2.18-2.49 (m, 3H); 4.14-4.19 (m, 1H); 4.30 (d, J=4.9 Hz, 2H); 4.44 (dd, J=6.1 Hz, J=14.9 Hz, 1H); 4.56-4.67 (m, 4H); 4.71-4.75 (m, 1H); 6.26 (dd, J=9.6 Hz, J=15.8 Hz, 1H); 6.71 (d, J=15.8 Hz, 1H); 7.16-7.18 (m, 2H); 7.27-7.49 (m, 11H); 7.60 (s, 1H); 8.08-8.12 (m, 1H).

Example 21

2(S)-(tert-Butoxycarbonylmethyl)-2-[3(S)-(4(S)-phenyloxazolidin-2-on-3-yl)-4(R)-(2-styryl)azetidin-2-on-1-yl] acetic acid N-[4-(2-phenylethyl)]piperazinamide. The imine prepared from 4.20 g (11.6 mmol) of L-aspartic acid β-t-butyl ester α-[4-(2-phenylethyl)]piperazinamide and cinnamaldehyde was combined with 2-(4(S)-phenyloxazolidin-2-on-3-yl)acetyl chloride (Example 1) to give 4.37 g (55%) of Example 21 after flash column chromatography purification (50:50 hexanes/ethyl acetate); $^1$H NMR (CDCl$_3$) δ 1.34 (s, 9H); 2.26-2.32 (m, 1H); 2.46-2.63 (m, 4H); 2.75-2.89 (m, 4H); 3.24-3.32 (m, 1H); 3.49-3.76 (m, 3H); 4.07-4.13 (m, 1H); 4.30 (d, J=4.6 Hz, 1H); 4.22-4.48 (m, 1H); 4.55-4.61 (m, 1H); 4.69-4.75 (m, 1H); 5.04-5.09 (m, 1H); 6.15 (dd, J=9.3 Hz, J=15.9 Hz, 1H); 6.63 (d, J=15.8 Hz, 1H); 7.18-7.42 (m, 15H).

Example 22

2(S)-(tert-Butoxycarbonylethyl)-2-[3(S)-(4(S)-phenyloxazolidin-2-on-3-yl)-4(R)-(2-styryl)azetidin-2-on-1-yl]acetic acid N-[4-(2-phenylethyl)]piperazinamide. The imine prepared from 2.54 g (6.75 mmol) of L-glutamic acid γ-t-butyl ester α-[4-(2-phenylethyl)]piperazinamide and cinnamaldehyde was combined with 2-(4(S)-phenyloxazolidin-2-on-3-yl)acetyl chloride (Example 1) to give 3.55 g (76%) of Example 22 after flash column chromatography purification (50:50 hexanes/ethyl acetate); $^1$H NMR (CDCl$_3$) δ 1.32 (s, 9H); 1.96-2.07 (m, 1H); 2.15-2.44 (m, 6H); 2.54-2.62 (m, 2H); 2.69-2.81 (m, 3H); 3.28-3.34 (m, 1H); 3.59-3.68 (m, 1H); 4.08-4.13 (m, 1H); 4.33-4.44 (m, 2H); 4.48-4.60 (m, 2H); 4.67-4.77 (m, 1H); 6.14 (dd, J=8.9 Hz, J=16.0 Hz, 1H); 6.62 (d, J=16.0 Hz, 1H); 7.16-7.42 (m, 15H).

Example 23

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N-(3-trifluoromethylbenzyl)amide. The imine prepared from 0.973 g (2.81 mmol) of D-aspartic acid β-t-butyl ester α-(3-trifluoromethyl)benzylamide and cinnamaldehyde was combined with 2-(4(S)-phenyloxazolidin-2-on-3-yl)acetyl chloride (Example 1) to give 1.53 g (82%) of Example 23 after flash column chromatography purification (70:30 hexanes/ethyl acetate); $^1$H NMR (CDCl$_3$) δ 1.37 (s, 9H); 3.10 (dd, J=3.7 Hz, J=17.8 Hz, 1H); 3.20 (dd, J=10.7 Hz, J=17.8 Hz, 1H); 4.02 (dd, J=3.6 Hz, J=10.6 Hz, 1H); 4.11-4.17 (m, 1H); 4.24 (d, J=4.9 Hz, 1H); 4.46 (dd, J=5.8 Hz, J=15.1 Hz, 1H); 4.58-4.67 (m, 3H); 4.70-4.76 (m, 1H); 6.27 (dd, J=9.5 Hz, J=15.8 Hz, 1H); 6.79 (d, J=15.8 Hz, 1H); 7.25-7.50 (m, 13H); 7.63 (s, 1H); 8.50-8.54 (m, 1H).

Example 23A

2(R)-(tert-Butoxycarbonylmethyl)-2-[3(R)-(4(R)-phenyloxazolidin-2-on-3-yl)-4(S)-(2-styryl)azetidin-2-on-1-yl] acetic acid N-(3-trifluoromethylbenzyl)amide. Example 23A was prepared according to the method of Example 23 except that 2-(4(R)-phenyloxazolidin-2-on-3-yl)acetyl chloride (Example 1A) was used instead of 2-(4(S)-phenyloxazolidin-2-on-3-yl)acetyl chloride. Example 23A was obtained as a white solid (588 mg, 49%); $^1$H NMR (CDCl$_3$) δ 1.39 (s, 9H); 2.47 (dd, J=11.2 Hz, J=16.3 Hz, 1H); 3.18 (dd, J=3.8 Hz, J=16.3 Hz, 1H); 4.15 (t, J=8.25, Hz 1H); 4.26 (d, J=5.0 Hz, 1H); 4.45 (dd, J=6.0 Hz, J=15.0 Hz, 1H); 4.52-4.57 (m, 3H); 4.63 (t, J=9 Hz, 1H); 4.70 (t, J=8 Hz, 1H); 4.81 (dd, J=3.8 Hz, J=10.8 Hz, 1H); 6.25 (dd, J=9.8 Hz, J=15.8 Hz, 1H); 6.70 (d, J=15.8 Hz, 1H); 7.15-7.17 (m, 2H); 7.27-7.51 (m, 111H); 7.62 (s, 1H); 8.27-8.32 (m, 1H).

Example 24

2(R)-(tert-Butoxycarbonylethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. The imine prepared from 1.15 g (3.20 mmol) of D-glutamic acid γ-t-butyl ester α-(3-trifluoromethyl)benzylamide and cinnamaldehyde was combined with 2-(4(S)-phenyloxazolidin-2-on-3-yl)acetyl chloride (Example 1) to give 1.84 g (85%) of Example 24 after flash column chromatography purification (70:30 hexanes/ethyl acetate); $^1$H NMR (CDCl$_3$) δ 1.37 (s, 9H); 2.23-2.39 (m, 4H); 3.71-3.75 (m, 1H); 4.13-4.18 (m, 1H); 4.31 (d, J=4.9 Hz, 1H); 4.44-4.51 (m, 2H); 4.56-4.68 (m, 2H); 4.71-4.76 (m, 1H); 6.26 (dd, J=9.5 Hz, J=15.8 Hz, 1H); 6.71 (d, J=15.8 Hz, 1H); 7.25-7.52 (m, 13H); 7.63 (s, 1H); 8.25-8.30 (m, 1H).

Example 25

2(S)-(tert-Butoxycarbonylethyl)-2-[3(S)-(4(S)-phenyloxazolidin-2-on-3-yl)-4(R)-(2-styryl)azetidin-2-on-1-yl]acetic acid N-(4-cyclohexyl)piperazinamide. The imine prepared from 2.58 g (5.94 mmol) of L-glutamic acid γ-t-butyl ester α-(4-cyclohexyl)piperazinamide and cinnamaldehyde was combined with 2-(4(S)-phenyloxazolidin-2-on-3-yl)acetyl chloride (Example 1) to give 3.27 g (94%) of Example 25 after flash column chromatography purification (95:5 dichloromethane/methanol); $^1$H NMR (CDCl$_3$) δ 1.32 (s, 9H); 1.10-1.18 (m, 1H); 1.20-1.31 (m, 2H); 1.38-1.45 (m, 2H); 1.61-1.66 (m, 1H); 1.84-1.89 (m, 2H); 1.95-2.01 (m, 1H); 2.04-2.14 (m, 3H); 2.20-2.24 (m, 1H); 2.29-2.35 (m, 1H); 2.85-2.92 (m, 1H); 3.24-3.32 (m, 1H); 3.36-3.45 (m, 2H); 3.80-3.86 (m, 1H); 4.08 (t, J=8.3 Hz, 1H); 4.27 (d, J=5.0 Hz, 1H); 4.31-4.55 (m, 4H); 4.71 (t, J=8.3 Hz, 1H);

4.83-4.90 (m, 1H); 6.18 (dd, J=9.1 Hz, J=15.9 Hz, 1H); 6.67 (d, J=15.9 Hz, 1H); 7.25-7.44 (m, 10H); 8.22 (brs, 1H).

Example 25A tert-Butyl 2(S)-(2-(4-cyclohexylpiperazinylcarbonyl)ethyl)-2-[3(S)-(4(S)-phenyloxazolidin-2-on-3-yl)-4(R)-(2-styryl)azetidin-2-on-1-yl]acetate. The imine prepared from 1.282 g (3.63 mmol) of L-glutamic acid α-t-butyl ester γ-(4-cyclohexyl)piperazinamide and cinnamaldehyde was combined with 2-(4(S)-phenyloxazolidin-2-on-3-yl)acetyl chloride (Example 1) to give 1.946 g (80%) of Example 25A after flash column chromatography purification (50:50 hexanes/ethyl acetate); $^1$H NMR (CDCl$_3$) δ 1.15-1.26 (m, 6H); 1.39 (s, 9H); 1.55-1.64 (m, 2H); 1.77-1.83 (m, 3H); 2.22-2.35 (m, 2H); 2.40-2.50 (m, 6H); 2.75-2.79 (m, 1H); 3.43-3.48 (m, 1H); 3.56-3.60 (m, 2H); 3.75-3.79 (m, 1H); 4.10 (t, J=8.3 Hz, 1H); 4.31-4.35 (m, 2H); 4.58 (t, J=8.8 Hz, 1H); 4.73 (t, J=8.4 Hz, 1H); 6.17 (dd, J=8.6 Hz, J=16.0 Hz, 1H); 6.65 (d, J=16.0 Hz, 1H); 7.27-7.42 (m, 10H).

Example 25B

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N-(2-fluoro-3-trifluoromethylbenzyl)amide. The imine prepared from 0.256 g (0.70 mmol) of D-aspartic acid β-t-butyl ester α-(2-fluoro-3-trifluoromethyl)benzylamide and cinnamaldehyde was combined with 2-(4(S)-phenyloxazolidin-2-on-3-yl)acetyl chloride (Example 1) to give 0.287 g (60%) of Example 25B after flash column chromatography purification (70:30 hexanes/ethyl acetate); $^1$H NMR (CDCl$_3$) δ 1.38 (s, 9H); 3.12 (dd, J=4.0 Hz, J=17.8 Hz, 11H); 3.20 (dd, J=10.4 Hz, J=17.8 Hz, 1H); 4.05 (dd, J=3.9 Hz, J=10.4 Hz, 1H); 4.14 (dd, J=J'=8.2 Hz, 1H); 4.25 (d, J=4.9 Hz, 1H); 4.59-4.67 (m, 4H); 4.74 (t, J=8.3 Hz, 1H); 6.36 (dd, J=9.6 Hz, J=15.8 Hz, 1H); 6.83 (d, J=15.8 Hz, 1H); 7.02-7.07 (m, 1H); 7.28-7.55 (m, 12H); 8.44-8.48 (m, 1H).

Example 25C

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N—[(S)-α-methylbenzyl]amide. The imine prepared from 0.167 g (0.57 mmol) of D-aspartic acid β-t-butyl ester [(S)-α-methylbenzyl]amide and cinnamaldehyde was combined with 2-(4(S)-phenyloxazolidin-2-on-3-yl)acetyl chloride (Example 1) to give 0.219 g (63%) of Example 25C after flash column chromatography purification (70:30 hexanes/ethyl acetate); $^1$H NMR (CDCl$_3$) δ 1.35 (s, 9H); 1.56 (d, J=7.0 Hz, 3H); 2.97 (dd, J=3.5 Hz, J=18.0 Hz, 1H); 3.15 (dd, J=11.0 Hz, J=17.5 Hz, 1H); 4.01 (dd, J=3.0 Hz, J=11.0 Hz, 1H); 4.14 (t, J=8.5 Hz, 1H); 4.24 (d, J=5.0 Hz, 1H); 4.57 (dd, J=5.0 Hz, J=9.5 Hz, 1H); 4.64 (t, J=8.8 Hz, 1H); 5.07 (t, J=8.5 Hz, 1H); 5.03-5.09 (m, 1H); 6.43 (dd, J=9.5 Hz, J=16.0 Hz, 1H); 6.83 (d, J=16.0 Hz, 1H); 7.16-7.20 (m, 1H); 7.27-7.49 (m, 14H); 8.07-8.10 (m, 1H).

Example 25D

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N—[(R)-α-methylbenzyl]amide. The imine prepared from 0.187 g (0.46 mmol) of D-aspartic acid β-t-butyl ester [(R)-α-methylbenzyl]amide and cinnamaldehyde was combined with 2-(4(S)-phenyloxazolidin-2-on-3-yl)acetyl chloride (Example 1) to give 0.25 g (64%) of Example 25D after flash column chromatography purification (70:30 hexanes/ethyl acetate); $^1$H NMR (CDCl$_3$) δ 1.36 (s, 9H); 1.59 (d, J=7.1 Hz, 3H); 3.10 (dd, J=3.5 Hz, J=17.8 Hz, 1H); 3.22 (dd, J=10.9 Hz, J=17.8 Hz, 1H); 3.93 (dd, J=3.5 Hz, J=10.8 Hz, 1H); 4.14 (t, J=8.1 Hz, 1H); 4.24 (d, J=5.0 Hz, 1H); 4.58 (dd, J=5.0 Hz, J=9.5 Hz, 1H); 4.65 (t, J=8.7 Hz, 1H); 4.74 (t, J=8.2 Hz, 1H); 5.06-5.14 (m, 1H); 6.32 (dd, J=9.5 Hz, J=15.8 Hz, 1H); 6.74 (d, J=15.8 Hz, 1H); 7.19-7.43 (m, 15H); 8.15-8.18 (m, 11H).

Example 25E

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N-methyl-N-(3-trifluoromethylbenzyl)amide. The imine prepared from 0.195 g (0.41 mmol) of D-aspartic acid β-t-butyl ester α-[N-methyl-N-(3-trifluoromethylbenzyl)]amide and cinnamaldehyde was combined with 2-(4(S)-phenyloxazolidin-2-on-3-yl)acetyl chloride (Example 1) to give 0.253 g (69%) of Example 25E after flash column chromatography purification (70:30 hexanes/ethyl acetate); $^1$H NMR (CDCl$_3$) δ 1.36 (s, 9H); 2.53 (dd, J=4.0 Hz, J=17.0 Hz, 1H); 3.06 (dd, J=10.8 Hz, J=16.8 Hz, 1H); 3.13 (s, 3H); 4.12 (dd, J=8.0 Hz, J=9.0 Hz, 1H); 4.26 (d, J=5.0 Hz, 1H); 4.38 (d, J=15.0 Hz, 1H); 4.46 (dd, J=5.0 Hz, J=9.5 Hz, 1H); 4.56 (t, J=6.8 Hz, 1H); 4.70-4.79 (m, 2H); 5.27 (dd, J=4.0 Hz, J=11.0 Hz, 1H); 6.22 (dd, J=9.3 Hz, J=15.8 Hz, 1H); 6.73 (d, J=15.8 Hz, 1H); 7.33-7.45 (m, 14H).

Example 25F

2(S)-(tert-Butoxycarbonylethyl)-2-[3(S)-(4(S)-phenyloxazolidin-2-on-3-yl)-4(R)-(2-chlorostyr-2-yl)azetidin-2-on-1-yl]acetic acid N-(3-trifluoromethylbenzyl)amide. The imine prepared from 1.62 g (4.44 mmol) of L-glutamic acid γ-t-butyl ester α-(3-trifluoromethyl)benzylamide and α-chlorocinnamaldehyde was combined with 2-(4(S)-phenyloxazolidin-2-on-3-yl)acetyl chloride (Example 1) to give 0.708 g (22%) of Example 25F after flash column chromatography purification (70:30 hexanes/ethyl acetate); $^1$H NMR (CDCl$_3$) δ 1.35 (s, 9H); 1.68 (brs, 1H); 2.19-2.35 (m, 2H); 2.40-2.61 (m, 2H); 4.13 (dd, J=7.5 Hz, J=9.0 Hz, 1H); 4.22 (t, J=7.0 Hz, 1H); 4.34 (d, J=4.5 Hz, 1H); 4.45 (dd, J=5.5 Hz, J=15.0 Hz, 1H); 4.51-4.60 (m, 3H); 4.89 (dd, J=7.5 Hz, J=8.5 Hz, 1H); 6.89 (s, 1H); 7.28-7.54 (m, 14H).

Example 25G

2(R)-(tert-Butoxycarbonylmethyl)-2-[3(S)-(4(S)-phenyloxazolidin-2-on-3-yl)-4(R)-(2'-methoxystyr-2-yl)azetidin-2-on-1-yl]acetic acid N-(3-trifluoromethylbenzyl)amide. The imine prepared from 0.34 g (0.98 mmol) of D-aspartic acid 9-t-butyl ester α-(3-trifluoromethylbenzyl)amide and 2'-methoxycinnamaldehyde was combined with 2-(4(S)-phenyloxazolidin-2-on-3-yl)acetyl chloride (Example 1) to give 0.402 g (59%) of Example 25G after flash column chromatography purification (70:30 hexanes/ethyl acetate); $^1$H NMR (CDCl$_3$) δ 1.35 (s, 9H); 1.68 (brs, 1H); 2.19-2.35 (m, 2H); 2.40-2.61 (m, 2H); 4.13 (dd, J=7.5 Hz, J=9.0 Hz, 1H); 4.22 (t, J=7.0 Hz, 1H); 4.34 (d, J=4.5 Hz, 1H); 4.45 (dd, J=5.5 Hz, J=15.0 Hz, 1H); 4.51-4.60 (m, 3H); 4.89 (dd, J=7.5 Hz, J=8.5 Hz, 1H); 6.89 (s, 1H); 7.28-7.54 (m, 14H).

Example 25H tert-Butyl (2R)-(Benzyloxymethyl)-2-[3(S)-(4(S)-phenyloxazolidin-2-on-3-yl)-4(R)-(2-styryl)azetidin-2-on-1-yl]

acetate. The imine prepared from 0.329 g (1.31 mmol) of O-(benzyl)-D-serine t-butyl ester (Example 5B) and cinnamaldehyde was combined with 2-(4(S)-phenyloxazolidin-2-on-3-yl)acetyl chloride (Example 1) to give 0.543 g (73%) of Example 25H after flash column chromatography purification (90:10 hexanes/ethyl acetate); $^1$H NMR (CDCl$_3$) δ 1.39 (s, 9H); 3.56 (dd, J=2.7 Hz, J=9.5 Hz, 1H); 3.82 (dd, J=4.8 Hz, J=9.5 Hz, 1H); 4.11 (t, J=8.3 Hz, 1H); 4.21-4.29 (m, 2H); 4.50-4.58 (m, 3H); 4.71-4.78 (m, 2H); 6.19 (dd, J=9.1 Hz, J=16.0 Hz, 1H); 6.49 (d, J=16.0 Hz, 1H); 7.07-7.11 (m, 1H); 7.19-7.40 (m, 14H).

Example 25I tert-Butyl 2(S)-(2-(4-cyclohexylpiperazinylcarbonyl)methyl)-2-[3(S)-(4(S)-phenyloxazolidin-2-on-3-yl)-4(R)-(2-styryl)azetidin-2-on-1-yl]acetate. The imine prepared from 0.3 g (0.88 mmol) of L-aspartic acid α-t-butyl ester γ-(4-cyclohexyl)piperazinamide and cinnamaldehyde was combined with 2-(4(S)-phenyloxazolidin-2-on-3-yl)acetyl chloride (Example 1) to give 464 mg (80%) of Example 25I as a white solid after flash column chromatography purification (50:50 hexanes/ethyl acetate). Example 25I exhibited an $^1$H NMR spectrum consistent with the assigned structure.

Example 25J tert-Butyl 3(R)-[3(S)-(4(S)-phenyloxazolidin-2-on-3-yl)-3-methyl-4(R)-(styr-2-yl)azetidin-2-on-1-yl]-3-[(3-trifluoromethyl)phenylmethylaminocarbonyl]propanoate. The imine prepared from 0.307 g (0.89 mmol) of D-aspartic acid β-t-butyl ester α-(3-trifluoromethyl)benzylamide (Example 20) and cinnamaldehyde was combined with 2-(4(S)-phenyloxazolidin-2-on-3-yl)propanoyl chloride (Example 1E) to give 120 mg (20%) after flash column chromatography purification (hexanes 70%/EtOAc 30%); $^1$H NMR (CDCl$_3$) δ 1.25 (s, 3H), 1.38 (s, 9H); 3.09 (dd, J=3.0 Hz, J=18.0 Hz, 1H); 3.33 (dd, J=12.5 Hz, J=18.0 Hz, 1H); 4.01 (dd, J=3.0 Hz, J=11.5 Hz, 1H); 4.04 (dd, J=3.5 Hz, J=8.8 Hz, 1H); 4.42 (d, J=9.0 Hz, 1H); 4.45-4.51 (m, 3H); 4.61-4.66 (m, 1H); 4.75 (dd, J=3.5 Hz, J=8.5 Hz, 1H); 6.23 (dd, J=9.0 Hz, J=15.5 Hz, 1H); 6.78 (d, J=15.5 Hz, 1H); 7.23-7.53 (m, 13H); 7.64 (s, 1H).

Example 25K

2(R)-(tert-Butoxycarbonylmethyl)-2-[3(S)-(4(S)-phenyloxazolidin-2-on-3-yl)-4(R)-(prop-1-enyl)azetidin-2-on-1-yl]acetic acid N-(3-trifluoromethylbenzyl)amide. The imine prepared from 0.289 g (0.83 mmol) of D-aspartic acid β-t-butyl ester α-(3-trifluoromethyl)benzylamide and crotonaldehyde was combined with 2-(4(S)-phenyloxazolidin-2-on-3-yl)acetyl chloride (Example 1) to give 381 mg (76%) of Example 25K after flash column chromatography purification (99:1 CH$_2$Cl$_2$/MeOH); $^1$H NMR (CDCl$_3$) δ 1.36 (s, 9H), 1.69 (dd, J=2 Hz, J=6.5 Hz, 3H); 3.08 (dd, J=3.3 Hz, J=17.8 Hz, 1H); 3.18 (dd, J=11 Hz, J=17.5 Hz, 1H); 3.94 (dd, J=3.5 Hz, J=11 Hz, 1H); 4.12 (d, J=5 Hz, 1H); 4.15 (dd, J=7 Hz, J=8 Hz, 1H); 4.35 (dd, J=4.8 Hz, J=9.8 Hz, 1H); 4.44 (dd, J=6 Hz, J=15 Hz, 1H); 4.61 (dd, J=6 Hz, J=15 Hz, 1H); 4.67-4.75 (m, 2H); 5.52-5.58 (m, 1H); 5.92-6.00 (m, 1H); 7.33-7.60 (m, 9H); 8.47-8.50 (m, 1H).

Example 25O

Methyl 2(S)-(tert-Butoxycarbonylethyl)-2-[3(S)-(4(S)-phenyloxazolidin-2-on-3-yl)-4(R)-(2-styryl)azetidin-2-on-1-yl]acetate. The imine prepared from 433 mg (1.99 mmol) of L-glutamic acid γ-t-butyl ester α-methyl ester and cinnamaldehyde was combined with 2-(4(S)-phenyloxazolidin-2-on-3-yl)acetyl chloride (Example 1) to give 682 mg (64%) of Example 25O after flash column chromatography purification (70:30 hexanes/ethyl acetate); $^1$H NMR (CDCl$_3$) δ 1.32 (s, 9H); 2.10-2.26 (m, 1H); 2.30-2.41 (m, 3H); 3.66 (s, 3H); 3.95-3.99 (m, 1H); 4.16 (dd, J=7.5 Hz, J=9 Hz, 1H); 4.38 (dd, J=5 Hz, J=9 Hz, 1H); 4.55 (d, J=5 Hz 1H); 4.61 (t, J=9 Hz, 1H); 4.86 (dd, J=7.5 Hz, J=9 Hz, 1H); 6.00 (dd, J=9 Hz, J=16 Hz, 1H); 6.60 (d, J=16 Hz, 1H); 7.26-7.43 (m, 10H).

Example 25M tert-Butyl 2(S)-(methoxycarbonylethyl)-2-[3(S)-(4(S)-phenyloxazolidin-2-on-3-yl)-4(R)-(2-styryl)azetidin-2-on-1-yl]acetate. The imine prepared from 428 mg (1.97 mmol) of L-glutamic acid γ-t-butyl ester α-methyl ester and cinnamaldehyde was combined with 2-(4(S)-phenyloxazolidin-2-on-3-yl)acetyl chloride (Example 1) to give 864 mg (82%) of Example 25M after flash column chromatography purification (70:30 hexanes/ethyl acetate); $^1$H NMR (CDCl$_3$) δ 1.40 (s, 9H); 2.12-2.27 (m, 1H); 2.32-2.55 (m, 3H); 3.50 (s, 3H); 3.72 (dd, J=4.6 Hz, J=10.4 Hz, 1H); 4.12-4.17 (m, 1H); 4.34 (dd, J=5 Hz, J=9 Hz, 1H); 4.50 (d, J=5 Hz, 1H); 4.60 (t, J=8.9 Hz, 1H); 4.81-4.86 (m, 1H); 6.06 (dd, J=9 Hz, J=16 Hz, 1H); 6.59 (d, J=16 Hz, 1H); 7.25-7.42 (m, 10H).

Example 25P

Methyl 2(S)-(tert-Butoxycarbonylmethyl)-2-[3(S)-(4(S)-phenyloxazolidin-2-on-3-yl)-4(R)-(2-styryl)azetidin-2-on-1-yl]acetate. The imine prepared from 424 mg (2.09 mmol) of L-aspartic acid γ-t-butyl ester α-methyl ester and cinnamaldehyde was combined with 2-(4(S)-phenyloxazolidin-2-on-3-yl)acetyl chloride (Example 1) to give 923 mg (85%) of Example 25P after recrystallization from CH$_2$Cl$_2$/hexanes; $^1$H NMR (CDCl$_3$) δ 1.41 (s, 9H); 2.77 (dd, J=7.5 Hz, J=16.5 Hz, 1H); 3.00 (dd, J=7 Hz, J=16.5 Hz, 1H); 4.16 (dd, J=7.5 Hz, J=9 Hz, 1H); 4.41-48 (m, 2H); 4.55 (d, J=5 Hz, 1H); 4.60 (t, J=8.8 Hz, 1H); 4.86 (dd, J=7.5 Hz, J=9 Hz, 1H); 5.93 (dd, J=9.5 Hz, J=15.5 Hz, 1H); 6.61 (d, J=15.5 Hz, 1H); 7.25-7.43 (m, 10H).

Example 25L

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N—[(R)-1-(3-trifluoromethylphenyl)ethyl] amide. The imine prepared from 160 mg (0.44 mmol) of D-aspartic acid β-t-butyl ester α-[(R)-1-(3-trifluoromethylphenyl)ethyl]amide and cinnamaldehyde was combined with 2-(4(S)-phenyloxazolidin-2-on-3-yl)acetyl chloride (Example 1) to give 166 mg (55%) of Example 25L after flash column chromatography purification (70:30 hexanes/EtOAc). Example 25L exhibited an $^1$H NMR spectrum consistent with the assigned structure.

Example 25N

2(R)-(tert-Butoxycarbonylmethyl)-2-[3(S)-(4(S)-phenyloxazolidin-2-on-3-yl)-4(R)-(2-styryl)azetidin-2-on-1-yl] acetic acid N—[(S)-1-(3-trifluoromethylphenyl)ethyl] amide. The imine prepared from 120 mg (0.22 mmol) of D-aspartic acid β-t-butyl ester α-[(S)-1-(3-trifluoromethylphenyl)ethyl]amide and cinnamaldehyde was combined with 2-(4(S)-phenyloxazolidin-2-on-3-yl)acetyl chloride (Example 1) to give 75 mg (50%) of Example 25N after flash column chromatography purification (70:30 hexanes/EtOAc). Example 25N exhibited an $^1$H NMR spectrum consistent with the assigned structure.

Example 25Q

Methyl 2(R)-(2-(3-trifluoromethylbenzyl)amincarbonyl)ethyl)-2-[3(S)-(4(S)-phenyloxazolidin-2-on-3-yl)-4(R)-(2-styryl)azetidin-2-on-1-yl]acetate. The imine prepared from 517 mg (1.62 mmol) of D-glutamic acid α-methyl ester γ-(3-trifluoromethyl)benzylamide and cinnamaldehyde was combined with 2-(4(S)-phenyloxazolidin-2-on-3-yl)acetyl chloride (Example 1) to give 527 mg (51%) of Example 25Q after flash column chromatography purification (50:50 hexanes/EtOAc). Example 25Q exhibited an $^1$H NMR spectrum consistent with the assigned structure.

The following compounds were prepared according to the processes described herein:

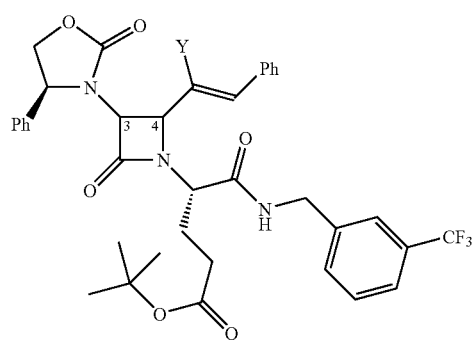

| Example | Y | C(3)-C(4) Stereochemistry |
|---|---|---|
| 25R | F | (3S,4R) |
| 25S | F | not determined |
| 25T | Br | not determined |
| 25U | Br | not determined |

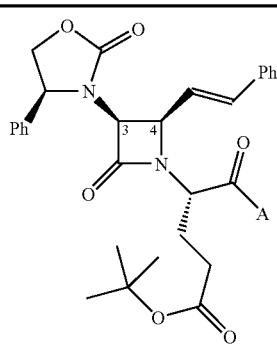

| Example | A |
|---|---|
| 25V | (R)-1,2,3,4-tetrahydro-1-naphtylamide |
| 25W | 1-phenyl-cyclopentylamide |

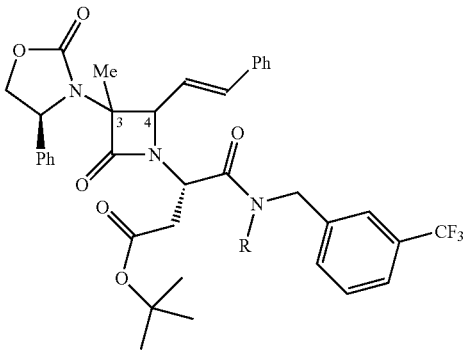

| Example | C(3)-C(4) Stereochemistry | R |
|---|---|---|
| 25X | (3S)-cis | Me |
| 25Y | not determined | H |

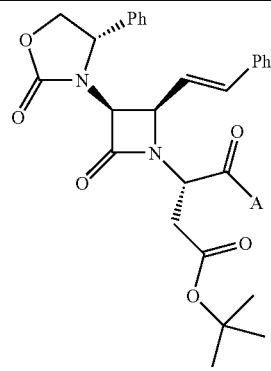

| Example | A |
|---|---|
| 25Z | 1-phenyl-cyclopent-1-ylamino |
| 25AA | (R)-1-phenylethy-1-amino |

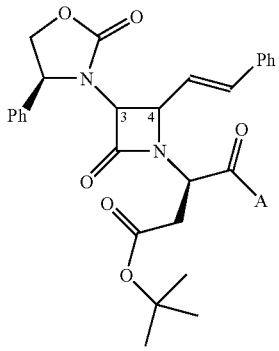

| Example | C(3)-C(4) Stereochemistry | A | A' |
|---|---|---|---|
| 25AB | (3S,4R) | α,α-dimethylbenzylamino | t-butyl ester |
| 25AC | not determined | N-methyl-3-CF3-benzylamino | t-butyl ester |
| 25AD | not determined | (R)-α-methylbenzylamino | t-butyl ester |
| 25AE | (3S,4R) | (R)-α,N-dimethylbenzylamino | t-butyl ester |

Example 25AF t-Butyl 2(S)-(2-(3-trifluoromethylbenzyl)aminocarbonyl)ethyl)-2-[3(S)-(4(S)-phenyloxazolidin-2-on-3-yl)-4(R)-(2-styryl)azetidin-2-on-1-yl]acetate.

Example 26

General procedure for hydrolysis of a tert-butyl ester. A solution of tert-butyl ester derivative in formic acid, typically 1 g in 10 mL, is stirred at ambient temperature until no more ester is detected by thin layer chromatography (dichloromethane 95%/methanol 5%), a typical reaction time being around 3 hours. The formic acid is evaporated under reduced pressure; the resulting solid residue is partitioned between dichloromethane and saturated aqueous sodium bicarbonate. The organic layer is evaporated to give an off-white solid that may be used directly for further reactions, or recrystallized from an appropriate solvent system if desired.

Examples 27-34AE were prepared from the appropriate tert-butyl ester according to the procedure used in Example 26.

Example 27

2(R,S)-(Carboxy)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 18 (0.30 g, 0.46 mmol) was hydrolyzed to give 0.27 g (quantitative yield) of Example 27 as an off-white solid; $^1$H NMR (CDCl$_3$) δ 4.17-5.28 (m, 9H); 6.21-6.29 (m, 1H), 6.68-6.82 (m, 1H); 7.05-7.75 (m, 13H); 9.12-9.18 (m, 1H).

Example 28

2(S)-(Carboxymethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 19 (1.72 g, 2.59 mmol) was hydrolyzed to give 1.57 g (quantitative yield) of Example 28 as an off-white solid; $^1$H NMR (CDCl$_3$) δ 2.61 (dd, J=9.3 Hz, J=16.6 Hz, 1H); 3.09-3.14 (m, 1H); 4.10-4.13 (m, 1H); 4.30 (d, J=4.5 Hz, 1H); 4.39-4.85 (m, 6H); 6.20 (dd, J=9.6 Hz, J=15.7 Hz, 1H); 6.69 (d, J=15.8 Hz, 1H); 7.12-7.15 (m, 2H); 7.26-7.50 (m, 11H); 7.61 (s, 1H); 8.41-8.45 (m, 1H).

Example 28A

2(S)-(Carboxymethyl)-2-[3(R)-(4(R)-phenyloxazolidin-2-on-3-yl)-4(S)-(2-styryl)azetidin-2-on-1-yl]acetic acid N-(3-trifluoromethylbenzyl)amide. Example 19A (41 mg, 0.06 mmol) was hydrolyzed to give 38 mg (quantitative yield) of Example 28A as an off-white solid; $^1$H NMR (CDCl$_3$) δ 2.26 (d, J=7 Hz, 1H); 4.03 (t, J=7 Hz, 1H); 4.16 (t, J=8 Hz, 1H); 4.26 (d, J=4.3 Hz, 1H); 4.46 (dd, J=5.7 Hz, J=15.1, 1H); 4.53-4.75 (m, 5H); 6.25 (dd, J=9.5 Hz, J=15.7 Hz, 1H); 6.77 (d, J=15.7 Hz, 1H); 7.28-7.53 (m, 13H); 7.64 (s, 1H); 8.65-8.69 (m, 1H).

Example 29

2(S)-(Carboxyethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 20 (4.97 g, 7.34 mmol) was hydrolyzed to give 4.43 g (97%) of Example 29 as an off-white solid; $^1$H NMR (CDCl$_3$) δ 1.92-2.03 (m, 1H); 2.37-2.51 (m, 3H); 4.13-4.19 (m, 1H); 3.32 (d, J=4.9 Hz, 1H); 4.35-4.39 (m, 1H); 4.44 (dd, J=5.9 Hz, J=14.9 Hz, 1H); 4.50-4.57 (m, 2H); 4.61-4.67 (m, 1H); 4.70-4.76 (m, 1H); 6.24 (dd, J=9.6 Hz, J=15.8 Hz, 1H); 6.70 (d, J=15.8 Hz, 1H); 7.18-7.47 (m, 14H).

Example 30

2(S)-(Carboxymethyl)-2-[3(S)-(4(S)-phenyloxazolidin-2-on-3-yl)-4(R)-(2-styryl)azetidin-2-on-1-yl]acetic acid N-[4-(2-phenylethyl)]piperazinamide. Example 21 (1.88 g, 2.78 mmol) was hydrolyzed to give 1.02 g (60%) of Example 30 as an off-white solid; $^1$H NMR (CDCl$_3$) δ 2.63 (dd, J=6.0 Hz, J=16.5 Hz, 1H); 2.75-2.85 (m, 1H); 3.00 (dd, J=8.2 Hz, J=16.6 Hz, 1H); 3.13-3.26 (m, 4H); 3.37-3.56 (m, 4H); 3.86-4.00 (m, 1H); 4.05-4.11 (m, 1H); 4.24 (d, J=5.0 Hz, 1H); 4.46-4.66 (m, 1H); 4.65-4.70 (m, 1H); 5.10-5.15 (m, 1H); 6.14 (dd, J=9.3 Hz, J=15.9 Hz, 1H); 6.71 (d, J=15.9 Hz, 1H); 7.22-7.41 (m, 15H); 12.02 (s, 1H).

Example 31

2(S)-(Carboxyethyl)-2-[3(S)-(4(S)-phenyloxazolidin-2-on-3-yl)-4(R)-(2-styryl)azetidin-2-on-1-yl]acetic acid N-[4-(2-phenylethyl)]piperazinamide. Example 22 (0.383 g, 0.55 mmol) was hydrolyzed to give 0.352 g (quantitative yield) of Example 31 as an off-white solid; $^1$H NMR (CDCl$_3$) δ 1.93-2.01 (m, 1H); 2.07-2.36 (m, 6H); 2.82-2.90 (m, 1H); 3.00-3.20 (m, 4H); 3.36-3.54 (m, 4H); 3.74-3.82 (m, 1H); 4.06-4.11 (m, 1H); 4.29 (d, J=4.9 Hz, 1H); 4.33-4.46 (m, 2H); 4.50-4.58 (m, 2H); 4.67-4.72 (m, 1H); 4.95-5.00 (m, 1H); 6.18 (dd, J=9.2 Hz, J=16.0 Hz, 1H); 6.67 (d, J=15.9 Hz, 1H); 7.19-7.42 (m, 15H); 8.80 (brs, 1H).

Example 32

2(R)-(Carboxymethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 23 (1.51 g, 2.27 mmol) was hydrolyzed to give 1.38 g (quantitative yield) of Example 32 as an off-white solid.

Example 32A

2(R)-(Carboxymethyl)-2-[3(R)-(4(R)-phenyloxazolidin-2-on-3-yl)-4(S)-(2-styryl)azetidin-2-on-1-yl]acetic acid N-(3-trifluoromethylbenzyl)amide. Example 23A (550 mg, 0.83 mmol) was hydrolyzed to give 479 mg (95%) of Example 32A as an off-white solid. Example 32A exhibited an $^1$H NMR spectrum consistent with the assigned structure.

Example 33

2(R)-(Carboxyethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 24 (0.604 g, 0.89 mmol) was hydrolyzed to give 0.554 g (quantitative yield) of Example 33 as an off-white solid.

Example 34

2(S)-(Carboxyethyl)-2-[3(S)-(4(S)-phenyloxazolidin-2-on-3-yl)-4(R)-(2-styryl)azetidin-2-on-1-yl]acetic acid N-(4-cyclohexyl)piperazinamide. Example 25 (0.537 g, 0.80 mmol) was hydrolyzed to give 0.492 g (quantitative yield) of Example 34 as an off-white solid; $^1$H NMR (CDCl$_3$) δ 1.09-1.17 (m, 1H); 1.22-1.33 (m, 2H); 1.40-1.47 (m, 2H); 1.63-1.67 (m, 1H); 1.85-1.90 (m, 2H); 1.95-2.00 (m, 1H);

2.05-2.15 (m, 3H); 2.20-2.24 (m, 1H); 2.30-2.36 (m, 1H); 2.85-2.93 (m, 1H); 3.25-3.33 (m, 1H); 3.36-3.46 (m, 2H); 3.81-3.87 (m, 1H); 4.08 (t, J=8.3 Hz, 1H); 4.28 (d, J=5.0 Hz, 1H); 4.33-4.56 (m, 4H); 4.70 (t, J=8.3 Hz, 1H); 4.83-4.91 (m, 1H); 6.17 (dd, J=9.1 Hz, J=15.9 Hz, 1H); 6.67 (d, J=15.9 Hz, 1H); 7.25-7.44 (m, 10H); 8.22 (brs, 1H).

Example 34A

2(S)-(2-(4-Cyclohexylpiperazinylcarbonyl)ethyl)-2-[3(S)-(4(S)-phenyloxazolidin-2-on-3-yl)-4(R)-(2-styryl)azetidin-2-on-1-yl]acetic acid. Example 25A (0.787 g, 1.28 mmol) was hydrolyzed to give 0.665 g (92%) of Example 34A as an off-white solid; $^1$H NMR (CDCl$_3$) δ 1.05-1.13 (m, 1H); 1.20-1.40 (m, 5H); 1.60-1.64 (m, 1H); 1.79-1.83 (m, 2H); 2.00-2.05 (m, 2H); 2.22-2.44 (m, 3H); 2.67-2.71 (m, 1H); 2.93-3.01 (m, 4H); 3.14-3.18 (m, 1H); 3.38-3.42 (m, 1H); 3.48-3.52 (m, 1H); 3.64-3.69 (m, 1H); 4.06-4.14 (m, 2H); 4.34-4.43 (m, 2H); 4.56 (t, J=8.8 Hz, 1H); 4.73 (t, J=8.4 Hz, 1H); 6.15 (dd, J=9.1 Hz, J=16.0 Hz, 1H); 6.65 (d, J=16.0 Hz, 1H); 7.25-7.42 (m, 10H).

Example 34B

2(R)-(Carboxymethyl)-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)carboxamide. Example 25B (0.26 g, 0.38 mmol) was hydrolyzed to give 0.238 g (quantitative yield) of Example 34B as an off-white solid; $^1$H NMR (CDCl$_3$) δ 3.27 (d, J=7.2 Hz, 1H); 4.06 (t, J=7.2 Hz, 1H); 4.15 (t, J=8.1 Hz, 1H); 4.27 (d, J=4.8 Hz, 1H); 4.56-4.76 (m, 5H); 6.34 (dd, J=9.5 Hz, J=15.7 Hz, 1H); 6.80 (d, J=15.7 Hz, 1H); 7.06 (t, J=7.7 Hz, 1H); 7.31-7.54 (m, 12H); 8.58 (t, J=5.9 Hz, 1H).

Example 34C

2(R)-(Carboxymethyl)-2-[3(S)-(4(S)-phenyloxazolidin-2-on-3-yl)-4(R)-(2-styryl)azetidin-2-on-1-yl]acetic acid N—[(S)-α-methylbenzyl]amide. Example 25C (0.215 g, 0.35 mmol) was hydrolyzed to give 0.195 g (quantitative yield) of Example 34C as an off-white solid; $^1$H NMR (CDCl$_3$) δ 1.56 (d, J=7.0 Hz, 1H); 3.10 (dd, J=4.5 Hz, J=17.9 Hz, 1H); 3.18 (dd, J=9.8 Hz, J=17.9 Hz, 1H); 4.00 (dd, J=4.5 Hz, J=9.7 Hz, 1H); 4.14 (t, J=8.2 Hz, 1H); 4.26 (d, J=4.7 Hz, 1H); 5.02-5.09 (m, 1H); 6.41 (dd, J=9.4 Hz, J=15.8 Hz, 1H); 6.78 (d, J=15.8 Hz, 1H); 7.18 (t, J=7.3 Hz, 1H); 7.26-7.43 (m, 12H); 8.29 (d, J=8.2 Hz, 1H).

Example 34D

2(R)-(Carboxymethyl)-2-[3(S)-(4(S)-phenyloxazolidin-2-on-3-yl)-4(R)-(2-styryl)azetidin-2-on-1-yl]acetic acid N—[(R)-α-methylbenzyl]amide. Example 25D (0.22 g, 0.35 mmol) was hydrolyzed to give 0.20 g (quantitative yield) of Example 34D as an off-white solid; $^1$H NMR (CDCl$_3$) δ 1.59 (d, J=7.0 Hz, 1H); 3.25 (d, J=7.0 Hz, 2H); 3.92 (t, J=7.3 Hz, 1H); 4.15 (t, J=8.3 Hz, 1H); 4.26 (d, J=5.0 Hz, 1H); 4.52 (dd, J=4.8 Hz, J=9.3 Hz, 1H); 4.65 (t, J=8.8 Hz, 1H); 4.72 (t, J=8.3 Hz, 1H); 5.07-5.28 (m, 1H); 6.29 (dd, J=9.5 Hz, J=15.6 Hz, 1H); 6.71 (d, J=16.0 Hz, 1H); 7.20-7.43 (m, 13H); 8.31 (d, J=8.0 Hz, 1H).

Example 34E

2(R)-(Carboxymethyl)-2-[3(S)-(4(S)-phenyloxazolidin-2-on-3-yl)-4(R)-(2-styryl)azetidin-2-on-1-yl]acetic acid N-methyl-N-(3-trifluoromethylbenzyl)amide. Example 25E (0.253 g, 0.37 mmol) was hydrolyzed to give 0.232 g (quantitative yield) of Example 34E as an off-white solid; $^1$H NMR (CDCl$_3$) δ 3.07-3.15 (m, 4H); 4.13 (t, J=8.2 Hz, 1H); 4.30 (d, J=4.9 Hz, 1H); 4.46-4.78 (m, 5H); 5.23 (dd, J=4.6 Hz, J=9.7 Hz, 1H); 6.20 (dd, J=9.4 Hz, J=15.9 Hz, 1H); 6.73 (d, J=15.9 Hz, 1H); 7.25-7.43 (m, 15H).

Example 34F

2(S)-(Carboxyethyl)-2-[3(S)-(4(S)-phenyloxazolidin-2-on-3-yl)-4(R)-(2-chlorostyr-2-yl)azetidin-2-on-1-yl]acetic acid N-(3-trifluoromethylbenzyl)amide. Example 25F (0.707 g, 0.99 mmol) was hydrolyzed to give 0.648 g (99%) of Example 34F as an off-white solid; $^1$H NMR (CDCl$_3$) δ 2.22-2.28 (m, 2H); 2.49-2.64 (m, 2H); 4.09 (t, J=8.0 Hz, 1H); 4.25-4.62 (m, 6H); 4.87 (t, J=8.0 Hz, 1H); 6.88 (s, 1H); 7.25-7.66 (m, 15H).

Example 34G

2(R)-(Carboxymethyl)-2-[3(S)-(4(S)-phenyloxazolidin-2-on-3-yl)-4(R)-(2'-methoxystyr-2-yl)azetidin-2-on-1-yl]acetic acid N-(3-trifluoromethylbenzyl)amide. Example 25G (0.268 g, 0.39 mmol) was hydrolyzed to give 0.242 g (98%) of Example 34G as an off-white solid; $^1$H NMR (CDCl$_3$) δ 3.26 (d, J=7.1 Hz, 1H); 3.79 (s, 3H); 4.14 (t, J=8.2 Hz, 1H); 4.25 (d, J=4.5 Hz, 1H); 4.51 (dd, J=5.9 Hz, J=15.5 Hz, 1H); 4.53-4.66 (m, 4H); 6.36 (dd, J=9.4 Hz, J=15.8 Hz, 1H); 8.88 (t, J=8.2 Hz, 1H); 6.70 (d, J=15.8 Hz, 1H); 7.18 (d, J=6.5 Hz, 1H); 7.25-7.48 (m, 10H); 7.48 (s, 1H); 8.66-8.69 (m, 1H).

Example 34H (2R)-(Benzyloxymethyl)-2-[3(S)-(4(S)-phenyloxazolidin-2-on-3-yl)-4(R)-(2-styryl)azetidin-2-on-1-yl]acetic acid. Example 25H (0.16 g, 0.28 mmol) was hydrolyzed to give 0.144 g (quantitative yield) of Example 34H as an off-white solid; $^1$H NMR (CDCl$_3$) δ 3.65 (dd, J=4.0 Hz, J=9.5 Hz, 1H); 3.82 (dd, J=5.5 Hz, J=9.5 Hz, 1H); 4.11 (dd, J=7.8 Hz, J=8.8 Hz, 1H); 4.33 (s, 2H); 4.50 (d, J=5.0 Hz, 1H); 4.57 (t, J=9.0 Hz, 1H); 4.67 (dd, J=4.0 Hz, J=5.0 Hz, 1H); 4.69 (dd, J=5.0 Hz, J=9.5 Hz, 1H); 4.75 (t, J=8.0 Hz, 1H); 6.17 (dd, J=9.3 Hz, J=15.8 Hz, 1H); 6.55 (d, J=16.0 Hz, 1H); 7.09-7.12 (m, 2H); 7.19-7.42 (m, 13H).

Example 34I

2(S)-(2-(4-Cyclohexylpiperazinylcarbonyl)methyl)-2-[3(S)-(4(S)-phenyloxazolidin-2-on-3-yl)-4R)-(2-styryl)azetidin-2-on-1-yl]acetic acid. Example 25I (737 mg, 1.12 mmol) was hydrolyzed to give 640 mg (95%) of Example 34I as an off-white solid. Example 34I exhibited an $^1$H NMR spectrum consistent with the assigned structure.

Example 34J

3(R)-[3(S)-(4(S)-Phenyloxazolidin-2-on-3-yl)-3-methyl-4(R)-(styr-2-yl)azetidin-2-on-1-yl]-3-[(3-trifluoromethyl)phenylmethylaminocarbonyl]propanoic acid. Using the general method of Example 26, 120 mg (0.18 mmol) of Example 25J was hydrolyzed to give 108 mg (98%) of Example 34J as an off-white solid; $^1$H NMR (CDCl$_3$) δ 1.22 (s, 3H); 3.25 (dd, J=3.5 Hz, J=18.0 Hz, 1H); 3.36 (d, J=10.8 Hz, J=18.2 Hz, 1H); 4.01 (dd, J=4.0 Hz, J=10.5 Hz, 1H); 4.05 (dd, J=3.8 Hz, J=8.8 Hz, 1H); 4.33 (d, J=9.0 Hz, 1H);

4.44-4.51 (m, 3H); 4.61-4.66 (m, 1H); 4.73 (dd, J=3.8 Hz, J=8.8 Hz, 1H); 6.19 (dd, J=9.0 Hz, J=16.0 Hz, 1H); 6.74 (d, J=16.0 Hz, 1H); 7.22-7.54 (m, 13H); 7.65 (s, 1H).

Example 34K

2(R)-(Carboxymethyl)-2-[3(S)-(4(S)-phenyloxazolidin-2-on-3-yl)-4(R)-(propen-1-yl)azetidin-2-on-1-yl]acetic acid N-(3-trifluoromethylbenzyl)amide. Using the general method of Example 26, 160 mg (0.27 mmol) of Example 25K was hydrolyzed to give 131 mg (90%) of Example 34K as an off-white solid. $^1$H NMR (CDCl$_3$) δ 1.69 (dd, J=1 Hz, J=6.5 Hz, 3H); 3.23 (d, J=7 Hz, 1H); 3.93 (t, J=7.3 Hz, 1H); 4.14-4.20 (m, 3H); 4.29 (dd, J=5 Hz, J=9.5 Hz, 1H); 4.43 (dd, J=6 Hz, J=15 Hz, 1H); 4.61 (dd, J=6.5 Hz, J=15 Hz, 1H); 4.66-4.74 (m, 2H); 5.50-5.55 (m, 1H); 5.90-5.98 (m, 1H); 7.32-7.60 (m, 9H); 8.60-8.64 (m, 1H).

Example 34L

2(R)-(Carboxylmethyl)-2-[3(S)-(4(S)-phenyloxazolidin-2-on-3-yl)-4(R)-(2-styryl)azetidin-2-on-1-yl]acetic acid N—[(R)-1-(3-trifluoromethylphenyl)ethyl]amide. Example 25L (166 mg, 0.24 mmol) was hydrolyzed to give 152 mg (quantitative yield) of Example 34L as an off-white solid; and exhibited an $^1$H NMR spectrum consistent with the assigned structure.

Example 34M

2(S)-(Methoxycarbonylethyl)-2-[3(S)-(4(S)-phenyloxazolidin-2-on-3-yl)-4(R)-(2-styryl)azetidin-2-on-1-yl]acetic acid. Example 25M (875 mg, 1.64 mmol) was hydrolyzed to give 757 mg (97%) of Example 34M as an off-white solid, and exhibited an $^1$H NMR spectrum consistent with the assigned structure.

Example 34N

2(R)-(Carboxylmethyl)-2-[3(S)-(4(S)-phenyloxazolidin-2-on-3-yl)-4(R)-(2-styryl)azetidin-2-on-1-yl]acetic acid N—[(S)-1-(3-trifluoromethylphenyl)ethyl]amide. Example 25N (38.5 mg, 0.057 mmol) was hydrolyzed to give 35 mg (quantitative yield) of Example 34N as an off-white solid, and exhibited an $^1$H NMR spectrum consistent with the assigned structure.

Example 34O

2(S)-(tert-Butoxycarbonylethyl)-2-[3(S)-(4(S)-phenyloxazolidin-2-on-3-yl)-4(R)-(2-styryl)azetidin-2-on-1-yl]acetic acid. Example 25O (97 mg, 0.18 mmol) was dissolved in methanol/tetrahydrofuran (2.5 mL/2 mL) and reacted with lithium hydroxide (0.85 mL of a 0.85M solution in water; 0.72 mmol) for 6 hours at room temperature. The reaction was diluted with 15 mL dichloromethane and aqueous hydrochloric acid (1M) was added until the pH of the aqueous layer reached 5 (as measured by standard pH paper). The organic layer was then separated and evaporated to dryness to give 84 mg (89%) of Example 34O as an off-white solid, and exhibited an $^1$H NMR spectrum consistent with the assigned structure.

Example 34P

2(S)-(tert-Butoxycarbonylethyl)-2-[3(S)-(4(S)-phenyloxazolidin-2-on-3-yl)-4(R)-(2-styryl)azetidin-2-on-1-yl]acetic acid. Example 25P (200 mg, 0.39 mmol) was hydrolyzed according to the method used for Example 34O to give 155 mg (88%) of Example 34P as an off-white solid; and exhibited an $^1$H NMR spectrum consistent with the assigned structure.

Example 34Q

2(R)-(2-(3-trifluoromethylbenzyl)amino-1-ylcarbonyl)ethyl)-2-[3(S)-(4(S)-phenyloxazolidin-2-on-3-yl)-4(R)-(2-styryl)azetidin-2-on-1-yl]acetic acid. Example 25Q (150 mg, 0.24 mmol) was hydrolyzed according to the method used for Example 34O to give 143 mg (97%) of Example 34Q as an off-white solid, and exhibited an $^1$H NMR spectrum consistent with the assigned structure.

Example 34R

2(R)-(tert-Butoxycarbonylmethyl)-2-[3(RS)-2-thienylmethyl)-4(R)-(2-styryl)azetidin-2-on-1-yl]acetic acid N-(3-trifluoromethylbenzyl)amide. The imine prepared from 290 mg (0.84 mmol) of D-aspartic acid β-t-butyl ester α-(3-trifluoromethyl)benzylamide and cinnamaldehyde was combined with 2-thiophene-acetyl chloride to give 42 mg (8%) of Example 34R after flash column chromatography purification (70:30 hexanes/ethyl acetate), and exhibited an $^1$H NMR spectrum consistent with the assigned structure.

The following compounds were prepared according to the processes described herein:

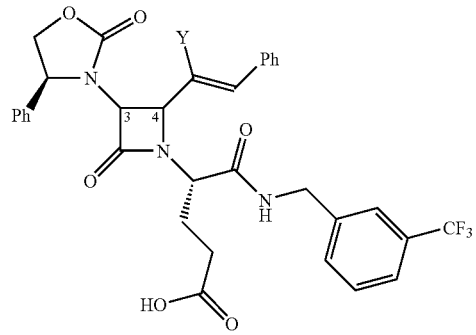

| Example | Y | C(3)-C(4) Stereochemistry |
|---|---|---|
| 34S | F | (3S,4R) |
| 34T | F | not determined |
| 34U | Br | not determined |

| Example | A |
|---|---|
| 34V | (R)-1,2,3,4-tetrahydro-1-naphtylamide |
| 34W | 1-phenyl-cyclopentylamide |

| Example | C(3)-C(4) Stereochemistry | R |
|---|---|---|
| 34X | (3S,4R) | Me |
| 34Y | not determined | H |

| Example | A |
|---|---|
| 34Z | 1-phenyl-cyclopent-1-ylamino |
| 34AA | (R)-1-phenylethy-1-amino |

| Example | C(3)-C(4) Stereochemistry | A |
|---|---|---|
| 34AB | (3S,4R) | α,α-dimethylbenzylamino |
| 34AC | not determined | N-methyl-3-CF3-benzylamino |
| 34AD | not determined | (R)-α-methylbenzylamino |
| 34AE | (3S,4R) | (R)-α,N-dimethylbenzylamino |

Examples 36-42A, shown in the following Table, were prepared using the procedure of Example 6, except that N-benzyloxycarbonyl-D-aspartic acid β-t-butyl ester monohydrate was replaced with Example 27, and 3-(trifluoromethyl)benzyl amine was replaced with the appropriate amine; all listed Examples exhibited an ¹H NMR spectrum consistent with the assigned structure.

| Example | A' |
|---|---|
| 36 | 2-(piperidinyl)ethylamino |
| 37 | 4-(piperidinyl)piperidinyl |
| 38 | 4-(2-phenylethyl)piperazinyl |
| 39 | 1-benzylpiperidin-4-ylamino |
| 40 | 4-butylpiperazinyl |
| 41 | 4-isopropylpiperazinyl |
| 42 | 4-cyclohexylpiperazinyl |
| 42A | 4-[2-(piperidinyl)ethyl]piperidinyl |

Examples 43-86A, shown in the following Table, were prepared using the procedure of Example 6, except that N-benzyloxycarbonyl-D-aspartic acid β-t-butyl ester monohydrate was replaced with Example 28, and 3-(trifluoromethyl)benzyl amine was replaced with the appropriate amine; all listed Examples exhibited an ¹H NMR spectrum consistent with the assigned structure.

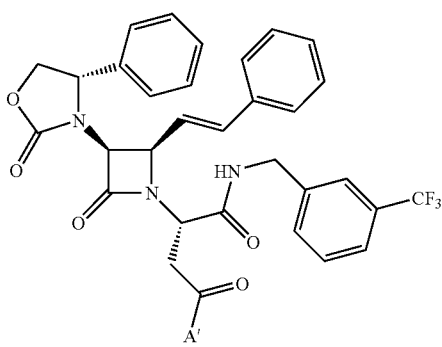

| Example | A' |
|---|---|
| 43 | 2-(piperidinyl)ethylamino |
| 44 | 4-(piperidinyl)piperidinyl |
| 45 | 4-(phenylethyl)piperazinyl |
| 46 | fur-2-ylmethylamino |
| 47 | 4-(pyrrolidinyl)piperazinyl |
| 48 | 4-(3-trifluoromethylphenyl)piperazinyl |
| 49 | 4-(benzyloxycarbonyl)piperazinyl |
| 50 | 4-[2-(2-hydroxyethoxy)ethyl]piperazinyl |
| 51 | 4-benzylpiperazinyl |
| 52 | 4-(3,4-methylenedioxybenzyl)piperazinyl |
| 53 | 4-phenylpiperazinyl |
| 54 | 4-(3-phenylprop-2-enyl)piperazinyl |
| 55 | 4-ethylpiperazinyl |
| 56 | 2-(dimethylamino)ethylamino |
| 57 | 4-(pyrrolidinylcarbonylmethyl)piperazinyl |
| 58 | 4-(1-methylpiperidin-4-yl)piperazinyl |
| 59 | 4-butylpiperazinyl |
| 60 | 4-isopropylpiperazinyl |
| 61 | 4-pyridylmethylamino |
| 62 | 3-(dimethylamino)propylamino |
| 63 | 1-benzylpiperidin-4-ylamino |
| 64 | N-benzyl-2-(dimethylamino)ethylamino |
| 65 | 3-pyridylmethylamino |
| 66 | 4-(cyclohexyl)piperazinyl |
| 67 | 4-(2-cyclohexylethyl)piperazinyl |
| 68 | 4-[2-(morpholin-4-yl)ethyl]piperazinyl |
| 69 | 4-(4-tert-butylbenzyl)piperazinyl |
| 70 | 4-[2-(piperidinyl)ethyl]piperazinyl |
| 71 | 4-[3-(piperidinyl)propyl]piperazinyl |
| 72 | 4-[2-(N,N-dipropylamino)ethyl]piperazinyl |
| 73 | 4-[3-(N,N-diethylamino)propyl]piperazinyl |
| 74 | 4-[2-(dimethylamino)ethyl]piperazinyl |
| 75 | 4-[3-(pyrrolidinyl)propyl]piperazinyl |
| 76 | 4-(cyclohexylmethyl)piperazinyl |
| 77 | 4-cyclopentylpiperazinyl |
| 78 | 4-[2-(pyrrolidinyl)ethyl]piperazinyl |
| 79 | 4-[2-(thien-2-yl)ethyl]piperazinyl |
| 80 | 4-(3-phenylpropyl)piperazinyl |
| 81 | 4-[2-(N,N-diethylamino)ethyl]piperazinyl |
| 82 | 4-benzylhomopiperazinyl |
| 83 | 4-(bisphenylmethyl)piperazinyl |
| 84 | 3-(4-methylpiperazinyl)propylamino |
| 85 | (+)-3(S)-1-benzylpyrrolidin-3-ylamino |
| 86 | 2-pyridylmethylamino |
| 86A | 4-[2-(piperidinyl)ethyl]piperidinyl |
| 86B | 1-benzylpiperidin-4-ylamino N-oxide |

Example 86B

Example 63 (44 mg, 0.06 mmol) was dissolved in 4 mL dichloromethane and reacted with 3-chloroperoxybenzoic acid (12 mg, 0.07 mmol) until the reaction was complete as assessed by TLC (dichloromethane 94%/methanol 6%, UV detection). The reaction was quenched with aqueous sodium sulfite, the dichloromethane layer was washed with 5% aqueous sodium bicarbonate and distilled water. Evaporation of the dichloromethane layer afforded Example 86B as an off-white solid (35 mg, 78%), and exhibited an $^1$H NMR spectrum consistent with the assigned structure.

Examples 121-132, shown in The following table, were prepared using the procedure of Example 6, except that N-benzyloxycarbonyl-D-aspartic acid β-t-butyl ester monohydrate was replaced with Example 30, and 3-(trifluoromethyl)benzyl amine was replaced with the appropriate amine; all listed Examples exhibited an $^1$H NMR spectrum consistent with the assigned structure.

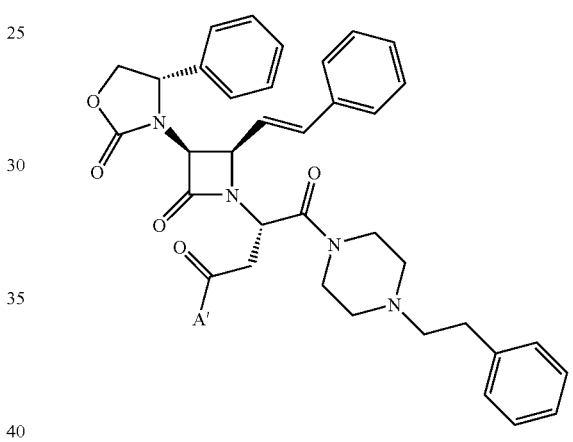

| Example | A' |
|---|---|
| 121 | 3-trifluoromethylbenzylamino |
| 122 | morpholin-4-ylamino |
| 123 | 2-(dimethylamino)ethylamino |
| 124 | 3-(dimethylamino)propylamino |
| 125 | cyclohexylamino |
| 126 | piperidinyl |
| 127 | 2-methoxyethylamino |
| 128 | isopropylamino |
| 129 | isobutylamino |
| 130 | ethylamino |
| 131 | dimethylamino |
| 132 | methylamino |

Examples 132A-132B, shown in the following Table, were prepared using the procedure of Example 6, except that N-benzyloxycarbonyl-D-aspartic acid β-t-butyl ester monohydrate was replaced with Example 34I, and 3-(trifluoromethyl)benzyl amine was replaced with the appropriate amine; all listed Examples exhibited an $^1$H NMR spectrum consistent with the assigned structure.

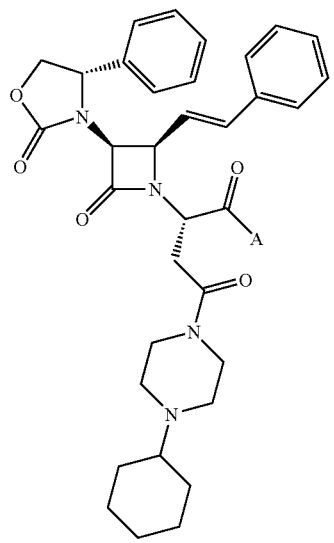

| Example | A |
|---|---|
| 132A | (2,3-dichlorobenzyl)amino |
| 132B | 1-phenylcyclohexylamino |

Example 132C

2(S)-(tert-Butoxycarbonylmethyl)-2-[3(S)-(4(S)-phenyloxazolidin-2-on-3-yl)-4(R)-(2-styryl)azetidin-2-on-1-yl]acetic acid N-(4-cyclohexyl)piperazinamide. Example 132C was prepared using the procedure of Example 6, except that N-benzyloxycarbonyl-D-aspartic acid β-t-butyl ester monohydrate was replaced with Example 34P, and 3-(trifluoromethyl)benzyl amine was replaced with 1-cyclohexylpiperazine. Example 132C exhibited an $^1$H NMR spectrum consistent with the assigned structure.

The compounds shown in the following Table were prepared according to the processes described herein.

| Example | A | A' |
|---|---|---|
| 132D | 1-phenyl-cyclopent-1-ylamino | 4-(piperidinyl)piperidinyl |
| 132E | 1-phenyl-cyclopent-1-ylamino | 1-benzylpiperidin-4-ylamino |
| 132F | (R)-1-phenylethy-1-amino | 4-(piperidinyl)piperidinyl |

Examples 133-134G, shown in the following Table, were prepared using the procedure of Example 6, except that N-benzyloxycarbonyl-D-aspartic acid β-t-butyl ester monohydrate was replaced with Example 32, and 3-(trifluoromethyl)benzyl amine was replaced with the appropriate amine; all listed Examples exhibited an $^1$H NMR spectrum consistent with the assigned structure.

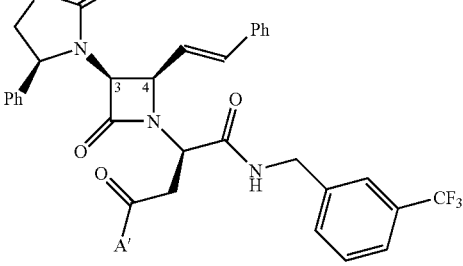

| Example | A' |
|---|---|
| 133 | 4-(piperidinyl)piperidinyl |
| 134 | 4-(2-phenylethyl)piperazinyl |
| 134A | 4-[2-(piperidinyl)ethyl]piperidinyl |
| 134B | 4-(pyrrolidinyl)piperazinyl |
| 134C | 1-benzylpiperidin-4-ylamino |
| 134D | (pyridin-3-ylmethyl)amino |
| 134E | 3-(dimethylamino)propylamino |
| 134F | 3-(S)-(1-benzylpyrrolidin-3-yl)amino |
| 134G | 4-[(piperidinyl)methyl]piperidinyl |
| 134H | 4-(piperidinyl)piperidinyl N-oxide |

Example 134H

Example 134H was prepared using the procedure of Example 86B, except that Example 133 was replaced with Example 110. Example 134H was obtained as an off-white solid (48 mg, 94%), and exhibited an $^1$H NMR spectrum consistent with the assigned structure.

Example 134I

2(R)-[[4-(Piperidinyl)piperidinyl]carboxymethyl]-2-[3(S)-(4(R)-phenyloxazolidin-2-on-3-yl)-4(R)-(2-styryl)azetidin-2-on-1-yl]acetic acid N-(3-trifluoromethylbenzyl)amide. Example 134I was prepared using the procedure of Example 6, except that N-benzyloxycarbonyl-D-aspartic acid β-t-butyl ester monohydrate was replaced with Example 32A, and 3-(trifluoromethyl)benzyl amine was replaced with 4-(piperidinyl)piperidine, and exhibited an $^1$H NMR spectrum consistent with the assigned structure.

The compounds shown in the following Table were prepared according to the processes described herein.

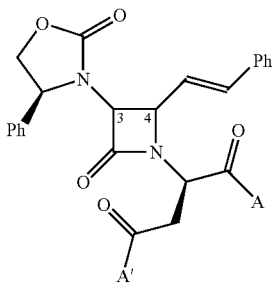

| Example | C(3)-C(4) Stereochemistry | A | A' |
| --- | --- | --- | --- |
| 134J | (3S,4R) | α,α-dimethylbenzylamino | 4-(piperidinyl)piperidinyl |
| 134K | (3S,4R) | α,α-dimethy1benzylamino | 1-benzylpiperidin-4-ylamino |
| 134L | not determined | N-methyl-3-CF3-benzylamino | 4-(piperidinyl)piperidinyl |
| 134M | (3S,4R) | N-methyl-3-CF3-benzylamino | 3-(pyrrolidinyl)piperidinyl |
| 134N | not determined | (R)-α-methylbenzylamino | 4-(piperidinyl)piperidinyl |
| 134O | (3S,4R) | (R)-αN-dimethylbenzylamino | 4-(piperidinyl)piperidinyl |

Example 222

2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N-(2-fluoro-3-trifluoromethylbenzyl)carboxamide. Example 222 was prepared using the procedure of Example 6, except that N-benzyloxycarbonyl-D-aspartic acid β-t-butyl ester monohydrate was replaced with Example 34B, and 3-(trifluoromethyl)benzyl amine was replaced with 4-(piperidinyl)piperidine; Example 222 exhibited an $^1$H NMR spectrum consistent with the assigned structure.

Example 223

2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N—[(S)-α-methylbenzyl]amide. Example 223 was prepared using the procedure of Example 6, except that N-benzyloxycarbonyl-D-aspartic acid β-t-butyl ester monohydrate was replaced with Example 34C, and 3-(trifluoromethyl)benzyl amine was replaced with 4-(piperidinyl)piperidine; Example 223 exhibited an $^1$H NMR spectrum consistent with the assigned structure.

Example 224

2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N—[(R)-α-methylbenzyl]amide. Example 224 was prepared using the procedure of Example 6, except that N-benzyloxycarbonyl-D-aspartic acid β-t-butyl ester monohydrate was replaced with Example 34D, and 3-(trifluoromethyl)benzyl amine was replaced with 4-(piperidinyl)piperidine; Example 223 exhibited an $^1$H NMR spectrum consistent with the assigned structure.

Example 225

2(R)-[[4-(Piperidinyl)piperidinyl]carbonylmethyl]-2-[3(S)-(4(S)-phenyloxazolidin-2-on-3-yl)-4(R)-(2-styryl)azetidin-2-on-1-yl]acetic acid N-methyl-N-(3-trifluoromethyl-benzyl)amide. Example 225 was prepared using the procedure of Example 6, except that N-benzyloxycarbonyl-D-aspartic acid β-t-butyl ester monohydrate was replaced with Example 34E, and 3-(trifluoromethyl)benzyl amine was replaced with 4-(piperidinyl)piperidine; Example 223 exhibited an $^1$H NMR spectrum consistent with the assigned structure; Calc'd for $C_{43}H_{48}F_3N_5O_5$: C, 66.91; H, 6.27; N, 9.07. found. C, 66.68; H, 6.25; N, 9.01.

Example 225

Hydrochloride salt. Example 225 (212.5 mg) was dissolved in 30 mL dry $Et_2O$. Dry HCl gas was bubbled through this solution resulting in the rapid formation of an off-white precipitate. HCl addition was discontinued when no more precipitate was observed forming (ca. 5 minutes). The solid was isolated by suction filtration, washed twice with 15 mL of dry $Et_2O$ and dried to 213.5 mg (96% yield) of an off-white solid; Calc'd for $C_{43}H_{49}ClF_3N_5O_5$: C, 63.89; H, 6.11; N, 8.66; Cl, 4.39. found. C, 63.41; H, 5.85; N, 8.60; Cl, 4.86.

Example 225A

2(R)-[[4-[2-(piperidinyl)ethyl]piperidinyl]carbonylmethyl]-2-[3(S)-(4(S)-phenyloxazolidin-2-on-3-yl)-4(R)-(2-styryl)azetidin-2-on-1-yl]acetic acid N—[(S)-α-methylbenzyl]amide. Example 225A was prepared using the procedure of Example 6, except that N-benzyloxycarbonyl-D-aspartic acid β-t-butyl ester monohydrate was replaced with Example 34C, and 3-(trifluoromethyl)benzyl amine was replaced with 4-[2-(piperidinyl)ethyl]piperidine. Example 225A exhibited an $^1$H NMR spectrum consistent with the assigned structure.

Example 225B

2(R)-[[4-[2-(piperidinyl)ethyl]piperidinyl]carbonylmethyl]-2-[3(S)-(4(S)-phenyloxazolidin-2-on-3-yl)-4(R)-(2-styryl)azetidin-2-on-1-yl]acetic acid N—[(R)-α-methylbenzyl]amide. Example 225B was prepared using the procedure of Example 6, except that N-benzyloxycarbonyl-D-aspartic acid β-t-butyl ester monohydrate was replaced with Example 34D, and 3-(trifluoromethyl)benzyl amine was replaced with 4-[2-(piperidinyl)ethyl]piperidine. Example 225B exhibited an ¹H NMR spectrum consistent with the assigned structure.

Example 225C

2(R)-[[4-(Piperidinyl)piperidinyl]carbonylmethyl]-2-[3 (S)-(4(S)-phenyloxazolidin-2-on-3-yl)-4(R)-(2-styryl)azetidin-2-on-1-yl]acetic acid N—[(R)-1-(3-trifluoromethylphenyl)ethyl]amide. Example 225C was prepared using the procedure of Example 6, except that N-benzyloxycarbonyl-D-aspartic acid β-t-butyl ester monohydrate was replaced with Example 34L, and 3-(trifluoromethyl)benzyl amine was replaced with 4-(piperidinyl)piperidine. Example 225C exhibited an ¹H NMR spectrum consistent with the assigned structure.

Example 225D

2(R)-[[4-(Piperidinyl)piperidinyl]carbonylmethyl]-2-[3 (S)-(4(S)-phenyloxazolidin-2-on-3-yl)-4(R)-(2-styryl)azetidin-2-on-1-yl]acetic acid N—[(S)-1-(3-trifluoromethylphenyl)ethyl]amide. Example 225D was prepared using the procedure of Example 6, except that N-benzyloxycarbonyl-D-aspartic acid β-t-butyl ester monohydrate was replaced with Example 34N, and 3-(trifluoromethyl)benzyl amine was replaced with 4-(piperidinyl)piperidine. Example 225D exhibited an ¹H NMR spectrum consistent with the assigned structure.

Examples 87-120E, shown in the following Table, were prepared using the procedure of Example 6, except that N-benzyloxycarbonyl-D-aspartic acid β-t-butyl ester monohydrate was replaced with Example 29, and 3-(trifluoromethyl)benzyl amine was replaced with the appropriate amine; all listed Examples exhibited an ¹H NMR spectrum consistent with the assigned structure.

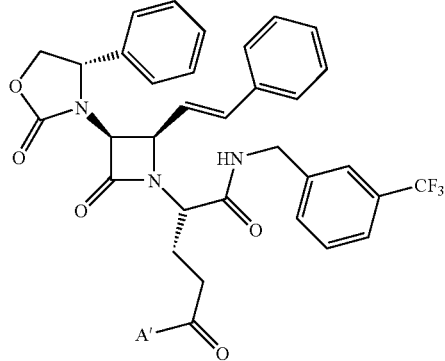

| Example | A' |
|---|---|
| 87 | 2-(piperidinyl)ethylamino |
| 88 | 4-(piperidinyl)piperidinyl |
| 89 | 2-(pyrid-2-yl)ethylamino |
| 90 | morpholin-4-ylamino |
| 91 | 4-(pyrrolidinyl)piperazinyl |
| 92 | 4-(3-trifluorophenyl)piperazinyl |
| 93 | 4-(benzyloxycarbonyl)piperazinyl |
| 94 | 4-[2-(2-hydroxyethoxy)ethyl]piperazinyl |
| 95 | 4-benzylpiperazinyl |
| 96 | 4-(3,4-methylenedioxybenzyl)piperazinyl |
| 97 | 4-phenylpiperazinyl |
| 98 | 4-(3-phenylprop-2-enyl)piperazinyl |
| 99 | 4-ethylpiperazinyl |
| 100 | 2-(dinaethylamino)ethylamino |
| 101 | 4-(pyrrolidinylcarbonylmethyl)piperazinyl |
| 102 | 4-(1-methylpiperidin-4-yl)piperazinyl |
| 103 | 4-butylpiperazinyl |
| 104 | 4-isopropylpiperazinyl |
| 105 | 4-pyridylmethylamino |
| 106 | 3-(dimethylamino)propylamino |
| 107 | 1-benzylpiperidin-4-ylamino |
| 108 | N-benzyl-2-(dimethylamino)ethylamino |
| 109 | 3-pyridylmethylamino |
| 110 | 4-cyclohexylpiperazinyl |
| 111 | 4-(2-cyclohexylethyl)piperazinyl |
| 112 | 4-[2-(morpholin-4-yl)ethyl]piperazinyl |
| 113 | 4-(4-tert-butylbenzyl)piperazinyl |
| 114 | 4-[2-(piperidinyl)ethyl]piperazinyl |
| 115 | 4-[3-(piperidinyl)propyl]piperazinyl |
| 116 | 4-[2-(diisopropylamino)ethyl]piperazinyl |
| 117 | 4-[3-(diethylamino)propyl]piperazinyl |
| 118 | 4-(2-dimethylaminoethyl)piperazinyl |
| 119 | 4-[3-(pyrrolidinyl)propyl]piperazinyl |
| 120 | 4-(cyclohexylmethyl)piperazinyl |
| 120A | 4-[2-(piperidinyl)ethyl]piperidinyl |
| 120B | 4-propyl-piperazinyl |
| 120C | 4-[N-(isopropyl)acetamid-2-yl]piperazinyl |
| 120D | 3-benzyl-hexahydro-(1H)-1,3-diazepinyl |
| 120E | 4-(piperidinylmethyl)piperidinyl |
| 120F | 4-cyclohexylpiperazinyl N-oxide |
| 120G | methoxy |
| 120H | 4-cyclohexylpiperazinyl |

Example 120F

Example 120F was prepared using the procedure of Example 86B, except that Example 63 was replaced with Example 110 to give an off-white solid (54.5 mg, 98%). Example 120F exhibited an ¹H NMR spectrum consistent with the assigned structure.

Example 120G

2(S)-(Methoxycarbonylethyl)-2-[3(S)-(4(S)-phenyloxazolidin-2-on-3-yl)-4(R)-(2-styryl)azetidin-2-on-1-yl]acetic acid N-(3-trifluoromethylbenzyl)amide. Example 120G was prepared using the procedure of Example 6, except that N-benzyloxycarbonyl-D-aspartic acid β-t-butyl ester monohydrate was replaced with Example 34M, and exhibited an ¹H NMR spectrum consistent with the assigned structure.

Example 35

2(S)-[4-(2-phenylethyl)piperazinyl-carbonylethyl]-2-[3 (S)-(4(S)-phenyloxazolidin-2-on-3-yl)-4(R)-(2-styryl)azetidin-2-on-1-yl]acetic acid N-(3-trifluoromethylbenzyl) amide. Using the procedure of Example 6, except that N-benzyloxycarbonyl-D-aspartic acid β-t-butyl ester monohydrate was replaced with the carboxylic acid of Example 29 and 3-(trifluoromethyl)benzyl amine was replaced with 4-(2-phenylethyl)piperazine, the title compound was prepared; $^1$H NMR (CDCl$_3$) δ 2.21-2.23 (m, 1H); 2.25-2.45 (m, 6H); 2.52-2.63 (m, 3H); 2.72-2.82 (m, 2H); 3.42-3.48 (m, 2H); 3.52-3.58 (m, 1H); 4.13-4.18 (m, 1H); 4.26 (dd, J=5.1 Hz, J=8.3 Hz, 1H); 4.29 (d, J=5.0 Hz, 1H); 4.44 (dd, J=6.0 Hz, J=15.0 Hz, 1H); 4.54 (dd, J=6.2 Hz, J=14.9 Hz, 1H); 4.61-4.68 (m, 2H); 4.70-4.75 (m, 1H); 6.27 (dd, J=9.6 Hz, J=15.8 Hz, 1H); 6.73 (d, J=15.8 Hz, 1H); 7.16-7.60 (m, 19H); 8.07-8.12 (m, 1H); FAB$^+$ (M+H)$^+$/z 794; Elemental Analysis calculated for C$_{45}$H$_{46}$F$_3$N$_5$O$_5$: C, 68.08; H, 5.84; N, 8.82. found: C, 67.94; H, 5.90; N, 8.64.

Examples 141-171, shown in the following Table, were prepared using the procedure of Example 6, except that N-benzyloxycarbonyl-D-aspartic acid β-t-butyl ester monohydrate was replaced with Example 34, and 3-(trifluoromethyl)benzyl amine was replaced with the appropriate amine; all listed Examples exhibited an $^1$H NMR spectrum consistent with the assigned structure.

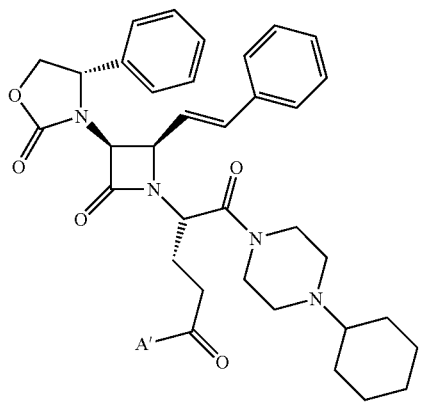

| Example | A' |
| --- | --- |
| 141 | benzylamino |
| 142 | (2-methylbenzyl)amino |
| 143 | (3-methylbenzyl)amino |
| 144 | (4-methylbenzyl)amino |
| 145 | (α-methylbenzyl)amino |
| 146 | N-benzyl-N-methylamino |
| 147 | N-benzyl-N-(t-butyl)amino |
| 148 | N-benzyl-N-butylamino |
| 149 | (3,5-dimethylbenzyl)amino |
| 150 | (2-phenylethyl)amino |
| 151 | dimethylamino |
| 152 | (3-trifluoromethoxybenzyl)amino |
| 153 | (3,4-dichlorobenzyl)amino |
| 154 | (3,5-dichlorobenzyl)amino |
| 155 | (2,5-dichlorobenzyl)amino |
| 156 | (2,3-dichlorobenzyl)amino |
| 157 | (2-fluoro-5-trifluoromethylbenzyl)amino |
| 158 | (4-fluoro-3-trifluoromethylbenzyl)amino |
| 159 | (3-fluoro-5-trifluoromethylbenzyl)amino |
| 160 | (2-fluoro-3-trifluoromethylbenzyl)amino |
| 161 | (4-chloro-3-trifluoromethylbenzyl)amino |
| 162 | indan-1-ylamino |
| 163 | 4-(2-hydroxybenzimidazol-1-yl)-piperidinyl |
| 164 | 3(S)-(tert-butylaminocarbonyl)-1,2,3,4-tetrahydroisoquinolin-2-yl |
| 165 | (3,3-dimethylbutyl)amino |
| 166 | 4-hydroxy-4-phenylpiperidinyl |
| 167 | (cyclohexylmethyl)amino |
| 168 | (2-phenoxyethyl)amino |

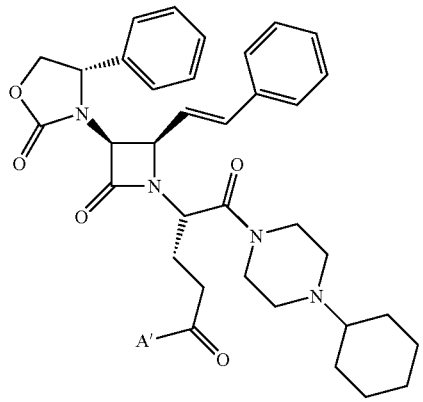

| Example | A' |
| --- | --- |
| 169 | 3,4-methylenedioxybenzylamino |
| 170 | 4-benzylpiperidinyl |
| 171 | (3-trifluoromethylphenyl)amino |

Examples 172-221R, shown in the following Table, were prepared using the procedure of Example 6, except that N-benzyloxycarbonyl-D-aspartic acid β-t-butyl ester monohydrate was replaced with Example 34A, and 3-(trifluoromethyl)benzyl amine was replaced with the appropriate amine; all listed Examples exhibited an $^1$H NMR spectrum consistent with the assigned structure.

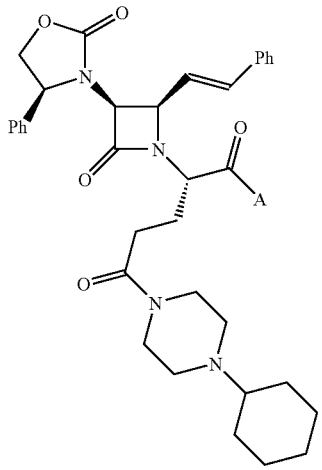

| Example | A |
| --- | --- |
| 172 | (3-trifluoromethoxybenzyl)amino |
| 173 | (3,4-dichlorobenzyl)amino |
| 174 | (3,5-dichlorobenzyl)amino |
| 175 | (2,5-dichlorobenzyl)amino |
| 176 | (2,3-dichlorobenzyl)amino |
| 177 | (2-fluoro-5-trifluoromethylbenzyl)amino |
| 178 | (4-fluoro-3-trifluoromethylbenzyl)amino |
| 179 | (3-fluoro-5-trifluoromethylbenzyl)amino |
| 180 | (2-fluoro-3-trifluoromethylbenzyl)amino |
| 181 | (4-chloro-3-trifluoromethylbenzyl)amino |
| 182 | (2-trifluoromethylbenzyl)amino |
| 183 | (3-methoxybenzyl)amino |
| 184 | (3-fluorobenzyl)amino |
| 185 | (3,5-difluorobenzyl)amino |
| 186 | (3-chloro-4-fluorobenzyl)amino |
| 187 | (3-chlorobenzyl)amino |
| 188 | [3,5-bis(trifluoromethyl)benzyl]amino |

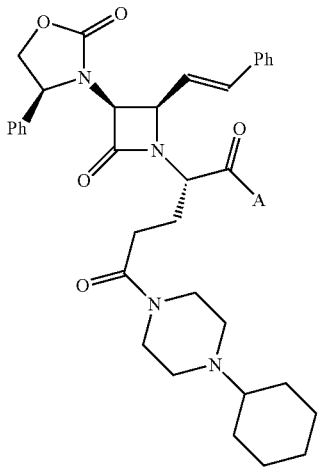

| Example | A |
|---|---|
| 189 | (3-nitrobenzyl)amino |
| 190 | (3-bromobenzyl)amino |
| 191 | benzylamino |
| 192 | (2-methylbenzyl)amino |
| 193 | (3-methylbenzyl)amino |
| 194 | (4-methylbenzyl)amino |
| 195 | (α-methylbenzyl)amino |
| 196 | (N-methylbenzyl)amino |
| 197 | (N-tert-butylbenzyl)amino |
| 198 | (N-butylbenzyl)amino |
| 199 | (3,5-dimethylbenzyl)amino |
| 200 | (2-phenylethyl)amino |
| 201 | (3,5-dimethoxybenzyl)amino |
| 202 | (1R)-(3-methoxyphenyl)ethylamino |
| 203 | (1S)-(3-methoxyphenyl)ethylamino |
| 204 | (α,α-dimethylbenzyl)amino |
| 205 | N-methyl-N-(3-trifluoromethylbenzyl)amino |
| 206 | [(S)-α-methylbenzyl]amino |
| 207 | (1-phenylcycloprop-1yl)amino |
| 208 | (pyridin-2-ylmethyl)amino |
| 209 | (pyridin-3-ylmethyl)amino |
| 210 | (pyridin-4-ylmethyl)amino |
| 211 | (fur-2-ylmethyl)amino |
| 212 | [(5-methylfur-2-yl)methyl]amino |
| 213 | (thien-2-ylmethyl)amino |
| 214 | [(S)-1,2,3,4-tetrahydro-1-naphth-1-yl]amino |
| 215 | [(R)-1,2,3,4-tetrahydro-1-naphth-1-yl]amino |

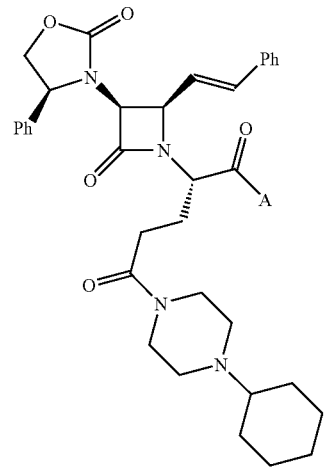

| Example | A |
|---|---|
| 216 | (indan-1-yl)amino |
| 217 | (1-phenylcyclopent-1-yl)amino |
| 218 | (α,α-dimethyl-3,5-dimethoxybenzyl)amino |
| 219 | (2,5-dimethoxybenzyl)amino |
| 220 | (2-methoxybenzyl)amino |
| 221 | (α,α,2-trimethylbenzyl)amino |
| 221A | N-methyl-3-Me-benzylamide |
| 221B | N-methyl-2,3-Cl-benzylamide |
| 221C | N-methyl-3-Cl-benzylamide |
| 221D | N-methyl-3-Br-benzylamide |
| 221E | N-methyl-3,5-Cl-benzylamide |
| 221F | (R)-1-(3-trifluorophenyl)ethylamide |
| 221G | 1-phenyl-cyclohexylamide |
| 221H | 1-(2-fluorophenyl)-cyclopentylamide |
| 221I | 1-(4-fluorophenyl)-cyclopentylamide |
| 221J | 4-CF3-benzylamide |
| 221K | α-phenyl-benzylamide |
| 221L | 3-phenyl-benzylamide |
| 221M | dibenzylamide |
| 221N | 1-naphthalene-methylamide |
| 221O | 1,2,3,4-tetrahydro-isoquinolinamide |
| 221P | indan-2-ylamino |
| 221Q | α-(2-OH-ethyl)benzylamide |
| 221R | (S)-indan-1-ylamino |

The compounds shown in the following Table were prepared according to the processes described herein.

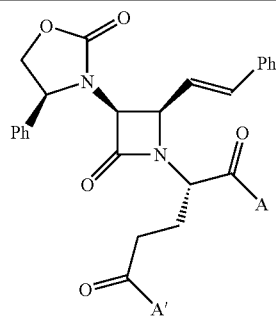

| Example | A | A' |
|---|---|---|
| 221S | (R)-1-indanylamino | 4-cyclohexylpiperazinyl |
| 221T | (αR)-α-(t-butoxycarbonylmethyl)benzylamino | 4-cyclohexylpiperazinyl |
| 221U | (R)-1,2,3,4-tetrahydro-1-naphtylamino | 4-(2-morpholinoethyl)-piperazinyl |
| 221V | (R)-1,2,3,4-tetrahydro-1-naphtylamino | 2-dimethylaminoethylamino |

-continued

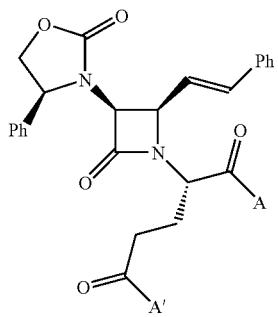

| Example | A | A' |
|---|---|---|
| 221W | (R)-1,2,3,4-tetrahydro-1-naphtylamino | 4-(2-phenylethyl)-homopiperazinyl |
| 221X | (R)-1,2,3,4-tetrahydro-1-naphtylamino | 2-(1-piperidyl)ethylamino |
| 221Y | (R)-1,2,3,4-tetrahydro-1-naphtylamino | (S)-2-(1-pyrrolidinylmethyl)pyrrolidinyl |
| 221Z | (R)-1,2,3,4-tetrahydro-1-naphtylamino | 2-(1-pyrrolidinyl)ethylamino |
| 221AA | (R)-1,2,3,4-tetrahydro-1-naphtylamino | 4-(1-piperidyl)piperidinyl |
| 221AB | 3-CF3-benzylamino | 4-n-butylpiperazinyl |
| 221AC | 3-CF3-benzylamino | 4-ethylpiperazinyl |
| 221AD | (R)-1,2,3,4-tetrahydro-1-naphtylamino | (R)-1-benzylpyrrolidin-3-ylamino |
| 221AE | (R)-1,2,3,4-tetrahydro-1-naphtylamino | quinuclidin-3-ylamino |
| 221AF | (R)-1,2,3,4-tetrahydro-1-naphtylamino | 4-methylhomopiperazinyl |
| 221AG | (R)-1,2,3,4-tetrahydro-1-naphtylamino | 2-pyrroylphenylamino |
| 221AH | (R)-1,2,3,4-tetrahydro-1-naphtylamino | morpholin-4-ylethylamino |
| 221AI | (R)-1,2,3,4-tetrahydro-1-naphtylamino | (S)-1-ethylpyrrolidin-2-ylaminomethyl |
| 221AJ | (R)-1,2,3,4-tetrahydro-1-naphtylamino | (R)-1-ethylpyrrolidin-2-ylaminomethyl |
| 221AK | (R)-1,2,3,4-tetrahydro-1-naphtylamino | (S)-1-butoxycarbonylpyrrolidin-3-ylamino |
| 221AL | (R)-1,2,3,4-tetrahydro-1-naphtylamino | quinolin-3-ylamino |
| 221AM | 1-(3-fluorophenyl)-cyclopentylamino | 4-cyclohexylpiperazinyl |
| 221AN | 1-(4-chlorophenyl)-cyclopropylamino | 4-cyclohexylpiperazinyl |
| 221AO | 1-(4-methoxyphenyl)-cyclopropylamino | 4-cyclohexylpiperazinyl |
| 221AP | 1-(4-methylphenyl)-cyclopropylamino | 4-cyclohexylpiperazinyl |
| 221AQ | 1-(4-chlorophenyl)-cyclopentylamino | 4-cyclohexylpiperazinyl |
| 221AS | 1-(4-methylphenyl)-cyclopentylamino | 4-cyclohexylpiperazinyl |
| 221AT | (R)-1,2,3,4-tetrahydro-1-naphtylamino | 3-(4-chlorophenyl)isoxazolin-5-ylamino |
| 221AU | 1-phenylcyclopentylamino | 4-(1-pyrrolidyl)piperidinyl |
| 221AV | indolinyl | 4-cyclohexylpiperazinyl |
| 221AW | 5-indanylamino | 4-cyclohexylpiperazinyl |
| 221AX | 1-phenylcyclopentylamino | 4-[3-((R)-Boc-amino)-1-pyrrolidyl]piperidinyl |
| 221AY | 4-indanylamino | 4-cyclohexylpiperazinyl |
| 221AZ | 1-phenylcyclopentylamino | (3R)-4-(3-chloroammoniumpyrrolidinyl)piperdinyl |
| 221BA | (R)-1,2,3,4-tetrahydro-1-naphtylamino | 4-(2-fluorophenyl)piperazinyl |
| 221BB | (R)-1,2,3,4-tetrahydro-1-naphtylamino | 4-(3-chlorophenyl)piperazinyl |
| 221BC | (R)-1,2,3,4-tetrahydro-1-naphtylamino | 4-(4-fluorophenyl)piperazinyl |
| 221BD | (R)-1,2,3,4-tetrahydro-1-naphtylamino | 4-ethylpiperazinyl |

-continued

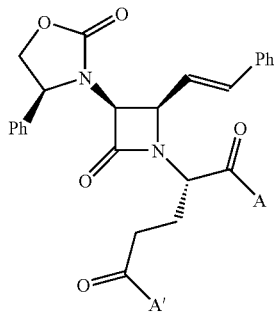

| Example | A | A' |
|---|---|---|
| 221BE | (R)-1,2,3,4-tetrahydro-1-naphtylamino | 4-phenylpiperazinyl |
| 221BF | (R)-1,2,3,4-tetrahydro-1-naphtylamino | 4-benzylpiperazinyl |
| 221BG | (R)-1,2,3,4-tetrahydro-1-naphtylamino | 4-methylpiperazinyl |
| 221BH | (R)-1,2,3,4-tetrahydro-1-naphtylamino | 4-(2-methoxyphenyl)piperazinyl |
| 221BI | (R)-1,2,3,4-tetrahydro-1-naphtylamino | 4-(3-OH-n-propyl)piperazinyl |
| 221BJ | (R)-1,2,3,4-tetrahydro-1-naphtylamino | 4-(4-hydroxyphenyl)piperazinyl |

Examples 135-140, shown in the following Table, were prepared using the procedure of Example 6, except that N-benzyloxycarbonyl-D-aspartic acid β-t-butyl ester monohydrate was replaced with Example 33, and 3-(trifluoromethyl)benzyl amine was replaced with the appropriate amine; all listed Examples exhibited an $^1$H NMR spectrum consistent with the assigned structure.

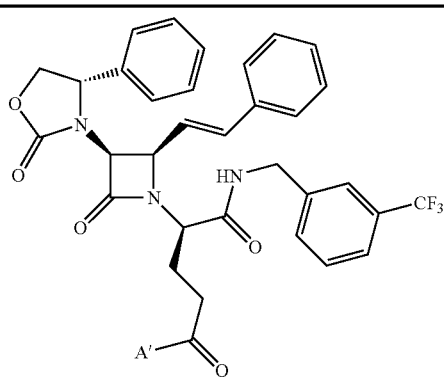

| Example | A' |
|---|---|
| 135 | 4-(piperidinyl)piperidinyl |
| 136 | 4-(2-phenylethyl)piperazinyl |
| 137 | 4-butylpiperazinyl |
| 138 | 4-isopropylpiperazinyl |
| 139 | 4-cyclohexylpiperazinyl |
| 140 | 4-(cyclohexylmethyl)piperazinyl |

Example 140A

2(R)-(2-(3-trifluoromethylbenzyl)amino-1-ylcarbonyl)ethyl)-2-[3(S)-(4(S)-phenyloxazolidin-2-on-3-yl)-4(R)-(2-styryl)azetidin-2-on-1-yl]acetic acid N-(4-cyclohexyl)piperazinamide. Example 140A was prepared using the procedure of Example 6, except that N-benzyloxycarbonyl-D-aspartic acid β-t-butyl ester monohydrate was replaced with Example 34Q, and 3-(trifluoromethyl)benzylamine was replaced with 1-cyclohexylpiperazine, and exhibited an $^1$H NMR spectrum consistent with the assigned structure.

Examples 226-230C, shown in the following Table, were prepared using the procedure of Example 6, except that N-benzyloxycarbonyl-D-aspartic acid β-t-butyl ester monohydrate was replaced with Example 34F, and 3-(trifluoromethyl)benzyl amine was replaced with the appropriate amine; all listed Examples exhibited an $^1$H NMR spectrum consistent with the assigned structure.

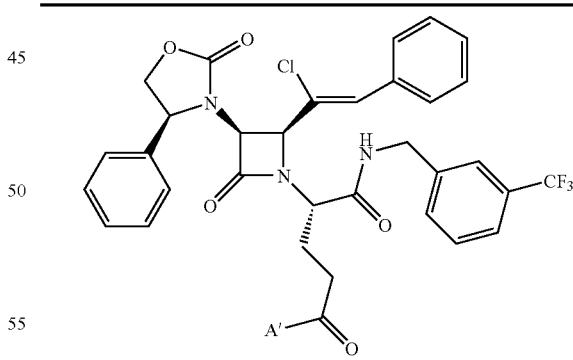

| Example | A' |
|---|---|
| 226 | 4-cyclohexylpiperazinyl |
| 227 | 4-(pyrrolidinyl)piperazinyl |
| 227A | 4-[2-(2-hydroxyethyloxy)ethyl]piperazinyl |
| 227B | 4-benzylpiperazinyl |
| 227C | 4-(3,4-methylendioxybenzyl)piperazinyl |
| 228 | 4-ethylpiperazinyl |
| 229 | 4-n-butylpiperazinyl |
| 230 | 4-isopropylpiperazinyl |
| 230A | 1-benzylpiperidin-4-ylamino |

-continued

| | |
|---|---|
| 230B | 4-(2-cyclohexylethyl)piperazinyl |
| 230C | 4-[2-(morpholin-4-yl)ethyl]piperazinyl |

The following compounds were prepared according to the processes described herein:

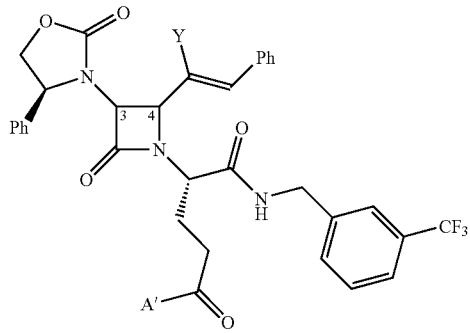

| Example | Y | C(3)-C(4) Stereochemistry | A' |
|---|---|---|---|
| 230D | F | not determined | 4-n-butylpiperazinyl |
| 230E | F | not determined | (R)-1-benzylpyrrolidin-3-amino |
| 230F | F | not determined | quinuclidin-3-ylamino |
| 230G | F | (3S,4R) | (S)-1-benzylpyrrolidin-3-amino |
| 230H | Cl | not determined | (R)-1-benzylpyrrolidin-3-amino |
| 230I | Cl | (3S,4R) | (R)-1-benzylpyrrolidin-3-amino |
| 230J | Cl | (3S,4R) | (S)-1-benzylpyrrolidin-3-amino |
| 230K | Cl | not determined | (S)-1-benzylpyrrolidin-3-amino |
| 230L | Br | not determined | 4-n-butylpiperazinyl |
| 230M | Br | not determined | 4-ethylpiperazinyl |

Example 86C

2(S)-[[4-(Piperidinyl)piperidinyl]carbonymethyl]-2-[3 (S)-(4(R)-phenyloxazolidin-2-on-3-yl)-4(R)-(2-styryl)azetidin-2-on-1-yl]acetic acid N-(3-trifluoromethylbenzyl) amide. Example 86C was prepared using the procedure of Example 6, except that N-benzyloxycarbonyl-D-aspartic acid β-t-butyl ester monohydrate was replaced with Example 28A, and 3-(trifluoromethyl)benzyl amine was replaced with 4-(piperidinyl)piperidine, and exhibited an $^1$H NMR spectrum consistent with the assigned structure.

Example 231

2(R)-[[4-(Piperidinyl)piperidinyl]carbonylmethyl]-2-[3 (S)-(4(S)-phenyloxazolidin-2-on-3-yl)-4(R)-(2'-methoxystyr-2-yl)azetidin-2-on-1-yl]acetic acid N-(3-trifluoromethylbenzyl)amide. Example 231 was prepared using the procedure of Example 6, except that N-benzyloxycarbonyl-D-aspartic acid β-t-butyl ester monohydrate was replaced with Example 34G, and 3-(trifluoromethyl)benzyl amine was replaced with 4-(piperidinyl)piperidine, and exhibited an $^1$H NMR spectrum consistent with the assigned structure.

Examples 232-233A, shown in the following Table, were prepared using the procedure of Example 6, except that N-benzyloxycarbonyl-D-aspartic acid β-t-butyl ester monohydrate was replaced with Example 34H, and 3-(trifluoromethyl)benzyl amine was replaced with the appropriate amine; all listed Examples exhibited an $^1$H NMR spectrum consistent with the assigned structure.

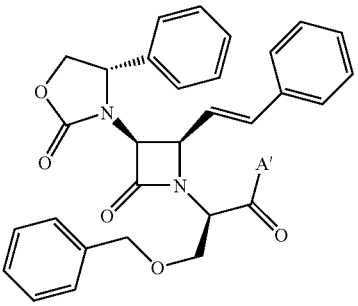

| Example | A' | α |
|---|---|---|
| 232 | 4-(piperidinyl)piperidinyl | D |
| 232A | (3-trifluorobenzyl)amino | D |
| 232B | 4-(3-trifluoromethylphenyl)piperazinyl | D or L |
| 232C | 4-(3-trifluoromethylphenyl)piperazinyl | D or L |
| 232D | 4-cyclohexylpiperazinyl | DL |
| 232E | 4-(piperidinylmethyl)piperidinyl | D |
| 233 | 4-[2-(piperidinyl)ethyl]piperidinyl | D |
| 233A | 4-[(1-piperidyl)methyl]piperidinamide | D |

Example 234

(2RS)-[4-(piperidinyl)piperidinylcarbonyl]-2-methyl-2-[3(S)-(4(S)-phenyloxazolidin-2-on-3-yl)-4(R)-(2-styryl) azetidin-2-on-1-yl]acetic acid N-(3-trifluoromethylbenzyl) amide.

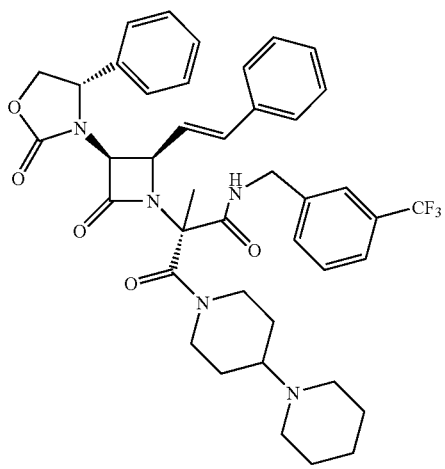 [SMILES: C[C@](C(=O)NCc1cccc(C(F)(F)F)c1)(C(=O)N1CCC(N2CCCCC2)CC1)N1C(=O)[C@@H](N2C(=O)OC[C@@H]2c2ccccc2)[C@H]1/C=C/c1ccccc1]

Example 37 (50 mg, 0.067 mmol) in tetrahydrofuran (4 mL) was treated sequentially with sodium hydride (4 mg, 0.168 mmol) and methyl iodide (6 μL, 0.094 mmol) at −78° C. The resulting mixture was slowly warmed to ambient temperature, and evaporated. The resulting residue was partitioned between dichloromethane and water, and the organic layer was evaporated. The resulting residue was purified by silica gel chromatography (95:5 chloroform/methanol) to give 28 mg (55%) of the title compound as an off-white solid; MS (ES$^+$): m/z=757 (M$^+$).

Example 234A 4-(Piperidinyl)-piperidinyl 3(R)-[3(S)-(4(S)-phenyloxazolidin-2-on-3-yl)-3-methyl-4(R)-(styr-2-yl)azetidin-2-on-1-yl]-3-[(3-trifluoromethyl)phenylmethylaminocarbonyl]propanoic acid

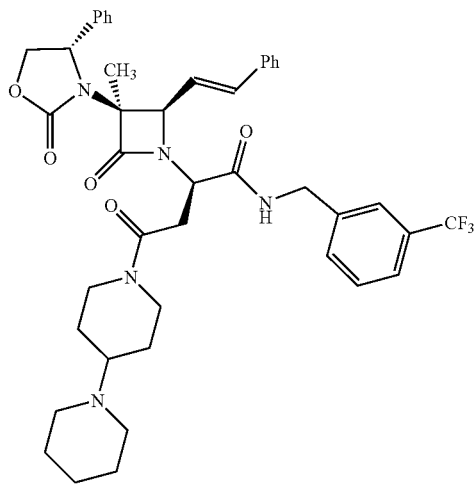 [SMILES: C[C@@]1(N2C(=O)OC[C@@H]2c2ccccc2)C(=O)N([C@H](CC(=O)N2CCC(N3CCCCC3)CC2)C(=O)NCc2cccc(C(F)(F)F)c2)[C@@H]1/C=C/c1ccccc1]

Using the procedure of Example 6, except that N-benzyloxycarbonyl-D-aspartic acid β-t-butyl ester monohydrate was replaced with the carboxylic acid of Example 34J and 3-(trifluoromethyl)benzyl amine was replaced with 4-(piperidinyl)piperidine, the title compound was prepared in quantitative yield; MS (m+H)$^+$ 772.

The compounds shown in the following Table were prepared according to the processes described herein.

| C(3)-C(4) Stereochemistry | R | A' |
|---|---|---|
| (3S,4R) | H | 4-(piperidyl)piperidinyl |
| (3S,4R) | Me | 4-(piperidyl)piperidinyl |
| not determined | H | 4-(piperidyl)piperidinyl |

Example 235

2(S)-[[(1-Benzylpiperidin-4-yl)amino]carbonylmethyl]-2-[3(S)-(4(S)-phenyloxazolidin-2-on-3-yl)-4(R)-(2-phenyleth-1-yl)azetidin-2-on-1-yl]acetic acid N-(3-trifluoromethylbenzyl)amide. Example 235 was prepared using the procedure of Example 8, except that N-benzyloxycarbonyl-L-aspartic acid β-t-butyl ester α-(3-trifluoromethyl)benzylamide was replaced with Example 63 (50 mg, 0.064 mmol) to give 40 mg (80%) of Example 235 as an off-white solid; Example 235 exhibited an $^1$H NMR spectrum consistent with the assigned structure.

Example 236

(2S)-[(4-cyclohexylpiperazinyl)carbonylethyl]-2-[3(S)-(4(S)-phenyloxazolidin-2-on-3-yl)-4(R)-(2-phenyleth-1-yl)azetidin-2-on-1-yl]acetic acid N-(3-trifluoromethylbenzyl)amide. Example 236 was prepared using the procedure of Example 8, except that N-benzyloxycarbonyl-L-aspartic acid β-t-butyl ester α-(3-trifluoromethyl)benzylamide was replaced with Example 110 (50 mg, 0.065 mmol) to give 42 mg (84%) of Example 236 as an off-white solid; Example 236 exhibited an $^1$H NMR spectrum consistent with the assigned structure.

Example 236A (2S)-[(4-cyclohexylpiperazinyl)carbonylethyl]-2-[3(S)-(4(S)-phenyloxazolidin-2-on-3-yl)-4(R)-(2-phenyleth-1-yl)azetidin-2-on-1-yl]acetic acid N—[(R)-1,2,3,4-tetrahydronaphth-1-yl]amide. Example 236A was prepared using the procedure of Example 8, except that N-benzyloxycarbonyl-L-aspartic acid β-t-butyl ester α-(3-trifluoromethyl)benzylamide was replaced with Example 215 (76 mg, 0.10 mmol) to give 69 mg (90%) of Example 236A as an off white solid. Example 236A exhibited an $^1$H NMR spectrum consistent with the assigned structure.

Example 237

2(R)-[[4-(Piperidinyl)piperidinyl]carbonylmethyl]-2-[3(S)-(4(S)-phenyloxazolidin-2-on-3-yl)-4(R)-(propen-1-yl)azetidin-2-on-1-yl]acetic acid N-(3-trifluoromethylbenzyl)amide. Example 237 was prepared using the procedure of Example 6, except that N-benzyloxycarbonyl-D-aspartic acid β-t-butyl ester monohydrate was replaced with Example 34K, and 3-(trifluoromethyl)benzyl amine was replaced with 4-(piperidinyl)piperidine. Example 237 exhibited an $^1$H NMR spectrum consistent with the assigned structure.

Example 238

(2S)-(Benzylthiomethyl)-2-[3(S)-(4(S)-phenyloxazolidin-2-on-3-yl)-4(R)-(2-styryl)azetidin-2-on-1-yl]acetic acid N-[4-[2-(piperid-1-yl)ethyl]piperidin-1-yl]amide. This Example was prepared using the procedure of Example 6, except that N-benzyloxycarbonyl-D-aspartic acid β-t-butyl ester monohydrate was replaced with the corresponding benzyl protected cysteine analog, and 3-(trifluoromethyl)benzyl amine was replaced with 4-[2-(piperid-1-yl)ethyl]piperidine.

Step 1. N-tButyloxycarbonyl-(S)-(benzyl)-D-cysteine-[4-(2-(1-piperidyl)ethyl)]piperidinenamide. N-tButyloxycarbonyl-(S)-Benzyl-N-(tbutyloxycarbonyl)-D-cysteine (0.289 g, 0.93 mmole) and 4-[2-(1-piperidyl)ethyl]piperidine (0.192 g, 0.98 mmole) in dichloromethane (20 mL) gave 0.454 g (quantitative yield) of Example X as an off-white solid. $^1$H NMR (CDCl$_3$) δ 0.89-1.15 (m, 2H); 1.39-1.44 (m, 16H); 1.54-1.61 (m, 4H); 1.62-1.71 (m, 1H); 2.21-2.35 (m, 5H); 2.49-2.58 (m, 2H); 2.66-2.74 (m, 1H); 2.79-2.97 (m, 1H); 3.67-3.76 (m, 3M); 4.48-4.51 (m, 1H); 4.72-4.75 (m, 1H); 5.41-5.44 (m, 1H); 7.19-7.34 (m, 5H).

Step 2. (S)-(benzyl)-D-cysteine-[4-(2-(1-piperidyl)ethyl)]piperidinenamide, dihydrochloride. N-tButyloxycarbonyl- (S)-(benzyl)-D-cysteine-[4-(2-(1-piperidyl)ethyl)]piperidinenamide (0.453 g, 0.93 mmole) was reacted overnight with acetyl chloride (0.78 mL, 13.80 mmole) in anhydrous methanol (15 mL). The title compound was obtained as an off-white solid by evaporating the reaction mixture to dryness (0.417 g, 97%). $^1$H NMR (CD$_3$OD) δ 0.94-1.29 (m, 2H); 1.49-1.57 (m, 1H); 1.62-1.95 (m, 10H); 2.65-2.80 (m, 2H); 2.81-2.97 (m, 4H); 3.01-3.14 (m, 2H); 3.50-3.60 (m, 3H); 3.81-3.92 (m, 2H); 4.41-4.47 (m, 2H); 7.25-7.44 (m, 5H).

Step 3. Using the general procedures described herein, the imine prepared from (S)-(benzyl)-D-cysteine-[4-(2-(1-piperidyl)ethyl)]piperidinenamide, dihydrochloride (0.417 g, 0.90 mmole) and cinnamaldehyde, in the presence on triethylamine (0.26 mL, 1.87 mmole), was combined with 2-(4(S)-phenyloxazolidin-2-on-3-yl)acetyl chloride (Example 1) to give 0.484 g (76%) of Example 238 as an off-white solid after recrystallization from dichloromethane/hexanes. $^1$H NMR (CDCl$_3$) δ 0.89-1.06 (m, 2H); 1.40-1.44 (m, 5H); 1.57-1.67 (m, 6H); 2.25-2.43 (m, 6H); 2.45-2.59 (m, 2H); 2.71-2.88 (m, 2H); 3.55-3.70 (m, 3H); 4.11-4.17 (m, 1H); 4.37-4.47 (m, 2H); 4.54-4.61 (m, 1H); 4.64-4.69 (m, 11H); 4.76-4.84 (m, 2H); 6.05-6.19 (m, 1H); 6.66-6.71 (m, 1H); 7.12-7.40 (m, 15H).

Table 16 illustrates selected compounds further characterized by mass spectral analysis using FAB$^+$ to observe the corresponding (M+H)$^+$ parent ion.

TABLE 16

| Example | (m + H)$^+$/z |
|---|---|
| 37 | 744 |
| 38 | 766 |
| 39 | 766 |
| 40 | 718 |
| 41 | 704 |
| 42 | 744 |
| 42A | 772 |
| 44 | 758 |
| 63 | 780 |
| 85 | 766 |
| 86A | 786 |
| 86C | 758 |
| 88 | 772 |
| 91 | 759 |
| 95 | 780 |
| 96 | 824 |
| 104 | 732 |
| 110 | 772 |
| 111 | 800 |
| 112 | 803 |
| 120 | 786 |
| 120A | 800 |
| 120B | 732 |
| 120E | 788 |
| 132B | 758 |
| 133 | 758 |
| 134A | 786 |
| 134C | 780 |
| 134H | 772 |
| 136 | 794 |
| 137 | 746 |
| 138 | 732 |
| 139 | 772 |
| 174 | 772 |
| 175 | 772 |
| 176 | 772 |
| 177 | 790 |
| 179 | 790 |
| 180 | 790 |
| 182 | 772 |
| 183 | 734 |
| 184 | 722 |
| 185 | 740 |

TABLE 16-continued

| Example | (m + H)$^+$/z |
|---|---|
| 186 | 756 |
| 187 | 738 |
| 188 | 840 |
| 189 | 749 |
| 190 | 782 |
| 191 | 704 |
| 192 | 718 |
| 193 | 718 |
| 199 | 732 |
| 200 | 718 |
| 201 | 764 |
| 202 | 748 |
| 203 | 748 |
| 205 | 786 |
| 206 | 718 |
| 207 | 730 |
| 208 | 705 |
| 209 | 705 |
| 210 | 705 |
| 211 | 694 |
| 212 | 708 |
| 213 | 710 |
| 214 | 744 |
| 215 | 744 |
| 216 | 7530 |
| 217 | 758 |
| 218 | 792 |
| 219 | 764 |
| 220 | 734 |
| 221 | 746 |
| 222 | 776 |
| 224 | 704 |
| 225 | 772 |
| 226 | 806 |
| 227 | 792 |
| 228 | 752 |
| 229 | 780 |
| 230 | 766 |
| 231 | 788 |
| 232 | 663 |
| 233 | 691 |
| 234 | 758 |
| 235 | 782 |
| 236 | 774 |

METHOD EXAMPLES

Method Example 1

Human vasopression $V_{1a}$ receptor binding assay. A cell line expressing the human $V_{1a}$ receptor in CHO cells (henceforth referred to as the h$V_{1a}$ cell line) was obtained from Dr. Michael Brownstein, NIMH, Bethesda, Md., USA. The h$V_{1a}$ cDNA sequence is described by Thibonnier et al., *Journal of Biological Chemistry,* 269, 3304-3310 (1994), and the expression method was the same as described by Morel et al. (1992). The h$V_{1a}$ cell line was grown in alpha-MEM with 10% fetal bovine serum and 250 ug/ml G418 (Gibco, Grand Island, N.Y., USA). For competitive binding assay, hV1a cells were plated into 6-well culture plate at 1:10 dilution from a confluency flask, and maintained in culture for at least two days. Culture medium was then removed, cells were washed with 2 ml binding buffer (25 mM Hepes, 0.25% BSA, 1×DMEM, PH=7.0). To each well, 990 μl binding buffer containing 1 nM 3H-AVP was added, and followed by 10 μl series diluted Example compounds dissolved in DMSO. All incubations were in triplicate, and dose-inhibition curves consisted of total binding (DMSO) and 5 concentrations (0.1, 1.0, 10, 100, and 1000 nM) of test agents encompassing the IC$_{50}$. 100 nM cold AVP (Sigma) was used to assess non-specific binding. Cells were incubated for 45 minutes at 37° C., assay mixture was removed and each well was washed three times with PBS (pH=7.4). 1 ml 2% SDS was added per well and plates were let sit for 30 minutes. The whole content in a well was transferred to a scintillation vial. Each well was rinsed with 0.5 ml PBS which was then added to the corresponding vial. Scintillation fluid (Ecoscint, National Diagnostics, Atlanta, Ga.) was then added at 3 ml per vial. Samples were counted in a liquid scintillation counter (Beckman LS3801). $IC_{50}$ values were calculated by Prism Curve fitting software.

All of the alkanedioic esters and amides exemplified in the foregoing examples dissolved in DMSO were tested in this assay. Binding curves were generated according to methods described by Thibonnier et al. (1994). [$^3$H]-AVP was added to the hV1a cell cultures followed by 10 fold dilutions of each test compound. All active compounds showed a dose-dependent competitive binding curve, with $IC_{50}$ and $K_i$ values characteristic of high affinity binding to $V_{1a}$ receptors in CHO cells expressing the human $V_{1a}$ receptor (the hV1a cell line). Example 225 showed a dose-dependent competitive binding curve, with $IC_{50}$ (1.86-2.13 nM) and $K_i$ (1.14-1.30 nM) values. Binding affinities for illustrative compounds are summarized in the Table 17.

TABLE 17

| Example | $V_{1a}$ Binding Affinity ($IC_{50}$ (nM)) |
|---|---|
| 18 | 35 |
| 19 | 35 |
| 20 | 35 |
| 35 | 1.9 |
| 37 | 5.5 |
| 38 | <25 |
| 39 | 23 |
| 40 | 11 |
| 41 | <20 |
| 42 | <20 |
| 42A | 1.77 |
| 44 | 3.1 |
| 47 | ~50 |
| 59 | <100 |
| 63 | 1.84 |
| 66 | ~50 |
| 77 | <100 |
| 78 | <100 |
| 81 | <100 |
| 82 | <50 |
| 85 | 5.87 |
| 86A | 9.79 |
| 87 | 15 |
| 88 | 2.4 |
| 91 | 3.24 |
| 95 | 1.76 |
| 96 | 4.35 |
| 100 | <100 |
| 101 | ~100 |
| 102 | <100 |
| 103 | 0.81 |
| 104 | 1.85 |
| 106 | ~100 |
| 107 | <50 |
| 108 | ~100 |
| 109 | ~100 |
| 110 | 0.49 |
| 111 | 1.31 |
| 112 | 1.34 |
| 120 | 0.75 |
| 120A | 16.2 |
| 120B | 2.93 |
| 120E | 3.2 |
| 120H | 2.75 |
| 132D | 6.3 |
| 132F | 4.8 |

TABLE 17-continued

| Example | $V_{1a}$ Binding Affinity ($IC_{50}$ (nM)) |
|---|---|
| 133 | 2.43 |
| 134A | 12.9 |
| 134B | 44.8 |
| 134C | 9.1 |
| 134G | 6 |
| 134J | 5.29 |
| 135 | ~50 |
| 136 | 11 |
| 137 | 17 |
| 138 | 21 |
| 139 | 9.5 |
| 172 | 4.5 |
| 173 | <100 |
| 174 | 1.46 |
| 175 | 4.56 |
| 176 | 0.61 |
| 177 | 0.67 |
| 178 | <50 |
| 179 | 0.81 |
| 180 | 0.33 |
| 181 | <50 |
| 182 | 1.52 |
| 183 | <10 |
| 184 | <10 |
| 185 | 1.27 |
| 186 | <10 |
| 187 | 1 |
| 188 | 7.26 |
| 189 | 1.7 |
| 190 | 0.88 |
| 191 | 2.92 |
| 192 | <10 |
| 193 | 1.17 |
| 194 | <100 |
| 195 | <50 |
| 196 | <100 |
| 198 | ~100 |
| 199 | <10 |
| 200 | 5.08 |
| 201 | 10.5 |
| 203 | 2.46 |
| 204 | 6 |
| 205 | 0.34 |
| 206 | 1.58 |
| 207 | 4.48 |
| 208 | 16.3 |
| 209 | 16 |
| 210 | 29.5 |
| 211 | 5.37 |
| 212 | 0.95 |
| 213 | 0.78 |
| 214 | 1.86 |
| 215 | 0.61 |
| 216 | 1.83 |
| 217 | 3.17 |
| 218 | 7.7 |
| 219 | 0.63 |
| 220 | 5.3 |
| 221 | 5.1 |
| 221A | 2.71 |
| 221B | 0.59 |
| 221C | 3 |
| 221D | 2.41 |
| 221E | 20.2 |
| 221F | 1.7 |
| 221G | 1.5 |
| 221H | 4 |
| 221I | 12 |
| 221K | ~5 |
| 221O | 8.4 |
| 221P | 1.7 |
| 221Q | 18.1 |
| 221R | 5.13 |
| 221S | 5.03 |
| 221X | 11.6 |
| 221Y | 7.6 |

TABLE 17-continued

| Example | V$_{1a}$ Binding Affinity (IC$_{50}$ (nM)) |
|---|---|
| 221AB | <10 |
| 221AC | <10 |
| 221AD | ~50 |
| 221AE | ~50 |
| 221AI | ~50 |
| 221AL | ~100 |
| 221AO | ~100 |
| 221AQ | ~50 |
| 221AS | ~20 |
| 221AX | 83 |
| 221AY | ~30 |
| 221BD | 2.7 |
| 221BI | 56 |
| 222 | 1.83 |
| 224 | 0.49 |
| 225 | 1.08 |
| 226 | 0.49 |
| 227 | 11 |
| 228 | 13.6 |
| 229 | 1.53 |
| 230 | 7.07 |
| 230F | ~100 |
| 230L | 12.7 |
| 231 | 6.12 |
| 232 | 1.37 |
| 232D | 2.04 |
| 232E | 0.28 |
| 233 | 0.56 |
| 234 | 2.37 |
| 234A | 8.6 |
| 235 | 37 |
| 236 | 1.68 |
| 236A | 9 |
| 238 | 0.11 |

TABLE 18

| Example | V$_{1a}$ K$_i$ (nM) |
|---|---|
| 35 | 1.17 |
| 37 | 3.39 |
| 38 | 85 |
| 39 | 13.3 |
| 40 | 6.5 |
| 41 | 18.2 |
| 42 | 26.4 |
| 42A | 1.17 |
| 44 | 1.89 |
| 63 | 1.13 |
| 82 | 5.12 |
| 85 | 3.6 |
| 86A | 6 |
| 88 | 1.45 |
| 91 | 1.99 |
| 95 | 1.08 |
| 96 | 2.66 |
| 103 | 0.49 |
| 104 | 1.13 |
| 110 | 0.27 |
| 111 | 0.82 |
| 112 | 0.8 |
| 120 | 0.46 |
| 120A | 9.9 |
| 120B | 1.79 |
| 120E | 1.95 |
| 120H | 1.68 |
| 132D | 3.9 |
| 132F | 3 |
| 133 | 1.49 |
| 134A | 7.9 |
| 134B | 27.5 |
| 134C | 5.58 |

TABLE 18-continued

| Example | V$_{1a}$ K$_i$ (nM) |
|---|---|
| 134G | 3.7 |
| 134J | 3.25 |
| 136 | 33 |
| 137 | 10.5 |
| 138 | 13 |
| 139 | 5.84 |
| 172 | 2.78 |
| 174 | 0.89 |
| 175 | 2.79 |
| 176 | 0.38 |
| 177 | 0.41 |
| 179 | 0.51 |
| 180 | 0.2 |
| 182 | 0.93 |
| 185 | 0.82 |
| 187 | 0.66 |
| 188 | 4.45 |
| 189 | 1.04 |
| 190 | 0.54 |
| 191 | 1.79 |
| 193 | 0.72 |
| 200 | 3.11 |
| 201 | 6.43 |
| 203 | 1.5 |
| 204 | 3.7 |
| 205 | 0.21 |
| 206 | 0.97 |
| 207 | 2.74 |
| 208 | 10 |
| 209 | 9.8 |
| 210 | 18.1 |
| 211 | 3.29 |
| 212 | 0.58 |
| 213 | 0.48 |
| 214 | 1.14 |
| 215 | 0.38 |
| 216 | 1.12 |
| 217 | 1.94 |
| 218 | 4.7 |
| 219 | 0.39 |
| 220 | 3.26 |
| 221 | 3.1 |
| 221A | 1.66 |
| 221B | 0.36 |
| 221C | 1.84 |
| 221D | 1.48 |
| 221E | 12.4 |
| 221F | 1.04 |
| 221G | 0.93 |
| 221H | 2.5 |
| 221I | 7.4 |
| 221O | 5.1 |
| 221P | 1.1 |
| 221Q | 11.1 |
| 221R | 3.14 |
| 221S | 3.08 |
| 221X | 7.2 |
| 221Y | 4.7 |
| 221AM | 2.7 |
| 221AP | 3.8 |
| 221AX | 51 |
| 221BD | 1.66 |
| 221BI | 35 |
| 222 | 1.13 |
| 224 | 0.3 |
| 225 | 0.66 |
| 225-HCl | 1.36 |
| 226 | 0.3 |
| 227 | 6.71 |
| 228 | 8.35 |
| 229 | 0.94 |
| 230 | 4.33 |
| 230L | 7.8 |
| 231 | 3.75 |
| 232 | 0.84 |
| 232D | 1.25 |
| 232E | 0.17 |

TABLE 18-continued

| Example | $V_{1a} K_i$ (nM) |
|---|---|
| 233 | 0.34 |
| 233A | 11.6 |
| 234 | 1.45 |
| 234A | 5.25 |
| 235 | 23 |
| 236 | 1.03 |
| 236A | 5.5 |
| 238 | 0.07 |

Method Example 2

Inhibition of phosphatidylinositol turnover. The physiological effects of vasopressin are mediated through specific G-protein coupled receptors. The vasopressin $V_{1a}$ receptor is coupled to the $G_q/G_{11}$ family of G proteins and mediates phosphatidylinositol turnover. The agonist or antagonist character of the compounds of the invention may be determined by their ability to inhibit vasopressin-mediated turnover of phosphatidylinositol by the procedure described in the following paragraphs. Representative compounds of the invention, the compounds of Examples 35, 44, 88, 110, and 133, were tested in this assay and found to be vasopressin $V_{1a}$ antagonists.

Cell culture and labeling of cells. Three days prior to the assay, near-confluent cultures of hV1a cells were dissociated and seeded in 6-well tissue culture plates, about 100 wells being seeded from each 75 cm² flask (equivalent to 12:1 split ratio). Each well contained 1 mL of growth medium with 2 µCi of [³H]myo-inositol (American Radiolabeled Chemicals, St. Louis, Mo., USA).

Incubations. All assays were in triplicate except for basal and 10 nM AVP (both n=6). AVP ((arginine vasopressin), Peninsula Labs, Belmont, Calif., USA (#8103)) was dissolved in 0.1N acetic acid. Test agents were dissolved in DMSO and diluted in DMSO to 200 times the final test concentration. Test agents and AVP (or corresponding volumes of DMSO) were added separately as 5 mL in DMSO to 12×75 mm glass tubes containing 1 mL of assay buffer (Tyrode's balanced salt solution containing 50 mM glucose, 10 mM LiCl, 15 mM HEPES pH 7.4, 10 µM phosphoramidon, and 100 µM bacitracin). The order of incubations was randomized. Incubations were initiated by removing the prelabeling medium, washing the monolayer once with 1 mL of 0.9% NaCl, and transferring the contents of the assay tubes to corresponding wells. The plates were incubated for 1 hour at 37° C. Incubations were terminated by removing the incubation medium and adding 500 µL of ice cold 5% (w/v) trichloroacetic acid and allowing the wells to stand for 15 min.

Measurement of [³H]inositol phosphates. BioRad Poly-Prep Econo-Columns were packed with 0.3 mL of AG 1 X-8 100-200 formate form resin. Resin was mixed 1:1 with water and 0.6 mL added to each column. Columns were then washed with 10 mL water. Scintillation vials (20 mL) were placed under each column. For each well, the contents were transferred to a minicolumn, after which the well was washed with 0.5 mL distilled water, which was also added to the minicolumn. The columns were then washed twice with 5 mL of 5 mM myo-inositol to elute free inositol. Aliquots (1 mL) were transferred to 20 mL scintillation vials and 10 mL of Beckman Ready Protein Plus added. After the myo-inositol wash was complete, empty scintillation vials were placed under the columns, and [³H]inositol phosphates were eluted with three additions of 1 mL 0.5 M ammonium formate containing 0.1 N formic acid. Elution conditions were optimized to recover inositol mono-, bis-, and trisphosphates, without eluting the more metabolically inert tetrakis-, pentakis-, and hexakis-phosphates. To each sample was added 10 mL of a high salt capacity scintillation fluid such as Tru-Count High Salt Capacity or Packard Hionic-Fluor. Inositol lipids were measured by adding 1 mL of 2% sodium dodecyl sulfate (SDS) to each well, allowing the wells to stand for at least 30 min., and transferring the solution to 20 mL scintillation vials, to which 10 mL Beckman Ready Protein Plus scintillation fluid was then added. Samples were counted in a Beckman LS 3801 liquid scintillation counter for 10 min. Total inositol incorporation for each well was calculated as the sum of free inositol, inositol phosphates, and inositol lipids.

Data analysis: concentration-inhibition experiments. Concentration-response curves for AVP and concentration-inhibition curves for test agents versus 10 nM AVP were analyzed by nonlinear least-squares curve-fitting to a 4-parameter logistic function. Parameters for basal and maximal inositol phosphates, $EC_{50}$ or $IC_{50}$, and Hill coefficient were varied to achieve the best fit. The curve-fitting was weighted under the assumption that the standard deviation was proportional to dpm of radioactivity. Full concentration-response curves for AVP were run in each experiment, and $IC_{50}$ values were converted to $K_i$ values by application of the Cheng-Prusoff equation, based on the $EC_{50}$ for AVP in the same experiment. Inositol phosphates were expressed as dpm per $10^6$ dpm of total inositol incorporation.

Data analysis: competitivity experiments. Experiments to test for competitivity of test agents consisted of concentration-response curves for AVP in the absence and presence of two or more concentrations of test agent. Data were fit to a competitive logistic equation $$Y = B + \frac{M \times \{A/[E + (D/K)]\}^Q}{1 + \{A/[E + (D/K)]\}^Q}$$

where Y is dpm of inositol phosphates, B is concentration of basal inositol phosphates, M is the maximal increase in concentration of inositol phosphates, A is the concentration of agonist (AVP), E is the $EC_{50}$ for agonist, D is the concentration of antagonist (test agent), K is the KY for antagonist, and Q is the cooperativity (Hill coefficient).

Example 225 as produced a dose-dependent suppression of the action of AVP with $IC_{50}$ (2.68 nM) and $K_i$ (0.05 nM). These values are consistent with high affinity binding of Example 225 and its inhibition of inositol lipid synthesis via the human $V_{1a}$ receptor.

Method Example 3

Comparative binding to other receptors showing selectivity. Selective binding to the vasopressin $V_{1a}$ receptor was demonstrated for Example 225 at 100 nM against a panel of 63 other receptors provided by NOVASCREEN (Hanover, Md., USA). The results showed a high degree of specificity; Example 225 bound only to the $V_{1a}$ vasopressin receptor.

Method Example 4

Treatment of Premenstrual Syndrome (PMS) Antagonism of vasopressin $V_{1a}$ receptor has also been shown to alleviate or prevent the symptoms of premenstrual dysmenorrhoea dysphoria (PMDD) and primary dysmenorrhoea (PD). See generally, Brouard et al, in BJOG 107:614-19 (May 2000). Treatment is illustratively given shortly before the onset of menstruation as a preventative treatment of dysmenorrhoea.

An illustrative assay of vasopressin $V_{1a}$ antagonists in treating PMS is described herein and includes a double-blind, randomised, placebo-controlled, cross-over trial in complete block design (such as including three periods and three treatments). Illustrative treatment groups include women ages 18-35 years suffering from primary dysmenorrhoea. Daily dosing is made of either placebo or drug, where the drug dosing is illustratively about 0.5 mg to about 300 mg, or about 10 mg to about 200 mg, of a compound as described herein on a daily basis given singly or as divided doses. The dosing is given in the window from about 4 hours to about three days prior to the onset of bleeding and/or menstrual pain. Alternatively, patients may also be treated with a second daily dose.

Success outcomes include self-reporting of menstrual pain intensity by means of a visual analogue scale, self-rating of symptoms of dysmenorrhoea (including back and pelvic pain) in relation to functional capacity (using a Sultan score), and self-assessment of menstrual blood loss in a menstrual diary record.

In one aspect, the patient is administered treatment for primary dysmenorrhea by giving the dose one or more times per day for 5-7 days per month by an oral route. In another aspect of the method, the human patient is female having an age in the range from about 18 to about 40 years.

Method Example 5

Blood pressure pharmacology rats. Effects of the compounds described herein on vascular smooth muscle constriction and blood pressure show that the arginine vasopressin (AVP) $V_{1a}$ receptor appears to be a key mediator of premenstrual pain. Prior to menses, blood vessels in the uterine wall become engorged with blood. Vasopressin, acting through $V_{1a}$ receptors, causes constriction of both uterine and vascular smooth muscle contributing to the discomfort and pain of primary dysmenorrhea. Vasopressin is one of the endogenous factors that maintains vascular tone. Blocking the $V_{1a}$ receptors localized to smooth muscle may ameliorate the symptoms of primary dysmenorrhea. Elevated concentrations of vasopressin, acting through $V_{1a}$ receptors causes constriction of both uterine and vascular smooth muscle contributing to the discomfort and pain of primary dysmenorrhea. There are no animal models for evaluating receptor antagonists on dysmenorrhea. Instead, a simple blood pressure assay may be used to test the effects of the compounds described herein on the systemic vasculature. The rational for this approach rests on the observation that vasopressin $V_{1a}$ receptors are localized to blood vessels throughout the circulatory system. When stimulated by endogenous AVP from the pituitary gland, these receptors mediate vascular contraction of smooth muscle causing an increase in resistance and an elevation in blood pressure, as described by Liedman et al, in Acta Obstetricia et Gynecologica 85:207-211 (2006), the disclosure of which is incorporated herein by reference. It is suggested herein that this same AVP mediated constriction of blood vessels occurs in the uterus. Consequently, blockade of these receptors with a selective $V_{1a}$ receptor antagonist is expected to provide therapeutic benefits to women with Primary Dysmenorrhea (see also, Brouard et al, British Journal of Obstetrics and Gynecology 107:614-19 (2000). Additional information regarding the role of vasopressin $V_{1a}$ receptors in premenstrual disorders is described by French in American Family Physician 71(2):285 (2005).

Male rats were divided into five groups, and each group was tested with placebo, or one of four doses of one or more of the compounds described herein, such as with Example 225 at 0.16, 0.4, 1.0, and 2.5 mg/kg. Rats were treated orally with the compound and effects on blood pressure were measured 90-150 min later as follows. Under isoflurane anesthesia blood pressure was recorded through a cannula in the femoral artery. To increase systemic blood pressure AVP was administered (25 ng/kg) through a cannula in the femoral vein; the change in mean blood pressure was recorded two minutes following injection of AVP. Pretreatment of rats with Example 225 produced a dose-dependent inhibition of the AVP-induced rise in blood pressure. Rats treated with 1 and 2.5 mg/kg of Example 225 showed a significant (p<0.01) reduction in blood pressure as compared to vehicle and the two lower doses of antagonist. These data show that oral Example 225 can block a rise in blood pressure caused by activation of $V_{1a}$ receptors, and support that the other compounds described herein will do the same at appropriate doses, will be orally active and capable of blocking $V_{1a}$ receptors localized to uterine and vascular smooth muscle in human subjects.

Formulation Example 1

Hard gelatin capsules containing the following ingredients are prepared:

| Ingredient | Quantity (mg/capsule) |
| --- | --- |
| Vasopressin antagonist | 3.0-30 |
| Starch | 337-305 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Vasopressin antagonist | 2-25 |
| Cellulose, microcrystalline | 222-200 |
| Colloidal silicon dioxide | 10 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Vasopressin antagonist | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Vasopressin antagonist | 3-30 mg |
| Starch | 72-45 mg |
| Microcrystalline cellulose | 62-35 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch, and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Vasopressin antagonist | 4-40 mg |
| Starch | 145-109 mg |
| Magnesium stearate | 1.0 mg |
| Total | 150 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Quantity (mg) |
|---|---|
| Vasopressin antagonist | 2-25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Quantity (mg) |
|---|---|
| Vasopressin antagonist | 5-50 mg |
| Xanthan gum | 4.0 mg |
| Sodium carboxymethyl cellulose(11%) Microcrystalline cellulose (89%) | 95-50 mg |
| Sucrose | 1.75 g |
| Sodium benzoate | 10.0 mg |
| Flavor and Color | q.v. |
| Purified water to | 5.0 ml |

The medicament, sucrose, and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
|---|---|
| Vasopressin antagonist | 1.5-15 mg |
| Starch | 421-407 mg |
| Magnesium stearate | 3.0 mg |
| Total | 425 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity (mg) |
|---|---|
| Vasopressin antagonist | 25-250 mg |
| Isotonic saline | 1000 ml |

Formulation Example 10

A topical formulation may be prepared as follows:

| Ingredient | Quantity (mg) |
|---|---|
| Vasopressin antagonist | 0.1-1 g |
| Emulsifying Wax | 30 g |
| Liquid Paraffin | 20 g |
| White Soft Paraffin to | 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity (mg/tablet) |
| --- | --- |
| Vasopressin antagonist | 1-10 mg |
| Glycerol | 210 mg |
| Water | 143 mg |
| Sodium Citrate | 4.5 mg |
| Polyvinyl Alcohol | 26.5 mg |
| Polyvinylpyrrolidone | 15.5 mg |
| Total | 401-410 mg |

The glycerol, water, sodium citrate, polyvinyl alcohol, and polyvinylpyrrolidone are admixed together by continuous stirring and maintaining the temperature at about 90° C. When the polymers have gone into solution, the resulting solution is cooled to about 50-55° C. and the medicament is slowly admixed. The homogenous mixture is poured into forms made of an inert material to produce a drug-containing diffusion matrix having a thickness of about 2-4 mm. This diffusion matrix is then cut to form individual tablets having the appropriate size.

Another illustrative formulation for the compounds described herein includes transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Another illustrative formulation for the compounds described herein includes direct or indirect introduction to the brain. Direct techniques may include placement of a drug delivery catheter into the patient's ventricular system to bypass the blood-brain barrier. One illustrative implantable delivery system, used for the transport of biological factors to specific anatomical regions of the body, is described in U.S. Pat. No. 5,011,472, which is herein incorporated by reference.

Indirect techniques may include formulating the compositions to provide for drug latentiation by the conversion of hydrophilic drugs into lipid-soluble drugs or prodrugs. Latentiation may be achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions that can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

While the invention has been illustrated and described in detail in the foregoing description, such an illustration and description is to be considered as exemplary and not restrictive in character, it being understood that only the illustrative embodiments have been shown and described and that all changes and modifications that come within the spirit of the invention are contemplated as further embodiments.

What is claimed is:

1. A method for treating the emotional symptoms of a premenstrual disorder selected from the group consisting of premenstrual dysphoric disorder, premenstrual syndrome, and a combination thereof, the method comprising the step of administering an effective amount of a compound to a patient in need of relief from the disorder, where the compound is of the formula 2(S)-[4-(2-phenylethyl)piperazinyl-carbonylethyl]-2-[3 (S)-(4(S)-phenyloxazolidin-2-on-3-yl)-4(R)-(2-styryl) azetidin-2-on-1-yl]acetic acid N-(3-trifluoromethylbenzyl)amide;

2(R)-[[4-(Piperidinyl)piperidinyl]carbonylmethyl]-2-[3 (S)-(4(S)-phenyloxazolidin-2-on-3-yl)-4(R)-(2-styryl) azetidin-2-on-1-yl]acetic acid N-(2-fluoro-3-trifluoromethylbenzyl)carboxamide;

2(R)-[[4-(Piperidinyl)piperidinyl]carbonylmethyl]-2-[3 (S)-(4(S)-phenyloxazolidin-2-on-3-yl)-4(R)-(2-styryl) azetidin-2-on-1-yl]acetic acid N—[(R)-α-methylbenzyl]amide;

2(R)-[[4-(Piperidinyl)piperidinyl]carbonylmethyl]-2-[3 (S)-(4(S)-phenyloxazolidin-2-on-3-yl)-4(R)-(2-styryl) azetidin-2-on-1-yl]acetic acid N-methyl-N-(3-trifluoromethylbenzyl)amide;

(2S)-[(4-cyclohexylpiperazinyl)carbonylethyl]-2-[3(S)-(4 (S)-phenyloxazolidin-2-on-3-yl)-4(R)-(2-phenyleth-1-yl)azetidin-2-on-1-yl]acetic acid N-(3-trifluoromethylbenzyl)amide;

(2S)-(Benzylthiomethyl)-2-[3(S)-(4(S)-phenyloxazolidin-2-on-3-yl)-4(R)-(2styryl)azetidin-2-on-1-yl]acetic acid N-[4-[2-(piperid-1-yl)ethyl]piperidin-1-yl]amide;

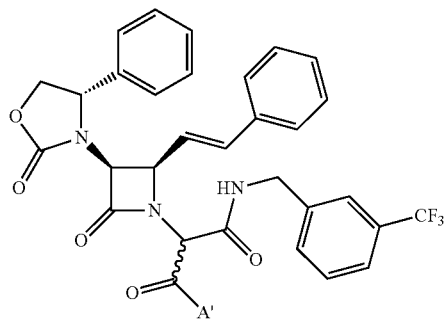

where A' is 4-[2-(piperidinyl)ethyl]piperidinyl;

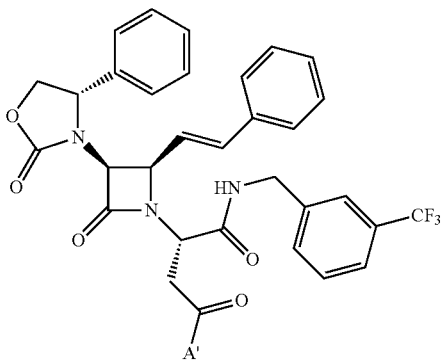

where A' is 1-benzylpiperidin-4-ylamino;

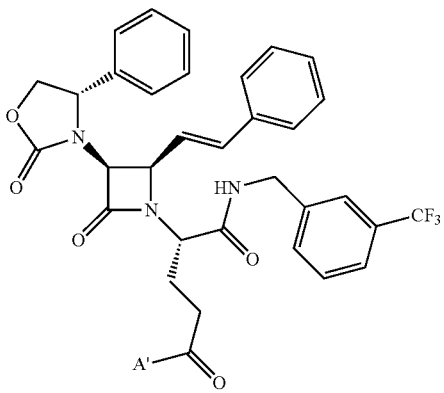

where A' is 4-benzylpiperazinyl, 4-butylpiperazinyl, 4-isopropylpiperazinyl, 4-cyclohexylpiperazinyl, 4-(2-cyclohexylethyl)piperazinyl, 4-[2-(morpholin-4-yl)ethyl]piperazinyl, or 4-(cyclohexylmethyl)piperazinyl;

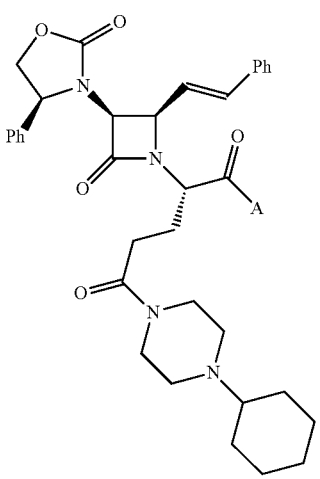

where A is (3,5-dichlorobenzyl)amino, (2,3-dichlorobenzyl)amino, (2-fluoro-5-trifluoromethylbenzyl)amino, (3-fluoro-5-trifluoromethylbenzyl)amino, (2-fluoro-3-trifluoromethylbenzyl)amino, (2-trifluoromethylbenzyl)amino, (3,5-difluorobenzyl)amino, (3-chlorobenzyl)amino, (3-nitrobenzyl)amino, (3-bromobenzyl)amino, (3-methylbenzyl)amino, N-methyl-N-(3-trifluoromethylbenzyl)amino, [(S)-α-methylbenzyl]amino, [(5-methylfur-2-yl)methyl]amino, (thien-2-ylmethyl)amino, [(S)-1,2,3,4-tetrahydro-1-naphth-1-yl]amino, [(R)-1,2,3,4-tetrahydro-1-naphth-1-yl]amino, (indan-1-yl)amino, (2,5-dimethoxybenzyl)amino, N-methyl-2,3-Cl-benzylamide, (R)-1-(3-trifluorophenyl)ethylamide, 1-phenyl-cyclohexylamide, or indan-2-ylamino;

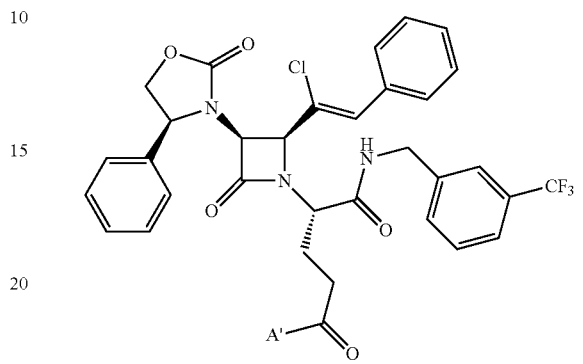

where A' is 4-cyclohexylpiperazinyl or 4-n-butylpiperazinyl; or

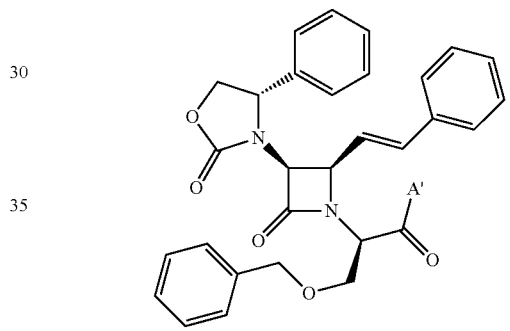

where A' is 4-(piperidinyl)piperidinyl, 4-(piperidinylmethyl)piperidinyl, or 4-[2-(piperidinyl)ethyl]piperidinyl;
or a pharmaceutically acceptable salt thereof.

2. The method of claim 1 wherein the compound is of the formula:

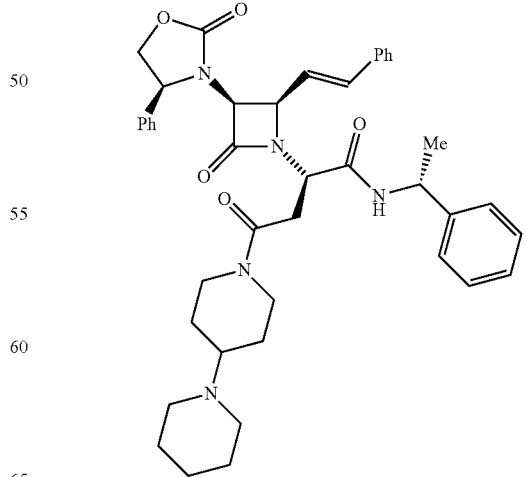

or a pharmaceutically acceptable salt thereof.

3. The method of claim 1 wherein the premenstrual disorder is accompanied by primary dysmenorrhea.

4. The method of claim 1 wherein the compound is of the formula:

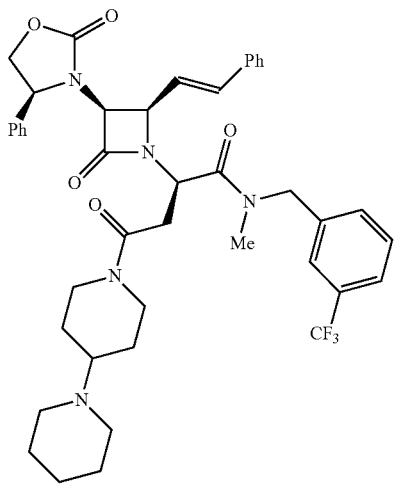 [SMILES: CN(Cc1cccc(C(F)(F)F)c1)C(=O)[C@@H](CC(=O)N1CCC(N2CCCCC2)CC1)N1C(=O)[C@@H](N2C(=O)OC[C@@H]2c2ccccc2)[C@H]1/C=C/c1ccccc1]

or a pharmaceutically acceptable salt thereof.

5. The method of claim 2 wherein the premenstrual disorder is premenstrual syndrome.

6. The method of claim 2 wherein the premenstrual disorder is premenstrual dysphoric disorder.

7. The method of claim 4 wherein the premenstrual disorder is premenstrual syndrome.

8. The method of claim 4 wherein the premenstrual disorder is premenstrual dysphoric disorder.

* * * * *